United States Patent
Kohli et al.

(10) Patent No.: US 11,259,879 B2
(45) Date of Patent: Mar. 1, 2022

(54) SELECTIVE TRANSPARENCY TO ASSIST MEDICAL DEVICE NAVIGATION

(71) Applicant: InnerOptic Technology, Inc., Hillsborough, NC (US)

(72) Inventors: Luv Kohli, Durham, NC (US); Andrei State, Chapel Hill, NC (US); Sharif Razzaque, Boulder, CO (US)

(73) Assignee: InnerOptic Technology, Inc., Hillsborough, NC (US)

(*) Notice: Subject to any disclaimer, the term of this patent is extended or adjusted under 35 U.S.C. 154(b) by 672 days.

(21) Appl. No.: 16/052,289

(22) Filed: Aug. 1, 2018

(65) Prior Publication Data

US 2019/0060001 A1 Feb. 28, 2019

Related U.S. Application Data

(60) Provisional application No. 62/539,729, filed on Aug. 1, 2017.

(51) Int. Cl.
*A61B 5/00* (2006.01)
*A61B 34/20* (2016.01)
(Continued)

(52) U.S. Cl.
CPC .............. *A61B 34/20* (2016.02); *A61B 90/37* (2016.02); *A61B 34/25* (2016.02);
(Continued)

(58) Field of Classification Search
CPC ... A61B 34/20; A61B 90/37; A61B 2090/378; A61B 2034/2051; A61B 2034/2055;
(Continued)

(56) References Cited

U.S. PATENT DOCUMENTS

| | | |
|---|---|---|
| 3,556,079 A | 1/1971 | Omizo |
| 4,058,114 A | 11/1977 | Soldner |

(Continued)

FOREIGN PATENT DOCUMENTS

| | | |
|---|---|---|
| EP | 0 427 358 | 5/1991 |
| JP | S63-290550 A | 11/1988 |

(Continued)

OTHER PUBLICATIONS

U.S. Appl. No. 11/828,826 including its ongoing prosecution history, including without limitation Office Actions, Amendments, Remarks, and any other potentially relevant documents, filed Jul. 26, 2007, Keller et al.

(Continued)

*Primary Examiner* — Joel Lamprecht
(74) *Attorney, Agent, or Firm* — Knobbe Martens Olson & Bear, LLP

(57) ABSTRACT

A system and method for image guidance providing improved perception of a display object in a rendered scene for medical device navigation. The system can receive emplacement information associated with a medical device and determine an emplacement of a display object associated with the medical device. The system can further identify a selected surface of the display object and cause a display to display a selective-transparency rendering of the selected surface.

18 Claims, 18 Drawing Sheets

(51) Int. Cl.
*A61B 90/00* (2016.01)
*A61B 34/10* (2016.01)
*A61B 34/00* (2016.01)
*A61B 90/50* (2016.01)

(52) U.S. Cl.
CPC . *A61B 2034/102* (2016.02); *A61B 2034/2048* (2016.02); *A61B 2034/2051* (2016.02); *A61B 2034/2055* (2016.02); *A61B 2034/2072* (2016.02); *A61B 2090/365* (2016.02); *A61B 2090/367* (2016.02); *A61B 2090/372* (2016.02); *A61B 2090/378* (2016.02); *A61B 2090/502* (2016.02)

(58) Field of Classification Search
CPC ............ A61B 34/25; A61B 2034/2048; A61B 2090/502; A61B 2090/372; A61B 2090/365; A61B 2034/102; A61B 2090/367; A61B 2034/2072
See application file for complete search history.

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,806,521 A | 9/1998 | Morimoto et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,784 B1 | 6/2001 | Summers et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |

(56) References Cited

U.S. PATENT DOCUMENTS

| | | |
|---|---|---|
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de La Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,265,572 B2 | 2/2016 | Fuchs et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,659,345 B2 | 5/2017 | Razzaque et al. |
| 9,675,319 B1 | 6/2017 | Razzaque et al. |
| 9,901,406 B2 | 2/2018 | State et al. |
| 9,949,700 B2 | 4/2018 | Razzaque et al. |
| 10,026,191 B2 | 7/2018 | Accomando et al. |
| 10,127,629 B2 | 11/2018 | Razzaque et al. |
| 10,136,951 B2 | 11/2018 | Razzaque et al. |
| 10,188,467 B2 | 1/2019 | Razzaque et al. |
| 10,278,778 B2 | 5/2019 | State et al. |
| 10,314,559 B2 | 6/2019 | Razzaque et al. |
| 10,398,513 B2 | 9/2019 | Razzaque et al. |
| 10,433,814 B2 | 10/2019 | Razzaque et al. |
| 10,733,700 B2 | 8/2020 | Keller et al. |
| 10,772,686 B2 | 9/2020 | State et al. |
| 10,820,944 B2 | 11/2020 | State et al. |
| 10,820,946 B2 | 11/2020 | Heaney et al. |
| 2001/0007919 A1 | 7/2001 | Shahidi |
| 2001/0016804 A1 | 8/2001 | Cunningham et al. |
| 2001/0031920 A1 | 10/2001 | Kaufman et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |

(56) References Cited

U.S. PATENT DOCUMENTS

| | | |
|---|---|---|
| 2002/0077540 A1 | 6/2002 | Kienzle, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0032878 A1 | 2/2003 | Shahidi |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2003/0233123 A1 | 12/2003 | Kindlein et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0033160 A1 | 2/2005 | Yamagata et al. |
| 2005/0085717 A1 | 4/2005 | Shahidi |
| 2005/0085718 A1 | 4/2005 | Shahidi |
| 2005/0090733 A1 | 4/2005 | Van Der Lugt et al. |
| 2005/0090742 A1 | 4/2005 | Mine et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1 | 10/2005 | Suzuki et al. |
| 2005/0240094 A1 | 10/2005 | Pichon et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0024617 A1 | 2/2007 | Poole |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1 | 5/2009 | Masao et al. |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0198402 A1 | 8/2010 | Greer et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1 | 2/2011 | Fuchs et al. |
| 2011/0057930 A1 | 3/2011 | Keller |
| 2011/0082351 A1 | 4/2011 | Razzaque et al. |
| 2011/0137156 A1* | 6/2011 | Razzaque .......... A61B 18/1477 600/424 |
| 2011/0201915 A1 | 8/2011 | Gogin et al. |
| 2011/0201976 A1 | 8/2011 | Sanghvi et al. |
| 2011/0208055 A1 | 8/2011 | Dalal et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0108955 A1 | 5/2012 | Razzaque et al. |
| 2012/0138658 A1 | 6/2012 | Ullrich et al. |
| 2012/0143029 A1 | 6/2012 | Silverstein et al. |
| 2012/0143055 A1 | 6/2012 | Ng et al. |

(56) References Cited

U.S. PATENT DOCUMENTS

| | | | |
|---|---|---|---|
| 2012/0165679 A1 | 6/2012 | Orome et al. | |
| 2012/0215096 A1 | 8/2012 | Gilboa | |
| 2012/0230559 A1 | 9/2012 | Itai | |
| 2012/0237105 A1 | 9/2012 | Mielekamp | |
| 2012/0259210 A1 | 10/2012 | Harhen et al. | |
| 2013/0030286 A1 | 1/2013 | Alouani et al. | |
| 2013/0044930 A1 | 2/2013 | Li et al. | |
| 2013/0079770 A1 | 3/2013 | Kyle, Jr. et al. | |
| 2013/0090646 A1 | 4/2013 | Moss et al. | |
| 2013/0096497 A1 | 4/2013 | Duindam et al. | |
| 2013/0132374 A1 | 5/2013 | Olstad et al. | |
| 2013/0144165 A1 | 6/2013 | Ebbini et al. | |
| 2013/0151533 A1 | 6/2013 | Udupa et al. | |
| 2013/0178745 A1 | 7/2013 | Kyle et al. | |
| 2013/0218024 A1 | 8/2013 | Boctor et al. | |
| 2013/0249787 A1 | 9/2013 | Morimoto | |
| 2014/0051987 A1 | 2/2014 | Kowshik et al. | |
| 2014/0058387 A1 | 2/2014 | Kruecker et al. | |
| 2014/0078138 A1 | 3/2014 | Martin et al. | |
| 2014/0180074 A1 | 6/2014 | Green | |
| 2014/0201669 A1 | 7/2014 | Liu et al. | |
| 2014/0275760 A1 | 9/2014 | Lee et al. | |
| 2014/0275810 A1 | 9/2014 | Keller et al. | |
| 2014/0275997 A1 | 9/2014 | Chopra et al. | |
| 2014/0350390 A1 | 11/2014 | Kudavelly et al. | |
| 2015/0238259 A1 | 8/2015 | Albeck et al. | |
| 2015/0257847 A1 | 9/2015 | Higgins et al. | |
| 2016/0166334 A1 | 6/2016 | Razzaque | |
| 2016/0196694 A1 | 7/2016 | Lindeman | |
| 2016/0270862 A1 | 9/2016 | Fuchs et al. | |
| 2016/0354152 A1 | 12/2016 | Beck | |
| 2017/0065352 A1* | 3/2017 | Razzaque | G06T 19/003 |
| 2017/0099479 A1 | 4/2017 | Browd et al. | |
| 2017/0348067 A1 | 12/2017 | Krimsky | |
| 2018/0289344 A1 | 10/2018 | Green et al. | |
| 2019/0021681 A1 | 1/2019 | Kohli | |
| 2019/0167354 A1 | 6/2019 | Heaney et al. | |
| 2019/0223958 A1 | 7/2019 | Kohli | |
| 2019/0247130 A1 | 8/2019 | State | |
| 2020/0046315 A1 | 2/2020 | State | |
| 2020/0138402 A1 | 5/2020 | Kohli | |
| 2021/0027418 A1 | 1/2021 | Keller | |
| 2021/0113273 A1 | 4/2021 | State | |
| 2021/0161600 A1 | 6/2021 | Heaney | |
| 2021/0161601 A1 | 6/2021 | State | |

FOREIGN PATENT DOCUMENTS

| | | |
|---|---|---|
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 13/116240 | 8/2013 |
| WO | WO 18/080844 | 5/2018 |

OTHER PUBLICATIONS

U.S. Appl. No. 15/068,323 including its ongoing prosecution history, including without limitation Office Actions, Amendments, Remarks, and any other potentially relevant documents, filed Mar. 11, 2016, Razzaque et al.

U.S. Appl. No. 16/255,629, filed Jan. 23, 2019, Kohli.

"3D Laparoscope Technology," http://www.inneroptic.com/tech_3DL.htm, copyright 2007 InnerOptic Technology, Inc. printed Sep. 19, 2007, 2 pages.

"AIM 3D Needle Placement Software from InnerOptic", Medgadget, Sep. 21, 2012.

AIM Section 5: 510k Summary, submitted by InnerOptic Technology, Inc., in 5 pages, submission date May 17, 2012.

"Cancer Facts & Figures 2004," www.cancer.org/downloads/STT/CAFF_finalPWSecured.pdf, copyright 2004 American Cancer Society, Inc., printed Sep. 19, 2007, 60 pages.

Cancer Prevention & Early Detection Facts & Figures 2004; National Center for Tobacco-Free Kids; 2004; American Cancer Society; USA.

"David Laserscanner <-Latest News <-Institute for Robotics and Process Control <-Te . . . ," http://www/rob.cs.tu-bs.de/en/news/david, printed Sep. 19, 2007, 1 page.

"InnerOptic's AIM System Receives DA 510(K) Clearance", InnerOptic Technology, Inc., Sep. 18, 2012.

"Laser scanned 3d model Final" video, still image of video attached, http://www.youtube.com/watch?v=DaLgIgmoUf8, copyright 2007 YouTube, LLC, printed Sep. 19, 2007, 2 pages.

"Olympus Endoscopic Ultrasound System," www.olympusamerica.com/msg_section/download_brochures/135_b_gfum130.pdf, printed Sep. 20, 2007, 20 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"Robbins, Mike—Computer Vision Research—Stereo Depth Perception," http://www.compumike.com/vision/stereodepth.php, copyright 2007 Michael F. Robbins, printed Sep. 19, 2007, 3 pages.

"RUE, Registered Ultrasound-Endoscope," copyright 2007 InnerOptic Technology, Inc., 2 pages.

Advertisement, "Inspeck 3DC 3D Capturor," Inspeck 3DC 3D Capturor (www.inspeck.com), 1998.

Advertisement, "Virtual 3D High Speed Non-Contact Surface Perception," Virtual 3-D Technologies Corporation (www.virtual3dtech.com)., Dec. 21, 1998.

Advertisements, "Virtuoso," Visual Interface, Inc. (www.visint.com), Dec. 21, 1998.

Akka, "Automatic Software Control of Display Parameters for Stereoscopic Graphics Images," SPIE vol. 1669: Stereoscopic Displays and Applications III, pp. 31-38 (1992).

Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Aylward et al., Analysis of the Parameter Space of a Metric for Registering 3D Vascular Images, in W. Niessen and M. Viergever (Eds.): MICCAI 2001, LNCS 2208, pp. 932-939, 2001.

Aylward et al., Registration and Analysis of Vascular Images, International Journal of Computer Vision 55(2/3), 123-138, 2003.

Aylward, et al., Intra-Operative 3D Ultrasound Augmentation, Proceedings of the IEEE International Symposium on Biomedical Imaging, Washington, Jul. 2002.

Azuma et al., "Improving Static and Dynamic Registration in an Optical See-Through HMD," Paper Presented at SIGGRAPH '94 Annual Conference in Orlando, FL, 17 pages (1994).

Azuma, "A Survey of Augmented Reality," Presence: Teleoperators and Virtual Environments 6, 4:1-48 (Aug. 1997).

Badler et al., "Simulating Humans: Computer Graphics, Animation, and Control," Oxford University Press (1993).

Bajura, Michael et al., "Merging Virtual Objects with the Real World: Seeing Ultrasound Imagery within the Patient," Computer Graphics, Proceedings of SIGGRAPH 1992, vol. 26(2), pp. 203-

(56) References Cited

OTHER PUBLICATIONS 210, available from www.cs.unc.edu/~fuchs/publications/MergVirtObjs92.pdf, printed Sep. 20, 2007, 8 pages.

Benavides et al., "Multispectral digital colposcopy for in vivo detection of cervical cancer," Optics Express; May 19, 2003; 11 (10) Optical Society of America; USA.

Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.

Billinghurst, M. et al., Research Directions in Handheld AR; Int. J. of Virtual Reality 5(2),51-58 (2006).

Blais, F., "Review of 20 Years of Range Sensor Development," Journal of Electronic Imaging, 13(1):231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

Bouguet, Jean-Yves, "Camera Calibration Toolbox for Matlab," www.vision.caltech.edu/bouguetj/calib_doc, printed Sep. 20, 2007, 5 pages.

Buxton et al.; "Colposcopically directed punch biopsy: a potentially misleading investigation," British Journal of Obstetrics and Gynecology; Dec. 1991; 98:1273-1276.

Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.

Cantor et al., "Cost-Effectiveness Analysis of Diagnosis and Management of Cervical Squamous Intraepithelial Lesions," Diagnostic Strategies for SILs; Feb. 1998; 91(2):270-277.

Catalano et al. "Multiphase helical CT findings after percutaneous ablation procedures for hepatocellular carcinoma." Abdom. Imaging, 25(6),2000, pp. 607-614.

Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.

Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Deering, Michael "High Resolution Virtual Reality." Proceedings of SIGGRAPH '92, Computer Graphics, 26(2), 1992, pp. 195-202.

Depiero et al., "3-D Computer Vision Using Structured Light: Design, Calibration and Implementation Issues," The University of Tennessee, pp. 1-46, (1996).

Dodd, G.D. et al. "Minimally invasive treatment of malignant hepatic tumors: at the threshold of a major breakthrough." Radiographies 20(1),2000, pp. 9-27.

Drascic et al., "Perceptual Issues in Augmented Reality," SPIE vol. 2653: Stereoscopic Displays and Virtual Reality Systems III, pp. 123-134 (Feb. 1996).

Dumoulin, C.L. et al, Real-Time Position Monitoring of Invasive Devices Using Magnetic Resonance, Magnetic Resonance in Medicine, vol. 29, Issue 3, Mar. 1993, pp. 411-415.

Edwards et al., Video See-Through Design for Merging of Real and Virtual Environments, VRAIS '93, pp. 1-11 (1993).

Fahey et al., "Meta-analysis of Pap Test Accuracy; American Journal of Epidemiology," 1995 141 (7):680-689; The John Hopkins University School of Hygiene and Public Health; USA.

Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).

Fronheiser et al., Real-Time 3D Color Doppler for Guidance of Vibrating Interventional Devices, IEEE Ultrasonics Symposium, pp. 149-152 (2004).

Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg98.pdf, printed Sep. 20, 2007, 10 pages.

Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.

Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.

Fuhrmann A. et al., Comprehensive calibration and registration procedures for augmented reality; Proc. Eurographics Workshop on Virtual Environments 2001,219-228 (2001).

Garrett, William F. et al., "Real-Time Incremental Visualization of Dynamic Ultrasound Volumes Using Parallel BSP Trees, "Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

StereoMirror Technology Webpage, http://www.planar.com/products/flatpanel_monitors/stereoscopic/ (Printed Dec. 29, 2011).

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413-432 (1997).

Hornung et al., "Quantitative near-infrared spectroscopy of cervical dysplasia in vivo," Human Reproduction; 1999; 14(11):2908-2916; European Society of Human Reproduction and Embryology.

Howard, M.D., et al.: "An Electronic Device for Needle Placement during Sonographically Guided Percutaneous Intervention", Radiology 2001; 218:905-911.

InnerAim Brochure; 3D Visualization Software for Simpler, Safer, more Precise Aiming, Published no earlier than Apr. 1, 2010.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.es.unc.edu/~us/Latency//ManagingRelativeLatency.html, printed Sep. 20, 2007, 12 pages.

Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.

Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.

Kanbara et al., "A Stereoscopic Video See-through Augmented Reality System Based on Real-time Vision-Based Registration," Nara Institute of Science and Technology, pp. 1-8 (2000).

Kato, Amami, et al., A frameless, armless navigational system for computer-assisted neurosurgery, Journal of Neurosurgery, vol. 74, No. 5, May 1991, pp. 845-849.

Keller et al., "What is it in Head Mounted Displays (MDs) that really make them all so terrible?," pp. 1-8 (1998).

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

(56) References Cited

OTHER PUBLICATIONS

Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 (August), 1997: pp. 231-237.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Lipton, "Foundations of the Steroscopic Cinema A Study in Depth," Van Nostrad Reinhold Company, pp. 1-319 (1982).
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
Ohnesorge, Lauren K., "InnerOptic technology wins FDA approval", Triangle Business Journal, Sep. 19, 2012.
Pogue, Brian W. et al., "Analysis of acetic acid-induced whitening of high-grade squamous intraepitheliallesions," Journal of Biomedical Optics; Oct. 2001; 6(4):397-403.
Press Release: Pathfinder and InnerOptic Announce Technology Integration to Enhance Visualization and Outcomes in Liver Surgery, Published Mar. 6, 2013.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al, "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.
State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, 10 pages (Aug. 1996).
State et al., "Technologies for Augmented Reality Systems: Realizing Ultrasound-Guided Needle Biopsies," Proc. SIGGRAPH 96 (New Orleans, LA, Aug. 4-9, 1996). In Computer Graphics Proceedings, Annual Conference Series, 1996, ACM SIGGRAPH, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Entertaining Computing 2005, LNCS, vol. 3711, pp. 268-278 (2005).
Ultraguide 1000 System, Ultraguide, www.ultraguideinc.com, 1998.

(56) References Cited

OTHER PUBLICATIONS

Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 137-154 (1997).
Viola, Paul A., Alignment by Maximization of Mutual Information, Ph.D. Dissertation, MIT—Artificial Intelligence Laboratory Technical Report No. 1548 (Jun. 1995), 156 pages.
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).

\* cited by examiner

__SELECTIVE TRANSPARENCY TO ASSIST MEDICAL DEVICE NAVIGATION__

CROSS-REFERENCE TO RELATED APPLICATIONS

The present application claims priority benefit to U.S. Provisional Application No. 62/539,729, entitled "MONOSTABLE TRANSPARENCY TO ASSIST MEDICAL DEVICE NAVIGATION," filed Aug. 1, 2017, which is hereby incorporated herein by reference in its entirety. Any and all applications for which a foreign or domestic priority claim is identified in the Application Data Sheet as filed with the present application are incorporated by reference under 37 CFR 1.57 and made a part of this specification.

BACKGROUND

Various systems are available to aid a healthcare provider to guide a medical device in a patient or to provide a user viewing an object with additional information. The systems can provide image guidance cues to aid the healthcare provider or user and can also provide additional information for the user's benefit.

DETAILED DESCRIPTION

Figure 1A:
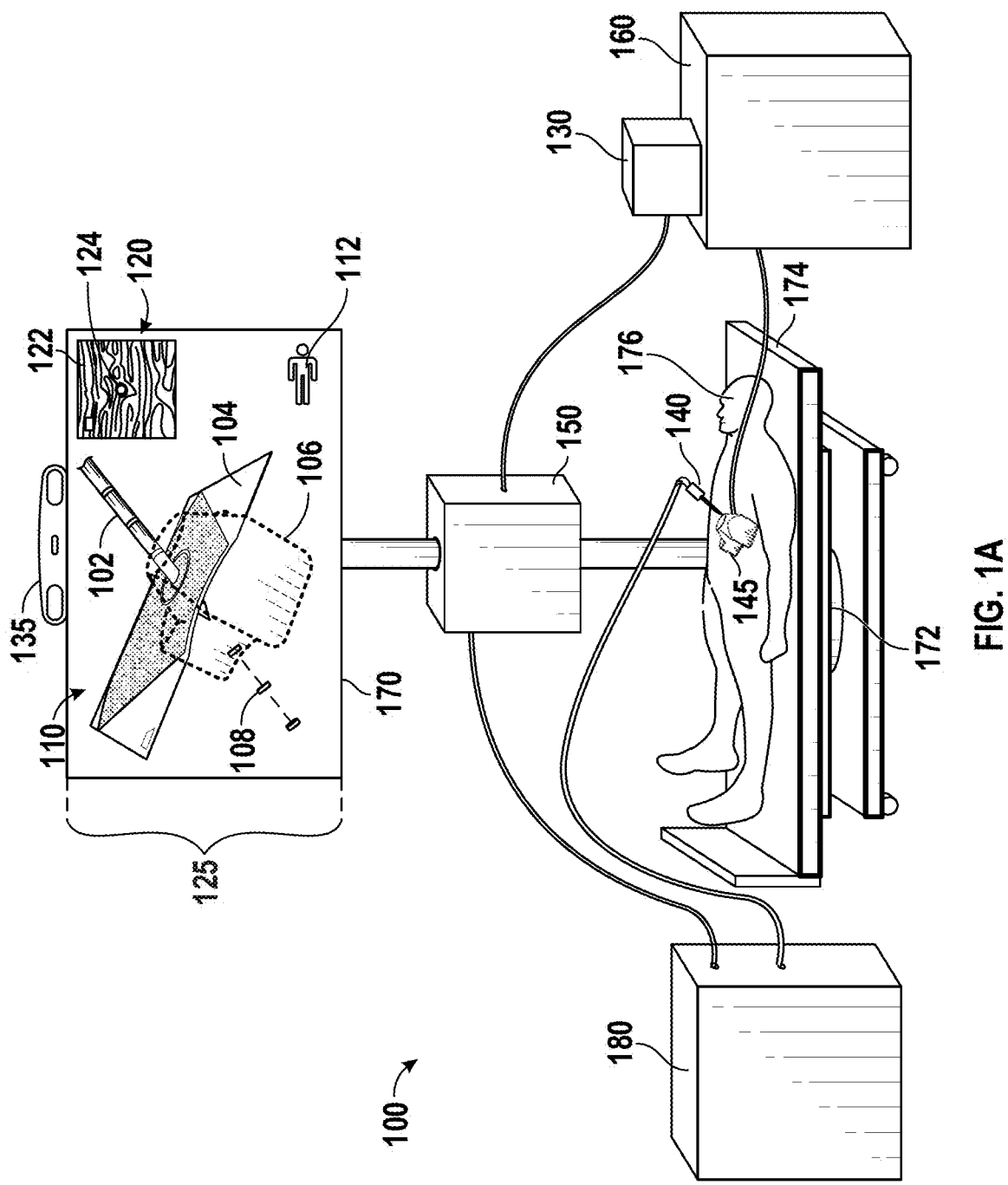
FIG. 1A is a diagram illustrating an embodiment of an environment for image-guided medical procedures.

During image-guided medical procedures, displaying virtual medical devices that resemble real medical devices can help healthcare providers associate a virtual scene with the real world, and can provide more familiar guidance information to the healthcare provider, thereby further aiding the healthcare provider in the guidance task.

During these image-guided procedures, it can be important for a physician to understand spatial relationships between display objects, such as the relationships between virtual medical devices, medical images, or other display objects involved. Misinterpreting the relationships between the tools, or between the physician and a tool, can potentially lead to patient harm. Nonetheless, especially when multiple display objects are shown on a display, it can be easy for a physician to misinterpret or misunderstand the spatial relationships. These problems can be further exacerbated if one or more of the display objects overlaps on the display, as the spatial relationships become even more ambiguous.

In some implementations, the system disclosed herein provides improved perception of a display object in a virtual 3D scene for medical device navigation. For example, the system can use a selective-transparency rendering to display one or more objects in the scene. The selective-transparency rendering can be a selective-transparency surface rendering (e.g., selective-transparency beginning-surface rendering, selective-transparency ending-surface rendering, selective-transparency front-surface rendering, selective-transparency back-surface rendering), a selective-transparency object rendering (e.g., selective-transparency first object rendering, selective-transparency last object rendering, selective-transparency selected object rendering, etc.), etc.

The selective-transparency surface rendering can include a rendering of a selected surface at one or more transparency levels. For example, if the selected surface is a beginning-surface, in some cases, the system can render a display object such that, at each pixel, the nearest parts of that display object (relative to a point-of-view location) are shown at one or more transparency levels. Further, the system can omit other surfaces or portions of the display object. In other words, in certain embodiments, the system can render just those portions of the display object that both face the viewer and are unobstructed from the viewer by the object's shape (for example, the object's concavities).

In some cases, the system can display the selected surface of the display object at one or more transparency levels. The transparency levels can refer to how transparent an object or line of an object is to be drawn. For example, complete transparency or maximum transparency level can refer to an object not being visible, a higher transparency level can refer to lines of an object being faintly drawn (e.g., shown at 10-20% of the darkness of an opaque line), a low transparency level can refer to lines of an object that are drawn darker (e.g., shown at 70-80% of the darkness of an opaque line), and a lowest transparency level or opaque can refer to a solid line, such as a solid black line.

It will be understood that reference to displaying surfaces or objects at different transparency levels can refer to drawing portions of the objects with opaque lines or no transparency, drawing portions of the object with semi-transparent lines (higher or lower levels of transparency) and/or drawing portions of the object completely transparent. For example, the display object can be rendered such that portions of the selected surface that are closer to an edge of the object are displayed more opaquely than portions of the selected surface that are farther away from the edge. As another example, the display object can be rendered such that only edges of the selected surface are displayed or are displayed more opaquely than other portions of the selected surface. In this way, other display objects that are potentially behind the display object would be visible through the display object, thereby clearly conveying the spatial relationships of the display objects.

In some cases, it can be advantageous to additionally or alternatively display subtle, unobtrusive but useful details about the most distant surface of the display object. For example, the system can identify and display the most distant (or "ending") surfaces or portions of the display object. In some cases, the system can render the beginning-surface of the display object, and can render the ending-surface with diminished opacity as compared to the beginning-surface, or with reduced contrast or modified color. By providing the viewer with an indication as to the closest portion (beginning-surface) and/or farthest portion (ending-surface) of the display object, the system can display the display object with improved perception. Likewise, by utilizing combinations of opacity, hue, saturation, and brightness for the beginning- and ending-surfaces, the system can further improve the perception of the display object, especially as compared with a display object that is displayed with a single transparency level.

Overview

Implementations disclosed herein provide systems, methods, and apparatus for displaying medical images, such as, but not limited to ultrasound, CT, and/or MRI images, facilitating medical device insertion into tissue by an operator. Certain embodiments pertain to a free-hand medical device guidance system. The system can provide the healthcare provider manual control over the medical device, while making the spatial relationships between the target, medical device and medical image (also referred to as an image slice or rendered medical image), or image area corresponding to the medical image (also referred to as an image slice area or scan area), more intuitive via a visual display. Using this visual feedback, the operator can adjust the medical device's position, orientation, or trajectory. Certain of the contemplated embodiments can be used in conjunction with systems described in greater detail in U.S. patent application Ser. No. 13/014,587, filed Jan. 26, 2011, entitled "SYSTEMS, METHODS, APPARATUSES, AND COMPUTER-READABLE MEDIA FOR IMAGE MANAGEMENT IN IMAGE-GUIDED MEDICAL PROCEDURES." U.S. patent application Ser. No. 13/753,274, filed Jan. 29, 2013, entitled "MULTIPLE MEDICAL DEVICE GUIDANCE" (the '274 Application), U.S. patent application Ser. No. 14/213,033, filed Mar. 14, 2014, entitled "MEDICAL DEVICE GUIDANCE," U.S. patent application Ser. No. 14/872,930, filed Oct. 1, 2015, entitled "AFFECTED REGION DISPLAY" (the '930 Application), U.S. patent application Ser. No. 15/199,630, filed Jun. 30, 2016, entitled "LOUPE DISPLAY," and U.S. patent application Ser. No. 15/415,398, filed Jun. 30, 2016, entitled "MEDICAL INSTRUMENT NAVIGATION," each of which is hereby incorporated by reference in its entirety.

Medical interventions typically involve using an instrument to insert into, resect, cauterize, staple, seal, or otherwise manipulate soft tissue and organs. A physician must take great care to minimize blood loss and minimize damage to ancillary tissue while performing these tissue-altering interventions. This is even more difficult with minimally-invasive surgeries, such as laparoscopic, endoscopic, and robotic surgeries. A physician may use ultrasound to image the internal structures of an organ before stapling, transecting, resecting, sealing, grasping, or inserting a medical device into tissue, helping her avoid critical structures such as blood vessels. However, even with ultrasound imaging, there is a significant possibility of inadvertent damage to surrounding tissue and blood vessels during these procedures. This is because it is not obvious in the externally displayed medical image where a given internal structure is located relative to the medical device.

The system can aid the healthcare provider in guiding one or more medical devices through or around tissue of the patient and/or placing the medical devices. The system can be used to aid in stapling, transecting, resecting, sealing, grasping and/or inserting a medical device into tissue. Additionally, the system can be used for treatment of tumors, fibroids, cysts, damaged blood vessels, or other damages to internal structures of a patient. The system can be used during open surgery, laparoscopic surgery, endoscopic procedures, robotic surgeries, biopsies, and/or interventional radiology procedures.

The system can be used in conjunction with live intraoperative ultrasound (U/S), pre-operative CT, or any cross-sectional medical imaging modality (for example MRI, OCT, etc.). In addition, the system can use a variety of techniques to determine the position and/or orientation of one or more medical devices. For example, the system can use the NDI Aurora magnetic system, NDI Polaris optical system, etc. In some embodiments, a position sensor can be embedded inside or affixed to each medical device, for example, at the tip, along the shaft, and/or on the handle. Sensors can be built into the medical devices or attached after manufacturing, as described in greater detail in U.S. application Ser. No. 14/212,184, filed Mar. 14, 2014, entitled "Sensor Mount," which is hereby incorporated herein in its entirety.

Each medical device can be associated with one or more sensors, which can continually, or repeatedly, report position and/or orientation, or a single sensor can be used for all the medical devices. In some embodiments, where one sensor is used, the healthcare provider can attach the sensor to the particular medical device that she is intentionally repositioning, and then, once she has placed that medical device, she can remove the sensor and attach it to the next medical device she is repositioning. In some embodiments, the medical devices can be manipulated by the healthcare provider. In certain embodiments, the system can be used with a robotic manipulator, where the robot controls the medical devices. In some embodiments, visually-detectable fiducials can be used to determine or correct position and/or orientation for one or more of the medical devices.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator.

Image Guidance Systems

FIG. 1A is a diagram illustrating an embodiment of an image guidance system 100 for image management in image-guided medical procedures. As illustrated, the system 100 can include, but is not limited to, a position sensing unit 130, one or more medical devices 140 or 145, an image guidance unit 150, an imaging unit 160, a display 170, a surgical or therapeutic system 180, a stand 172, or a surgical table 174. Any of the position sensing unit 130, image guidance unit 150, one or more medical devices 140 or 145, imaging unit 160, display 170, or surgical system 180 can be communicatively coupled to each other, including one-to-one, one-to-many, and many-to-many relationships.

The position sensing unit 130 can be configured to track medical devices 140 or 145 within a tracking area and can be used to determine an emplacement or pose of medical devices 140 or 145. The term emplacement as used herein is a broad term and may refer to, without limitation, position and/or orientation or any other appropriate location information. Similarly, the term pose as used herein is a broad term encompassing its plain and ordinary meaning and may refer to, without limitation, position and/or orientation or any other appropriate location information. In some cases, one or more reference room coordinate systems (as described herein with reference to FIG. 1B), can be tracked by the position sensing unit 130, and an emplacement of the surgical devices 140 or 145 can be determined with respect to the reference room coordinate system. The position sensing unit 130 can provide emplacement data to the image guidance unit 150.

The position sensing unit 130 can be implemented using one or more of various techniques. For example, a tracking unit can be mounted, affixed, or coupled in or on one or more medical devices 140 and 145, and the position sensing unit 130 can track the tracking units. In addition or alternatively, a position sensing unit 130 can be implemented as a tracking unit, and can be attached or affixed to either or both of the medical devices 140 and 145. The position sensing unit 130 can include one or more sensing devices (such as the HiBall tracking system, a GPS device, or signal emitting device) that allow for tracking of the emplacement of a tracking unit. The term tracking unit (also referred to as an emplacement sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed herein. For example, FIG. 1A illustrates an example optical tracking unit 135, mounted on the display 170.

For example, the position sensing unit 130 can include a magnetic tracker, and tracking units, which can include one or more magnetic coils, can be mounted in or on, or coupled to the medical devices 140 and 145. The position sensing unit 130 can include an electromagnetic measurement system (for example, an NDI Aurora system) that uses sensor coils for tracking units attached to the first or second surgical devices 140 and 145.

In some implementations, the tracking units can be implemented using optical position sensing devices, such as the HiBall tracking system, and the position sensing unit 130 can form part of the HiBall tracking system. For example, the position sensing unit 130 can include an optical 3D tracking system using fiducials. One or more visually-detectable fiducials can be coupled to or otherwise associated with the medical devices 140 or 145. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In addition or alternatively, the system can utilize one or more camera-based marker (or markerless) tracking systems or algorithms such as ArUco, AR Toolkit, Vuforia, Wikitude, SLAM, or the like.

Tracking units can additionally or alternatively include a GPS device or signal emitting device that allows for tracking of the emplacement of the tracking unit. In some embodiments, a signal emitting device might include a radio-frequency identifier (RFID). In such embodiments, the position sensing unit 130 can use the GPS coordinates of the tracking units or can, for example, triangulate the radio frequency signal being emitted by the RFID associated with tracking units. The tracking systems can also include one or more 3D mice.

In some implementations, the position sensing unit 130 can include an inertial 3D tracking system that includes a compass, accelerometer, tilt sensor, or gyro, such as the InterSense InertiaCube or a Nintendo Wii controller. For example, devices 140 and 145 can include or have coupled thereto one or more accelerometers, which can be used to estimate movement, position, or location of the devices. In some embodiments, the position sensing unit 130 can be an Ascension Flock of Birds, Nest of Birds, driveBAY, medSAFE, trakSTAR, miniBIRD, MotionSTAR, pciBIRD, or Calypso 2D Localization System and tracking units attached to the first or second medical devices 140 and 145 can be magnetic tracking coils.

The position sensing unit 130 can be located in various locations, such as on, beside, above, or below the table 174 or patient 176. For example, in embodiments where the position sensing unit 130 is a magnetic tracker, the position sensing unit 130 can be mounted on or below the table 174. Such an arrangement can be useful when the tracking volume of the position sensing unit 130 is dependent on the location of the position sensing unit 130, as with many magnetic trackers.

The medical devices 140 or 145 can include invasive medical devices that enter a part of the body. For example, the medical devices 140 and 145 can include, but are not limited to, one or more of a grasper, a stapler, a vessel sealer, an electrocautery device, a resecting device, a transecting device, a scalpel, a biopsy needle, an ablation needle, a surgical needle, a nerve-block needle, another needle, a catheter, a stent, a laparoscope or laparoscopic camera, implantable hardware, an ultrasound probe (for example, laparoscopic ultrasound probes that enter the patient, Transesophageal echocardiography (TEE), or an ultrasound transducer on the tip of a catheter, needle, or other medical device), or another invasive instrument. In addition or alternatively, the medical devices 140 and 145 can include one or more non-invasive medical devices that, in some cases, might not enter the body. For example, medical devices 140 or 145 can include, but are not limited to, one or more of an ultrasound transducer, ultrasound probe, or other external imaging device. The medical devices 140 and 145 include medical imaging devices that provide or aid in the selection of medical images for display.

Image guidance unit 150 can be used to produce images 125 that are displayed on display 170. For example, the image guidance unit 150 can receive, process, or combine emplacement data from the position sensing unit 130, information about and from multiple surgical systems 180, information about and from attached medical devices 140, 145 (and additional medical devices not shown), or other data and can cause the display 170 to display image guidance data. A healthcare provider can use this image guidance data to guide a procedure and improve patient care. The image guidance data can include one or more display objects or one or more image guidance cues. It will be understood that a display object as used herein is a broad term encompassing, without limitation, one or more portions of a virtual medical device or a medical image. Further, an image guidance cue can include one or more trajectory indicators, intersection indicators, plane indicators, or other data.

The medical image can include or be associated with imaging data obtained from one or both of medical devices 140 and 145, or one or more additional medical devices. For example, the medical image can include data from modalities such as a CT scan, MRI, open-magnet MRI, optical coherence tomography ("OCT"), positron emission tomography ("PET") scans, fluoroscopy, ultrasound, or other preoperative or intraoperative 2D or 3D anatomical imaging data.

The image guidance data, such as one or more display objects or image guidance cues, can be displayed concurrently or simultaneously. Reference to displaying objects "concurrently" or "simultaneously" is to be interpreted broadly and may refer to displaying objects in such a way that to a human observer the objects are visible at the same time.

In some cases, the system can include imaging unit 160, which can be an imaging unit that is additional or alternative to image guidance unit 150. For example, imaging unit 160 can be used to produce images that are displayed on a second display (not shown). For example, the imaging unit 160 can receive or process medical imaging data received from an imaging device. As a non-limiting example, the imaging unit 160 can be an ultrasound machine, and the second display can be a display associated with the ultrasound machine 160 that displays medical images obtained by the ultrasound machine 160. In addition, the medical device 145 can be implemented as a movable imaging device, such as an ultrasound transducer or ultrasound probe. In such examples, the movable imaging unit 145 can be connected to image guidance unit 150 or the imaging unit 160, and can be useful for allowing a user to indicate what portions of a first set of imaging data are to be displayed. For example, the movable imaging unit 145 can be an ultrasound transducer 145 or other medical device, and can be used by a user to indicate what portions of imaging data, such as a preoperative CT scan, to show on a display 170 as image 125. The image guidance data displayed on display 170 and the imaging data displayed on the second display can be the same or different. In addition, the position sensing unit 130 can be part of any of the image guidance unit 150 or the imaging unit 160, or it can be separate.

The images 125 can be produced on the display 170 by the image guidance unit 150. The display 170 or screen can be implemented using a TV, computer screen, head-mounted display, projector, or the like. In the illustrated embodiment, the images 125 include a 2D viewing area 120 and a 3D viewing area 110. In the 2D viewing area 120, some image guidance data can be displayed as 2D objects. For instance, the 2D viewing area can include a 2D view of a medical image 122 (for example, an ultrasound slice), a 2D view of a medical device 124 (for example, a needle) intersecting the image plane, or one or more image guidance cues. It will be understood that some or all of the display objects in the 2D viewing area can be displayed as 3D objects.

In the 3D viewing area 110, at least some image guidance data can be displayed as 3D objects. For example, the 3D viewing area 110 can include a perspective view of each of the medical image 104, a first virtual medical device 102 corresponding to the first medical device 140, a second virtual medical device 106 corresponding to the second medical device 145, one or more trajectory guidance cues 108, a patient orientation indicator 112, or other image guidance data. It will be understood that any combination of the image guidance data can be displayed in the 2D view or 3D view as desired.

As a non-limiting example, if the first medical device 140 includes a needle and the second medical device 145 includes an ultrasound probe 145, then images 125 produced on display 170 can include images, or video, from the ultrasound probe, combined with display objects (such as virtual medical device 102 or 106) or image guidance cues (such as trajectory indicator 108). In addition or alternatively, if the first medical device 140 includes an ultrasound probe 140 and the second medical device 145 includes a laparoscopic camera 145, then images 125 produced on display 170 can include the video from the laparoscopic camera 145 combined with ultrasound data superimposed on the laparoscopic image. The system can additionally or alternatively process or display collected data, such as preoperative CT scans, X-Rays, MRIs, laser scanned 3D surfaces etc.

As noted above, images 125 can be generated based on live, intraoperative, or real-time data obtained using medical device 145, which can be coupled to imaging unit 160. The term real-time as used herein is a broad term and has its ordinary and customary meaning, including without limitation instantaneously or nearly instantaneously. The use of the term real-time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

In some embodiments, the display 170 displays 3D images to a user, such as a healthcare provider. Stereoscopic 3D displays separate the imagery shown to each of the user's eyes. This can be accomplished by a stereoscopic display, a lenticular auto-stereoscopic display, a head-mounted display, or any other appropriate type of display. The display 170 can be an alternating row or alternating column display. Example alternating row displays include the Miracube G240S, as well as Zalman Trimon Monitors. Alternating column displays include devices manufactured by Sharp, as well as many "auto-stereoscopic" displays (for example, Philips). In some embodiments, Sony Panasonic 3D passive displays and LG, Samsung, or Vizio 3D TVs can be used as well. Display 170 can also be a cathode ray tube. Cathode Ray Tube (CRT) based devices, can use temporal sequencing, showing imagery for the left and right eye in temporal sequential alternation. This method can also be used for projection-based devices, as well as by liquid crystal display (LCD) devices, light emitting diode (LED) devices, or organic LED (OLED) devices.

In certain embodiments, the display 170 can be a head-mounted display worn by the user in order to receive 3D images from the image guidance unit 150. In such embodiments, a separate display, such as the pictured display 170, can be omitted. The 3D graphics can be produced using underlying data models, stored in the image guidance unit 150 and projected onto one or more 2D planes in order to create left and right eye images for a head mount, lenticular, or other 3D display. The underlying 3D model can be updated based on the relative emplacements of the various devices 140 and 145, as determined by the position sensing unit(s) 130, or based on new data associated with the devices 140 and 145. For example, if the second medical device 145 is an ultrasound probe, then the underlying data model can be updated to reflect the most recent medical image. If the first medical device 140 is a stapler, then the underlying model can be updated to reflect any changes related to the jaws, such as information regarding the likely affected anatomy region or angles of the jaws or transecting knife. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

Images 125 can be produced based on intraoperative or real-time data obtained using first medical device 140, which can be coupled to a surgical system 180. In the illustrated embodiment of FIG. 1A, the surgical system 180 is shown as coupled to image guidance unit 150. The coupling between the first surgical system 180 and image guidance unit 150 may not be present in all embodiments. In some embodiments, the coupling between first surgical system 180 and image guidance unit 150 can be included where information about first medical device 140 available to first surgical system 180 is useful for the processing performed by image guidance unit 150. For example, in some embodiments, it can be useful to send one or more operating parameters of the medical device 140 to image guidance unit 150 so that image guidance unit 150 can show, highlight, outline or otherwise present an affected region of tissue which is located around a tip of the medical device. In other embodiments, the surgical system 180 is not coupled to the image guidance unit 150. Example embodiments including images and graphics that can be displayed are included below.

One or more components, units, devices, or elements of various embodiments can be packaged or distributed as part of a kit. For example, in one embodiment, a medical device, one or more tracking units, 3D viewing glasses, or a portion of an ultrasound wand can form a kit. Other embodiments can have different elements or combinations of elements grouped or packaged together. Kits can be combined or distributed separately from or with the other portions of the system.

Although two medical devices (devices 140 and 145) are shown in FIG. 1, it will be understood that additional or fewer medical devices can be included in the system 100. For example, additional or fewer medical devices can be tracked and associated data can be provided to the image guidance unit 150.

There are numerous other possible embodiments of system 100. For example, many of the depicted components can be joined together to form a single component and can be implemented in a single computer or machine. Further, additional position sensing units can be used in conjunction with position sensing unit 130 to track all relevant medical devices 140 and 145, as discussed in more detail below. Additional imaging units 160 can be included, and combined imaging data from the multiple imaging units 160 can be processed by image guidance unit 150 and shown on display 170. Additionally, two or more surgical systems 180 can also be included. Additionally, one will readily recognize that there are numerous other examples of image guidance systems which can use, incorporate, support, or provide for the techniques, methods, processes, and systems described herein.

Coordinate Systems

Figure 1B:
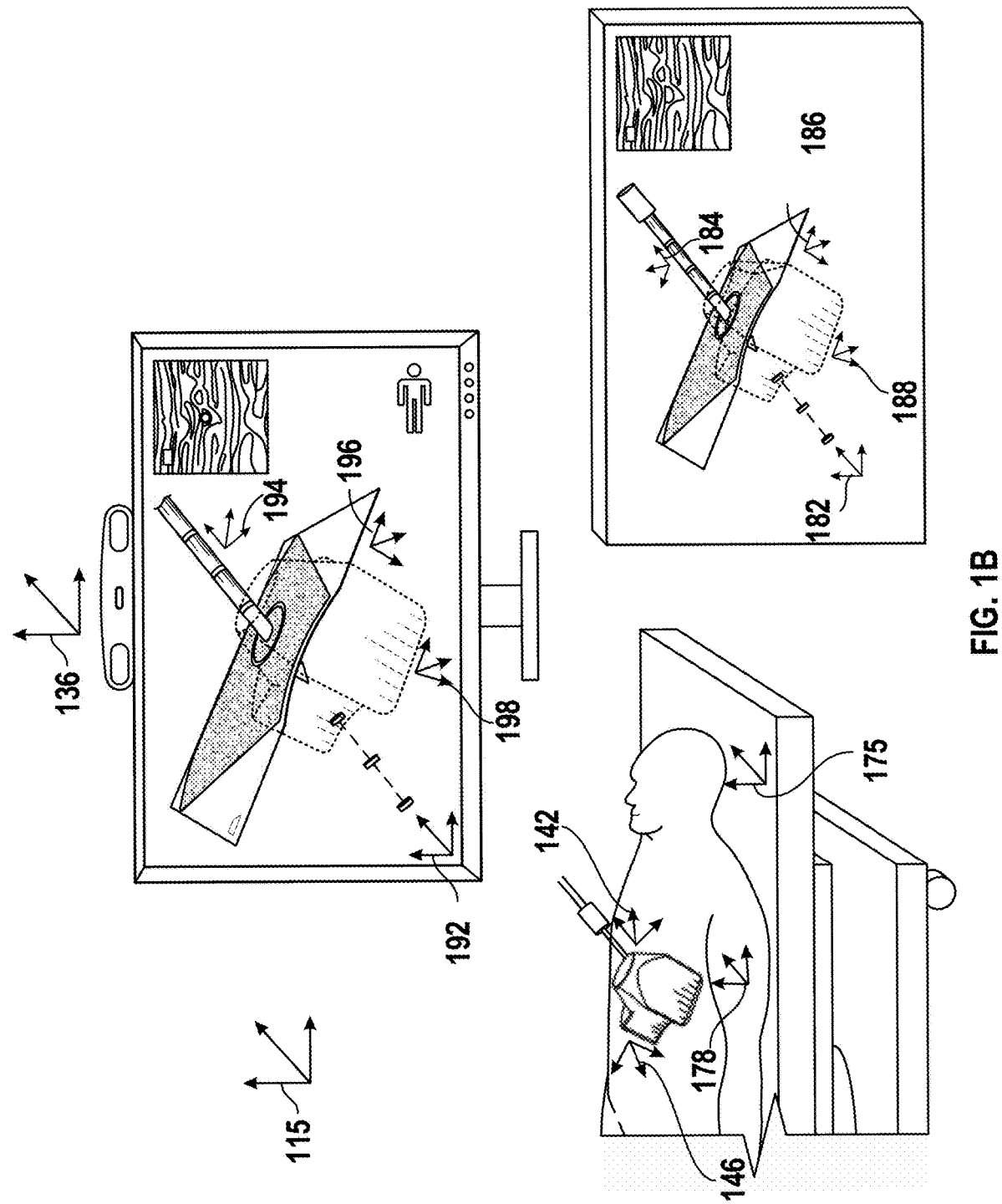
FIG. 1B is a diagram illustrating embodiments of coordinate systems that can be used by the system.

FIG. 1B is a diagram illustrating embodiments of coordinate systems that can be used by the system 100. The system 100 can utilize one or more coordinate systems to track and display the various image guidance data on the display 170. In some cases, one or more coordinate systems can be associated with real objects. For example, the coordinate systems can include a table 174 coordinate system 175, a first medical device 140 coordinate system 142, a second medical device 145 coordinate system 146, a patient 176 coordinate system 178, or a room coordinate system 115. In some cases, one or more coordinate systems can be associated with virtual or other objects. For example, the coordinate systems can include a 3D scene coordinate system 182, a first virtual medical device coordinate system 184, a second virtual medical device coordinate system 188, or a medical image coordinate system 186. In addition or alternatively, the coordinate systems can include a display coordinate system 192, or corresponding display coordinate systems 194, 196, or 198 for the first or second virtual medical device or medical image.

As a non-limiting example, the position sensing unit 130 can determine an emplacement of one or more real objects (for example, first medical device 140, second medical device 145, or the like) relative to one or more of the coordinate systems. For example, in some embodiments, an emplacement can be determined relative to the table coordinate system 175, which can be used by a magnetic tracker (not shown) tracking objects within a magnetic field volume, or to the optical tracker 135 coordinate system 136, which can be used by an optical tracker 135 to track one or more objects.

In some cases, multiple coordinate systems can be utilized together. For example, a magnetic position sensing coordinate system 175 can be used in conjunction with magnetic tracker tracking sensor coils within a position sensing region that are coupled to medical devices and an optical position sensing coordinate system 136 can be used in conjunction with an optical tracker 135 tracking a fiducial coupled to a head mounted display (HMD) or a user, or to an optical tracker analyzing an image captured by an image sensor. It will be understood that any combination of the tracker systems or coordinate systems can be used as desired. For example, the position sensing unit 130 can utilize the same coordinate system to track the tracking sensors associated with each of the one or more medical devices or tracking sensors associated with a user or HMD. Alternatively, a coordinate system, such as coordinate systems 142 and 146, can be used for each tracking sensor, or any combination thereof.

Room coordinate system 115 can be used to determine the emplacement of objects within a room, such as an operating room. For example, the room coordinate system 115 can be used to determine or identify the relative emplacement of the position sensing unit 130, medical devices 140, 145, tracking sensors, user, display 170, etc. relative to each other within a room.

A 3D scene coordinate system 182, which may also be referred to as a 3D volume or scene graph coordinate system, can be used to determine the emplacement of display objects within a virtual 3D scene. In some cases, the 3D scene coordinate system 182 can identify the relative emplacement of virtual objects within the 3D scene. In certain embodiments, the virtual objects can correspond to real objects, such as to medical devices 140, 145 or to computer-generated objects, such as such as trajectory cues 108. In certain embodiments, display objects can correspond to real objects, virtual objects, or computer generated objects. In addition or alternatively, the 3D scene coordinate system 182 can be used to determine an emplacement of, register an emplacement of, or model one, multiple, or all of the objects in the room, such as the patient, the operating table, the physician, the display, or the like. In some cases, the display 170 can display a subset of the data associated with the 3D scene coordinate system 182. In some cases, one or more portions of the image guidance data can have an associated coordinate system.

A display coordinate system 192 can be used to determine the emplacement of display objects for display on the display 170. For example, the display coordinate system 192 can be used to determine the emplacement of virtual medical devices, medical images, image guidance cues, or the like, within a display 170. In some embodiments, the display coordinate system 192 can be used to determine how the objects within the 3D scene are to be displayed on the display. For example, the display coordinate system 192 can be used to determine a point-of-view location, or eye point, relative to the 3D scene (or 3D volume coordinate system 182) or scene graph for viewing the contents of the 3D scene. As mentioned above, multiple display coordinate systems 192 can be used. For example, left-eye, right-eye, or center-eye display coordinate systems can be used to display different perspective of the display objects within a 3D scene, such as when a 3D display or a head-mounted display (HMD) is being used.

A medical image coordinate system 196 can be used in conjunction with medical images used or processed by the system. As described previously, the medical images can be ultrasound images, CT image, MRI, images, etc. The images can be different sizes or shapes. For example, one ultrasound can output an image having one size and shape while a different ultrasound can output an image having a different size or shape. Similarly, CT, MRI, and ultrasound images may have different sizes and shapes. Accordingly, the medical image coordinate system 196 can be used to identify the particular size and shape of the medical image being used or processed by the system 100.

It will be understood that fewer, more, or different coordinate systems can be used as desired. For example, in some embodiments, the 3D scene coordinate system 182 can be omitted or combined with display coordinate system 192 or the table coordinate system 175. Furthermore, in some cases, one or more tracking sensor coordinate systems, medical device coordinate systems 146, 142, virtual medical device coordinate systems 184, 194, 188, 198, or other objects etc., can have their own coordinate system. The coordinate systems for the tracking sensors, medical devices, or virtual medical devices can be used to identify the dimensions of the sensor/device/display object and relationship of the sensor/device/display object to another sensor/device/display object or other coordinate systems. For example, a medical device coordinate system (or virtual medical device coordinate system) can identify the dimensions of a corresponding medical device or virtual medical device, as well as the emplacement of a tracking sensor relative to the medical device (or vice versa). Similarly, a medical imaging device coordinate system can identify the dimensions of the corresponding medical imaging device (or virtual medical imaging device) or an emplacement of a medical imaging device relative to the medical imaging device (non-limiting example: the emplacement of an ultrasound image relative to the corresponding ultrasound transducer), or vice versa. The system 100 can use various coordinate systems to determine the emplacement of a portion or the entire object with respect to each other and with respect to the other coordinate systems.

The system 100 can use the various coordinate systems to determine emplacement of objects relative to each other and determine how to display the display objects on a display, such as the display 170.

As a non-limiting example, the second medical device 145 can include an ultrasound transducer. To display a virtual rendering 106 of an ultrasound transducer 145 and a virtual rendering 104 of an ultrasound image on the display 170, the system 100 can determine the emplacement of a magnetic tracking sensor coupled to the ultrasound transducer 145 within a magnetic position sensing coordinate system 175. Using a magnetic tracking sensor coordinate system 175, the system 100 can determine the location of each portion of the magnetic tracking sensor within the magnetic position sensing coordinate system 175. The system 100 can also determine the emplacement of each portion the ultrasound transducer 145 within the magnetic position sensing coordinate system by mapping the ultrasound transducer coordinate system 146 to the magnetic tracking sensor coordinate system 175 (or vice versa).

In addition, the system 100 can map each portion of the ultrasound image corresponding to the ultrasound transducer 145 to the magnetic position sensing coordinate system 175 by mapping an ultrasound image coordinate system to the ultrasound transducer coordinate system 146 or the magnetic tracking sensor coordinate system 175.

To display the virtual ultrasound transducer 106 and virtual ultrasound image slice 104, the system 100 can map the various objects from the magnetic position sensing coordinate system 175 to a room coordinate system 115, which can identify the relative emplacement of the coordinate system 175 to a display 170. The system can then map data to the 3D scene coordinate system 182 or the display coordinate system 192. For 3D viewing, the system 100 can map the objects to multiple display coordinate systems 192, such as left-eye or right-eye coordinate systems.

With continued reference to the non-limiting example, the system 100 can determine an emplacement of an optical tracking sensor corresponding to a user within an optical position sensing coordinate system 136. The emplacement of the optical tracking sensor within the optical position sensing coordinate system 136 can be mapped to the room coordinate system 115, the 3D scene coordinate system 182, or the display coordinate systems 192 for display. In this way the system 100 can determine the emplacement of the ultrasound transducer 145 and ultrasound image slice relative to the user and display a virtual rendering 106 of the ultrasound transducer and a virtual rendering 104 of the ultrasound image slice within the 3D scene relative to the determined emplacement of a user.

To display the virtual ultrasound transducer 106 and virtual ultrasound image slice 104, the system 100 can map the various objects from the magnetic position sensing coordinate system 175 to a room coordinate system 115, which can identify the relative emplacement of the coordinate system 175 to a display 170. The system can then map data to the 3D scene coordinate system 182 or the display coordinate system 192. For 3D viewing, the system 100 can map the objects to multiple display coordinate systems, such as left-eye or right-eye coordinate systems.

Although the non-limiting examples have been described as mapping the various objects and coordinate systems, to a coordinate system 175, the room coordinate system 115, the 3D scene coordinate system 184, or to display coordinate systems 192, it will be understood that one or more of the objects or coordinate systems can be mapped directly or indirectly to any other coordinate system. For example, the medical device image can be mapped directly to a left-eye display coordinate system, etc. Thus, any of the real or virtual objects described herein may be represented, detected, or imaged in any coordinate system, and conversion between the various coordinate systems can be performed in components of the system such as image guidance unit 150, position sensing unit 130, an HMD, or other components.

Furthermore, it will be understood that once the system 100 determines an emplacement of a medical device in one coordinate system, such as a coordinate system 175, the system 100 can determine the emplacement of a corresponding virtual medical device in a different coordinate system, such as the 3D scene coordinate system 182 or the display coordinate system 192, by mapping the coordinates of the first coordinate system to the coordinates of the second coordinate system, or vice versa. Accordingly, references made herein to determining an emplacement of the medical device can also refer to determining an emplacement of a virtual medical device corresponding to the medical device, or vice versa. Similarly, references made herein to determining an emplacement of a display object (non-limiting example: medical image) relative to the medical device can also refer to determining the emplacement of the display object relative to a corresponding virtual medical device.

Depicting Medical Devices

It can often be difficult to discern the content of a 3D scene from a 2D depiction of it, or even from a 3D depiction of it. Therefore, various embodiments herein provide image guidance that can help the healthcare provider better understand the scene and relative emplacements or poses of object in the scene, thereby providing improved image guidance.

Figure 2:
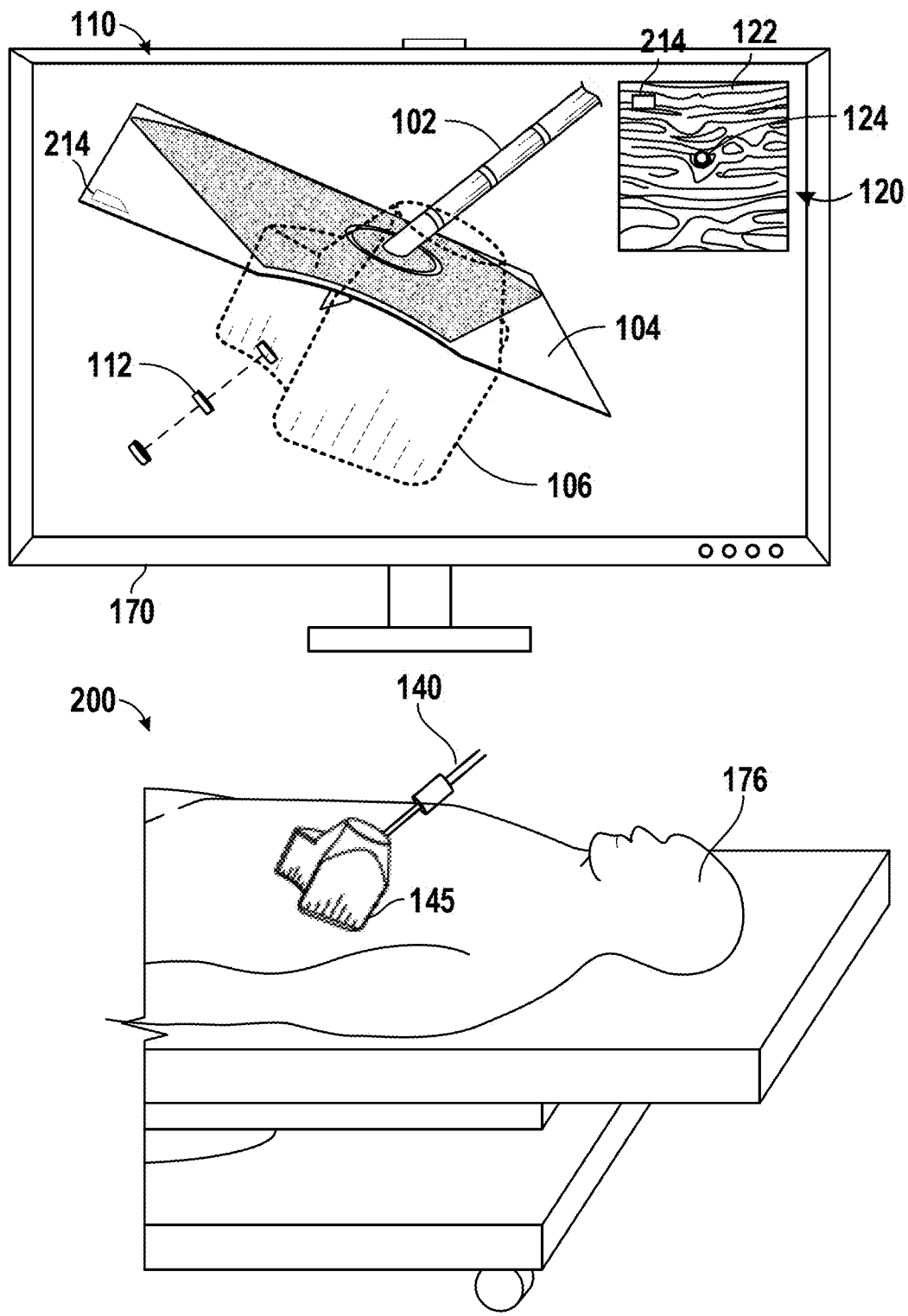
FIG. 2 illustrates an embodiment of a rendering of medical display objects on a display, as well as an embodiment of an environment for a medical device procedure.

FIG. 2 illustrates an embodiment of a rendering of medical display objects on a display 170, as well as an embodiment of an environment 200 for a medical device procedure. As illustrated, the environment 200 includes a patient 176, a first medical device 140, and a second medical device 145.

As described herein, image guidance data (for example, display objects 102, 104, or 106, and image guidance cues 112) displayed in the 3D scene 110 can correspond to one or more real-world objects of the surgical environment 200. For example, display object 102 can correspond to the first medical device 140, display object 106 can correspond to the second medical device 145, and display object 104 can correspond to a medical image associated with the second medical device 145.

In some cases, the display 170 can display the 3D scene 110 as if the surgical environment 200 is observed from a particular point-of-view location or viewpoint. The point-of-view location can refer to the location from which a virtual 3D space is viewed and can be any location as desired. In other words, if the display 170 is considered a window into the virtual 3D space, the point-of-view location can be the location of the window with respect to the objects in the virtual 3D space.

In some embodiments, as described in greater detail in U.S. patent application Ser. No. 14/212,933, filed Mar. 14, 2014, entitled MEDICAL DEVICE GUIDANCE (the '933 Application), incorporated herein by reference in its entirety, the point-of-view location can be a fixed location, such as in front of the display, a predetermined distance/angle from the screen 220 or stand 170, or a location configured by the user. Alternatively, the point-of-view location can be dynamic. For example, point-of-view location can be based at least in part on an emplacement of a real-world object, such as a medical device, the position sensing unit, or a head-mounted display, or the point-of-view location can be based on an actual, expected, or desired location of a user. For example, the system can track a user in real-time and determine the point-of-view location based at least in part on the tracked location of the user.

One or more of the display objects in the 3D scene 110 can be implemented as a virtual medical device (sometimes referred to as an avatar). For example, a virtual medical device displayed in display 170 can resemble the real medical device to which it corresponds. Some models of medical devices have markings such as bands around the shaft to indicate distance along the shaft. Healthcare providers performing medical device procedures are often familiar with these markings and can use them to help understand the spatial relationship between the medical device and anatomy. The make and model of a medical device can be known to the image guidance system 100, and a virtual medical device displayed in display 170 can resemble the real medical device to which it corresponds. For example, the virtual medical device 102 can resemble the real medical device 140. Similarly, the virtual medical device 106 can resemble the real medical device 145. Accordingly, it will be understood that the terms medical device and virtual medical device can sometimes be used interchangeably, as they can generally relate to the same object. That is, the medical device relates to the object in the real world and virtual medical device relates to a representation of the object, such as an avatar, in virtual space.

By displaying a virtual medical device that resembles a real medical device, the system can advantageously aid healthcare providers in associating the image guidance data with the real world. Furthermore, the more the healthcare provider is familiar with the guidance information, the more he or she is aided in the guidance task. For example, the healthcare provider can see the familiar markings on the medical device 102 being displayed on the display 170 and therefore be familiar with the distance and relative placement of the displayed medical device 102 with respect to other data, such as tissue seen in the medical image 104. This knowledge of relative placement of items being displayed can help the healthcare provider move a real medical device into place.

The features of the real medical device that can be rendered in the 3D scene 110 (for example, as the virtual medical device) include, but are not limited to, the overall shape (for example, diameter, angles, cross sectional shape, curvature, etc.), color, distance markers, angle of the jaws, visuals or echogenic fiducial markers, the state of deployable elements such as tines, paddles, anchors, resection loops, stiffening or steerable sleeves, temperature, radiation, light or magnetic field sensors, lens, waveguides, fluid transfer channels, and the like. The type of medical device being used can be an input into the image guidance system 100. For example, it can be a user input to the system or can be determined by the system. For instance, the medical device type can be detected by a camera or other device, can be received as data from an attached medical device, such as surgical system 180 in FIG. 1, or the information can be received in any other appropriate manner. Alternatively, the type of medical device can be can be a system default.

Consider an embodiment in which the virtual medical device 102 in the display 170 is a virtual stapler depicting the portion of a stapler 140 that will perform the stapling. The displayed virtual medical device can include a joint member, a first limb member, a second limb member, or more limb members. In some cases, one or more coordinate systems can be assigned to each of the joint member, a first limb member, a second limb member, and any additional limb members. Further, the same or different tracking sensors or tracking methods can be applied to each. If the display 170 also includes ultrasound data, then the doctor can find the tissue she wishes to staple by moving the ultrasound probe 145 until she identifies the target tissue. In various embodiments, she will be able to see the displayed ultrasound data 104 and its location relative to the displayed medical device 102. She can then direct the medical device 140 until she sees, on display 170, that an effective region of operation of the virtual medical device 102 encompasses a region of the tissue likely to be stapled in the medical image. Thus, when she activates the stapler, she can have a higher degree of confidence that she will staple the target portion of the tissue.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (for example, a small bump) on one side of the transducing array. That mark can also be shown in the medical image on the scanner's display, to help the healthcare provider understand where the scanned anatomical structures shown on screen are located under the transducer, inside the patient.

As described herein, the image guidance data can be displayed in the virtual 3D space 110, with the screen 170 acting as a window into the virtual 3D space. Furthermore, the emplacement of a virtual medical device within the virtual 3D space 110 can match or correspond to the emplacement of a corresponding real medical device. For example, if the real medical device 140 is moved to the right with respect to a point-of-view location, the virtual medical device 102 can also move to the right in the display 170. Similarly, if the real medical device 140 is rotated or oriented such that its tip is pointing away from the point-of-view location, the virtual medical device 102 can likewise show the change in orientation. For example, the display 170 can show the tip of the virtual medical device 102 in the background and the other end of the virtual medical device 102 in the foreground, such that the tip of the virtual medical device 102 is pointing away from the screen 170. Similarly, emplacement of the second virtual medical device 106 or the medical image 104 within the virtual 3D space 110 can match or correspond to the emplacement of the second real medical device 145.

Once tracked and displayed, a healthcare provider is able to see image guidance data on display 170 that will allow her to know the relative pose, location, or emplacement of the tracked instrument(s) with respect to one another or with respect to imaging data and will be able to see, on display 170, the features of the instrument rendered in the scene.

With continued reference to FIG. 2, in some embodiments, the image guidance system can cause the display to concurrently display an additional 2D view 122 of the medical image, simultaneous to the 3D depiction 104, so that the medical image is always visible, regardless of the emplacement in which the healthcare provider holds the ultrasound transducer 145. The 2D view 122 of the medical data can be similar to what a healthcare provider is accustomed to seeing with traditional medical displays, such as ultrasound displays. This can be useful by presenting to the healthcare provider the imaging to which she is accustomed and allows a healthcare provider to see the medical data regardless of the then-current emplacement of the imaging device with respect to the user.

In some embodiments, the 2D view 122 of the medical image is depicted in the upper right corner of the display 170, although it can be placed in any location. In some embodiments, the guidance system can automatically or continually choose a corner in which to render the 2D view 122 of the medical image, for example, based on the position of the medical devices in the rendered scene. For example, in FIG. 2, the needle 140 can be held in the healthcare provider's right hand and the needle's shaft can be to the right of the 3D view of the medical image. In this example, the 2D view 202 of the medical image is in the upper right corner of display 170 so that it does not cover any of the 3D features of the 3D scene 110 and the 3D scene 110 does not cover any of the features of the 2D medical image 122. However, in some cases, to prevent the 2D view 122 from covering or overlapping with some of the image guidance data, the system can automatically move the 2D view 122 to a corner that would not otherwise be occupied by graphics or data.

The system can attempt to avoid having the 2D view 122 of the medical image quickly move among corners of the display in order to avoid overlapping with graphics and data in the display. For example, a function f can be used to determine which corner is most suitable for the 2D medical image to be drawn in. The inputs to f can include the locations, in the screen coordinate system, of the displayed medical device tip, the corners of the 3D view of the medical image, etc. In some embodiments, f's output for any given point in time is independent of f's output in the previous frames, which can cause the medical image to move among corners of the display rapidly. In some embodiments, the image guidance system will filter f's output over time. For example, the output of a filter g, for any given frame, could be the corner, which has been output by f the most number of times over the last n frames, possibly weighting the most recent values for f most heavily. The output of the filter g can be used to determine in which corner of display 170 to display the 2D medical image and the temporal filtering provided by g can allow the 2D view 122 of the medical image display to jump less frequently, moving more smoothly among the corners of the display 170.

In some embodiments, other appropriate virtual information or image guidance cues can be overlaid on the 2D view 122 of the medical image as well as the 3D view 204. Examples include: orientation indicator 214, a portion of the virtual medical device 124, an indication of the distance between the medical device's tip (for example, the tip of the first limb member or the tip of the second limb member) and the point in the plane of the medical image that is closest to the medical device tip, an affected area (for example, a cross section or outline of the affected region projected on the ultrasound slice), or intersection indicators (for example, a point, box, outline, etc.) indicating an intersection between one or more axes or trajectories of a display object and a plane-of-interest (for example, a medical image plane, a medical device plane, etc.).

In some embodiments, the image guidance system can display a symbolic 3D representation of an orientation mark 214 both next to the motion-tracked ultrasound slice 104 (for example, moving with the displayed ultrasound slice) and next to the 2D view 120 of the ultrasound slice 122. An example of this orientation mark is displayed in FIG. 2, where a small rectilinear volume 214 is shown both in proximity to the ultrasound slice displayed in the 3D view and the ultrasound slice displayed in a 2D view. In some embodiments, the orientation mark 214 corresponds to a feature, such as a physical marking, of the ultrasound probe. In some embodiments, the orientation mark 214 is displayed to provide assistance in associating the 3D view and the 2D view.

It will be understood that a medical image can correspond to image data received from an imaging device, such as an ultrasound transducer. In some embodiments, the image data can correspond to a cross-section of tissue having a certain thickness. In some instances, the imaging device can compact the image data, or treat the image data as 2D data, such that there is no perceived thickness. In certain embodiments, when the medical image is displayed in a 3D view, the system can treat the medical image as a 2D or quasi 2D object. In such embodiments, the system can cause the medical image to have little to no perceptible thickness. Accordingly, in certain embodiments, when the medical image is oriented orthogonally or perpendicularly with respect to the point-of-view location, the system can cause the display to display nothing or a line having a relatively small thickness, such as a few pixels, etc. In some cases, the number of pixels used to display the relatively small thickness of the medical image can be a function of the size of the display. For example, more pixels can be used for a larger display and fewer pixels can be used for a smaller display, etc.

Some embodiments can track and display other types of instruments and their features. For example, a healthcare provider may want to track one or more of a stapler, vessel sealer, grasper, scalpel, a biopsy, a cauterizer (including an electrocauterizer and Bovies), forceps, cutting loops on hysteroscopes, harmonic shears, lasers (including $CO_2$ lasers), etc. For example, in various embodiments, the following devices can be tracked and various aspects of their design displayed on display 170: Olympus™ OES Pro Hystero-Resectoscope, SonoSurg Ultrasonic Surgical System Olympus™ GF-UC 160 Endoscope Wallus™ Embryo Transfer Catheter AngioDynamics NanoKnife™, Vena-Cure™ laser, StarBurst, Uniblade, Habib™, Resector Bovie™ Electrodes, Covidien Evident™, Cool-Tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Furthermore, it will be understood that other image guidance cues can be generated and displayed on the display as described in greater detail in the '274 Application, previously incorporated herein by reference. For example, the system 100 can generate or display graphical indicators that help indicate the spatial relationship between a medical device and a medical image plane (for example, graphical image plane indicators) or other plane (for example, graphical plane indicators), indicators to indicate the relative positions of the medical device(s) and medical image(s), features of interest, annotations, plane indicators, plane intersection indicators, other graphical indicators, approximate medical device location indicators, etc. As described in greater detail above and in the '274 Application, the various image guidance cues can be generated based at least in part on the emplacement information of the medical devices used with the system 100.

Although two virtual medical devices 102, 106 are displayed, it will be understood that fewer or more medical devices can be tracked and displayed concurrently, or simultaneously, on screen 170, as described in greater detail in the '274 Application, previously incorporated by reference. In some instances, a virtual medical device can sometimes be referred to as virtual surgical instrument, surgical instrument, rendered surgical instrument, rendered medical device, avatar, rendered avatar, virtual avatar, or the like.

Opaque Display Object

As described herein, a 3D scene on a display 170 can include image guidance data, such as a first display object 102 and a second display object 106. In instances where the second display object 106 is opaque, if a portion of the second display object 106 overlaps or occludes a portion of the first display object 102 (for example, the portions are co-located on the display 170 or share one or more of the same display pixels), then a viewer of the display 170 may not be able to see the covered portion of the first display object 102. An example of this occlusion is illustrated in FIG. 3.

Figure 3:
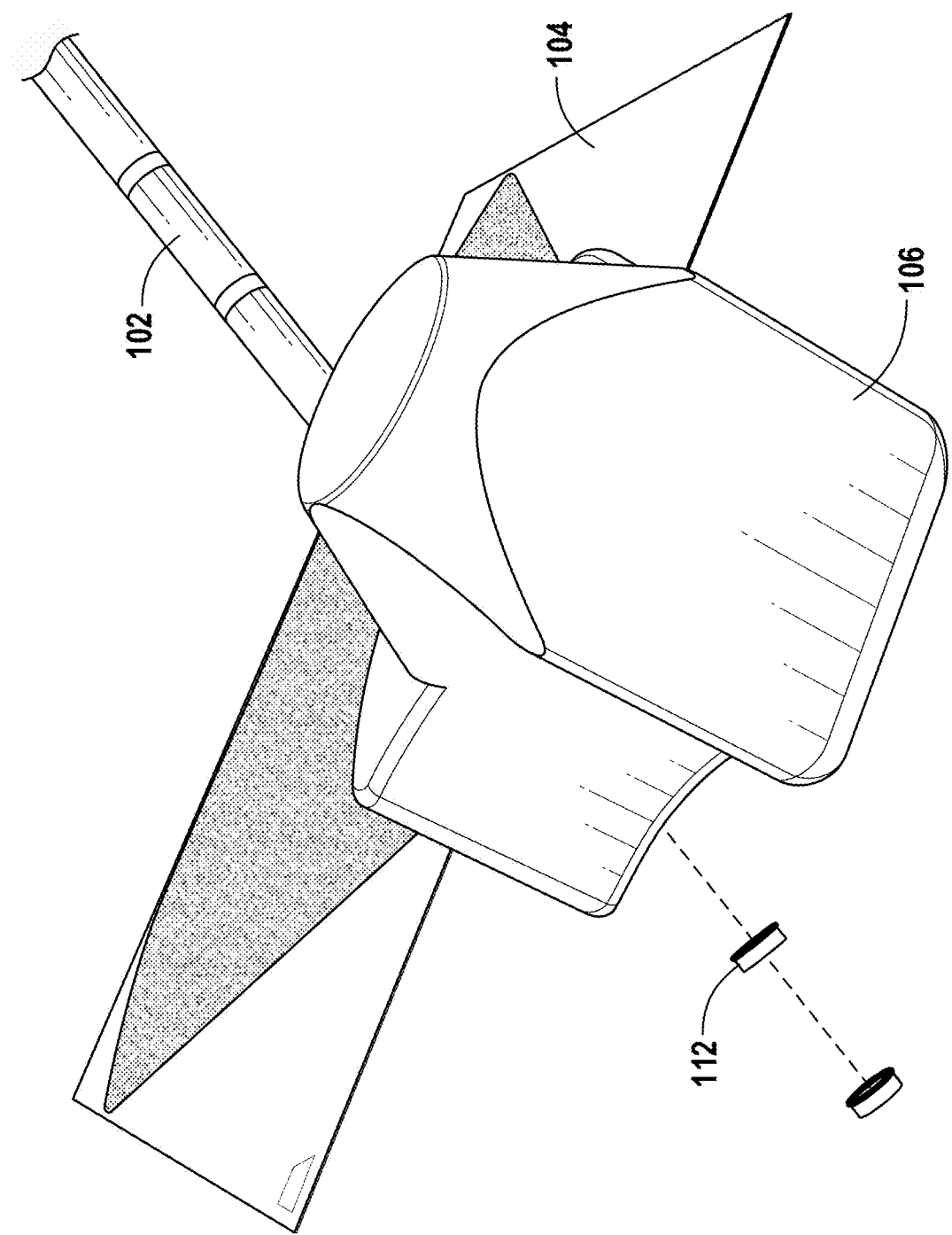
FIG. 3 is a diagram illustrating an embodiment of a rendering of imaging guidance data in a 3D scene.

FIG. 3 is a diagram illustrating an embodiment of a rendering of imaging guidance data in a 3D scene, including medical display objects 102, 104, 106 and image guidance cues 112. In this example, display object 102 is a first virtual medical device 102 that corresponds to a real medical needle, display object 106 is a second virtual medical device 106 that corresponds to a real ultrasound transducer, and display object 104 is a medical image that corresponds to imaging data obtained from the real ultrasound transducer.

In FIG. 3, the relationships between the virtual medical devices 102 and 106 and the medical image 104 can be described as the virtual ultrasound transducer 106 being in front of both the medical image 104 and the virtual needle 104 relative to a point-of-view location. In other words, the virtual ultrasound transducer 106 is closer to the point-of-view location than the medical image 104 and the virtual needle 104 are. In addition, the relationships between the virtual ultrasound transducer 106 and the image guidance cues 112 can be described as the virtual ultrasound transducer 106 being in front the image guidance cues 112.

However, in the illustrated example, the opaquely drawn virtual ultrasound transducer 106 occludes a portion of the medical image 104, as well as the virtual needle 102 and some of the image guidance cues 112. In addition, in FIG. 3 the virtual ultrasound transducer 106 blocks a user's view of how or where the virtual needle 102 interacts with the medical image 104. Thus, although the spatial relationships between the display objects can aid a user in placing the medical devices relative to each other, the opaque nature of the virtual ultrasound transducer 106 can make it difficult to view the interaction of the virtual medical device 102 with the medical image 104 and the corresponding patient tissue. This may make it more difficult for a physician to make a diagnosis, target the virtual needle 102, or administer treatment.

Beginning-Surface Rendering

Figure 4:
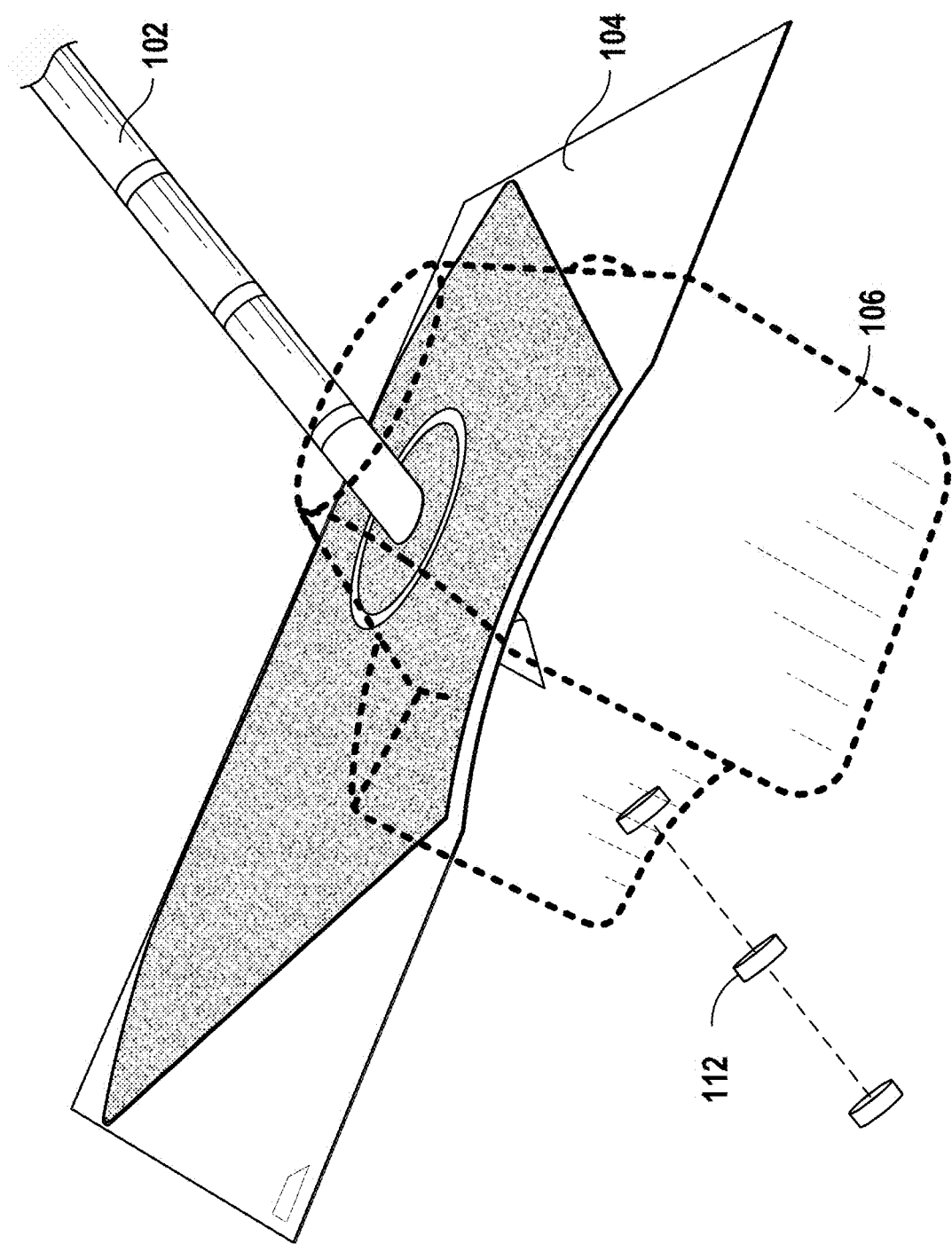
FIG. 4 is a diagram illustrating an embodiment of an example selective-transparency beginning-surface rendering of a virtual transducer.

FIG. 4 is a diagram illustrating an embodiment of a rendering of imaging guidance data. FIG. 4 illustrates the display objects 102, 104, 106 in the same or similar orientation as shown in FIG. 3. In addition, the transducer 106 is illustrated with a selective-transparency surface rendering where the selected surface is a beginning-surface. In the illustrated embodiment, the beginning-surface includes those surfaces, edges, or other portions of the display object that are facing the point-of-view location and that are not occluded from view by the object's shape. In some cases, the system can render only the beginning-surface of a display object, or can render the beginning-surface more opaquely than other portions of the display object. Imagine a plurality of imaginary view-rays extending from the point-of-view location to the object. The "beginning-surface" portion of that object can include the closest surfaces of the object along multiple or all of the view-rays. In other words, the beginning-surface can include an aggregation of the initial entry points (into the object) from multiple or all of the view-rays. Note that the beginning-surface portions of the transducer 106 in FIG. 4 include the same portions of the transducer 106 displayed in FIG. 3.

In the illustrated embodiment of FIG. 4, the selective-transparency beginning-surface rendering of the transducer 106 includes a display of the beginning-surface at varying transparency levels, with other portions of the transducer 106, such as the ending-surface, back-surface, interior, etc. being omitted, not shown, or completely transparent. Although in the illustrated embodiment of FIG. 4, only a beginning-surface is used for the selective-transparency rendering, it will be understood that multiple surfaces can be used as part of a selective-transparency rendering. For example, a selective-transparency surface rendering can include a beginning-surface, ending-surface, front-surface, rear-facing surface, side-facing surface, etc.

In the illustrated embodiment of FIG. 4, the selective-transparency of the beginning-surface is implemented with the beginning-surface becoming less transparent as it gets closer to an edge. In this way, the medical image 104, the virtual needle 102, and the image guidance cues 112 are each visible through the transducer 106, and the spatial relationships between each of the transducer 106, needle 102, medical image 104, and image guidance cues 112 can be seen. In some embodiments, the selective-transparency beginning-surface rendering of the transducer can reduce the number of displayed lines and improve a user's ability to properly understand the correct orientation of the transducer 106.

It will be understood that the selective-transparency of the selected surface can be implemented in a variety of ways. For example, the selective-transparency can include displaying the selected surface at the same transparency level, displaying edges of the surface opaquely or as solid or dashed lines (non-limiting example: wire frame) and the rest of the selected surface transparently or vice versa, displaying portions of the surface that are in front of another display object transparently or more transparently than portions of the selected surface that are not in front of another display object, etc.

Moreover, when a selective-transparency rendering includes multiple surfaces, each surface can be rendered using the same selective-transparency or different selective transparencies. For example, a beginning-surface can be rendered such that portions of the beginning-surface that are closer to an edge are rendered at a different opacity (for example, more or less opaquely) than portions that are farther away from an edge. As another example, an ending-surface can be rendered such that the entire surface has a single level of transparency or alternatively can be rendered such that only edges of the ending-surface are rendered opaquely, while other portions of the ending-surface are render with a diminished opacity or are completely transparent.

In addition or alternatively to a selective-transparency rendering of the transducer, the system can render one or more selected surfaces of one or more other display objects. For example, it can be advantageous for the physician to see at least the beginning-surface of every display object. Accordingly, in some cases, each display object (or portion of each display object) that is in front of another display object (with respect to the point-of-view location) can be rendered with a selective-transparency beginning-surface rendering. For instance, referring to the illustrated embodiment of FIG. 4, a portion of the virtual needle 102 overlaps with a portion of the medical image 104. In some cases, at least one of the beginning-surfaces of the virtual needle 102 or the medical image 104 can be displayed using a selective-transparency beginning-surface rendering such that each beginning-surface portion of every display object is visible to the physician. Furthermore, in some embodiments, all display objects, or a subset thereof, can be displayed using a selective-transparency rendering.

Furthermore, as described herein, the selected surfaces can be rendered selectively transparent in a variety of ways. For example, the system can render portions of the selected surface of a display object that overlap with other display objects transparently or more transparently than non-overlapping portions of the display object, which can be rendered opaquely (for example, like the transducer 106 as illustrated in FIG. 3). In certain embodiments, the non-overlapping portions of the display object can be displayed at one or more different transparency levels similar to the overlapping portions of the selected surface. In some cases, if more than two display objects (or other image guidance data) are overlapping at the same location (for example, the same pixel on the display 170), then two or more of the overlapping display objects or portions thereof can be displayed using a selective-transparency rendering. For example, the closest display object or portion thereof (relative to the point-of-view location) can be displayed using a selective-transparency beginning-surface rendering. In addition, the second closest display object or portion thereof (relative to the point-of-view location) can be displayed using a selective-transparency beginning-surface rendering. In some cases, the selective-transparency of the first and second objects can be different. For example, the second object can use a different selective-transparency scheme, such as more transparent or a uniform transparency level. Rendering the multiple beginning-surface renderings at different transparency levels can allow each overlapping portion to be visible to the physician, and can allow the physician to understand the spatial relationships between each display object, or other image guidance data.

Although only the edges of the beginning-surface of the virtual ultrasound transducer 106 are clearly depicted in FIG. 4 (for example, for stylistic reasons due to the constraints of black/white illustration), it should be noted that other portions of the beginning-surface may be displayed, such as the continuous portions between the edges. In some embodiments, the rendering of the transducer 106 can include shading and other visualization techniques to illustrate contours of the transducer 106. For example, in some cases, surface shading can be added to the beginning-surface rendering of the virtual ultrasound transducer 106, which can make the virtual ultrasound transducer 106 more salient and easier to see, despite its transparency.

As described above, in some cases, rendering the selective-transparency beginning-surface rendering of the transducer 106 can include omitting, ignoring, rendering transparently or otherwise not showing portions of the transducer 106 that are not part of the beginning-surface. For example, portions that are not part of the beginning-surface can include the ending-surfaces (described in more detail below), the back-surface, the interior, one or more sides, or the like. As a non-limiting example, to render the selective-transparency beginning-surface rendering of the transducer 106, the system can determine the beginning-surface of the transducer and can determine the portions of the transducer that are not included in the beginning-surface. In some cases, the system can display the selective-transparency beginning-surface rendering of the transducer 106 and can discard, omit, or display transparently the portions of the transducer that are not included in the beginning-surface.

Ending-Surface Rendering

Figure 5:
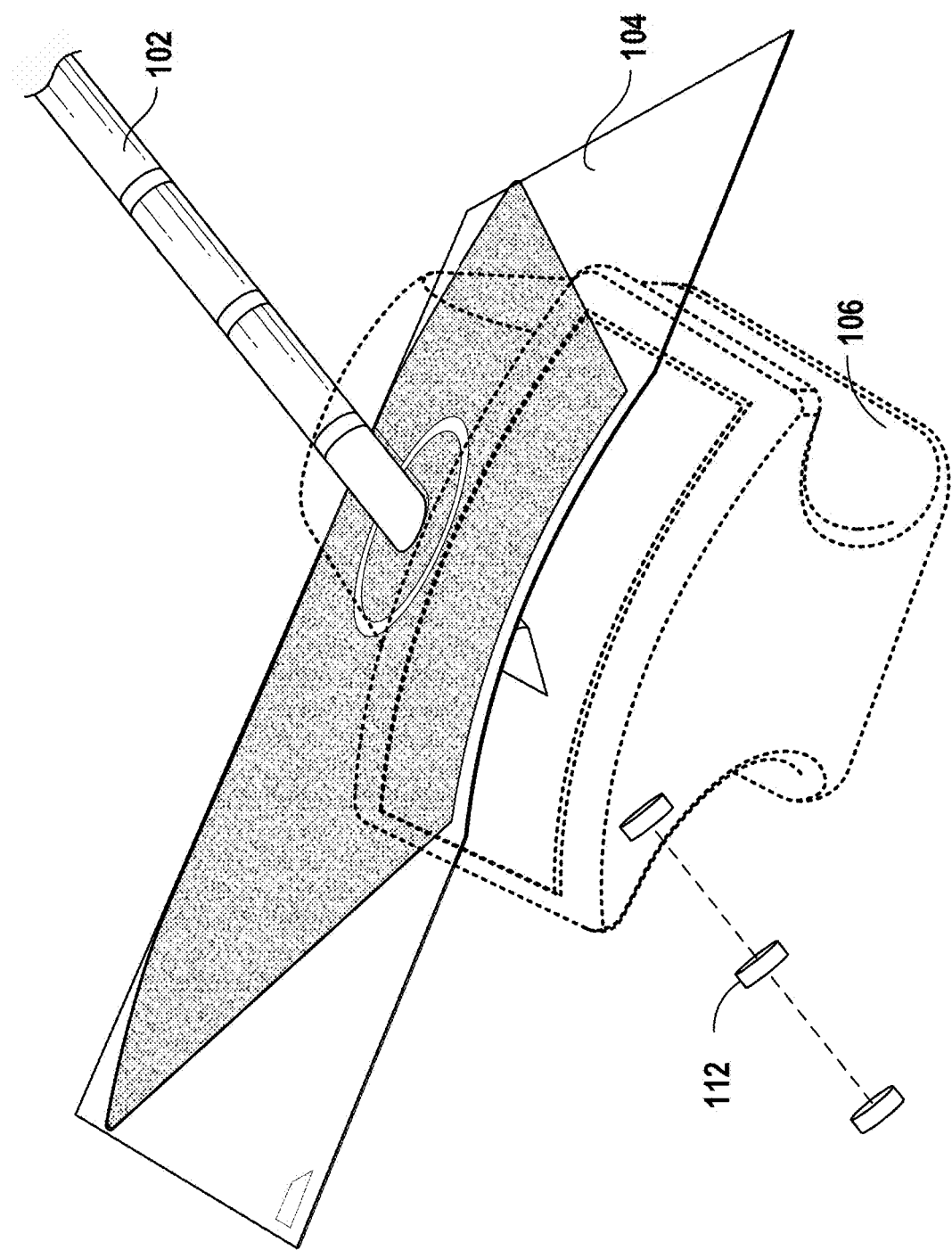
FIG. 5 is a diagram illustrating an embodiment of an example selective-transparency ending-surface rendering of a virtual transducer.

FIG. 5 is a diagram illustrating an embodiment of a rendering of imaging guidance data. FIG. 5 illustrates the display objects 102, 104, 106 in the same or similar orientation as shown in FIGS. 3 and 4. In addition, the transducer 106 is illustrated with a selective-transparency surface rendering where the selected surface is an ending-surface. In the illustrated embodiment, the ending-surface includes those surfaces, edges, or other portions of the display object that are most distant from the point-of-view location. Imagine a plurality of imaginary view-rays extending from the point-of-view location to the object. The "ending-surface" portion of that object can include the furthest surfaces of the object along multiple or all of the view-rays. In other words, the ending-surface can include an aggregation of the final exit points (from the object) from multiple or all of the view-rays.

In some cases, the selective-transparency ending-surface rendering of the transducer 106 may cause the transducer 106 to appear flipped relative to its actual orientation. That is, the back portion of the transducer 106 may appear to some users to be closer to the point-of-view location than the front portion of the transducer 106. However, as seen in FIG. 3, the front portion the transducer 106 is actually closer to the point-of-view location than the back portion of the transducer 106. This may confuse the brain's understanding of the transducer's 106 orientation, and thus the perceived spatial relationships between the image guidance data can be inaccurate. Nonetheless, in some cases, the selective-transparency ending-surface rendering of the transducer 106 can provide helpful information regarding the transducer 106.

In the illustrated embodiment of FIG. 5, the selective-transparency ending-surface rendering of the transducer 106 includes a display of the ending-surface at varying transparency levels, with other portions of the transducer 106, such as the beginning-surface, front-surface, interior, etc. being omitted, not shown, or completely transparent. Although in the illustrated embodiment of FIG. 5, only an ending-surface is used for the selective-transparency rendering, it will be understood that multiple surfaces can be used as part of a selective-transparency rendering. For example, a selective-transparency surface rendering can include a beginning-surface, ending-surface, front-surface, rear-surface, side-facing surface, etc.

In the illustrated embodiment of FIG. 5, the selective-transparency of the ending-surface is implemented with the ending-surface becoming less transparent as it gets closer to an edge. In this way, the medical image 104, the virtual needle 102, and the image guidance cues 112 are each visible through the transducer 106, and the spatial relationships between each of the transducer 106, needle 102, medical image 104, and image guidance cues 112 can be seen. In some embodiments, the selective-transparency ending-surface rendering of the transducer can reduce the number of displayed lines and improve a user's ability to properly understand the correct orientation of the transducer 106.

It will be understood that the selective-transparency of the selected surface can be implemented in a variety of ways. For example, the selective-transparency can include displaying the selected surface at the same transparency level, displaying edges of the surface opaquely or as solid or dashed lines (non-limiting example: wire frame) and the rest of the selected surface transparently or vice versa, displaying portions of the surface that are in front of another display object transparently or more transparently than portions of the selected surface that are not in front of another display object, etc.

Moreover, when a selective-transparency rendering includes multiple surfaces, each surface can be rendered using the same selective-transparency or different selective transparencies. For example, an ending-surface can be rendered such that portions of the ending-surface that are closer to an edge are rendered at a different opacity (for example, more opaquely) than portions that are farther away from an edge. As another example, an ending-surface can be rendered such that the entire surface has a single level of transparency or alternatively can be rendered such that only edges of the ending-surface are rendered opaquely, while other portions of the ending-surface are render with a diminished opacity or are completely transparent.

In addition or alternatively to a selective-transparency rendering of the transducer, the system can render one or more selected surfaces of one or more other display objects. For example, it can be advantageous for the physician to see at least the ending-surface of every display object. Accordingly, in some cases, each display object (or portion of each display object) that is in front of another display object (with respect to the point-of-view location) can be rendered with a selective-transparency ending-surface rendering. For instance, referring to the illustrated embodiment of FIG. 5, a portion of the virtual needle 102 overlaps with a portion of the medical image 104. In some cases, at least one of the ending-surfaces of the virtual needle 102 or the medical image 104 can be displayed using a selective-transparency ending-surface rendering such that each ending-surface portion of every display object is visible to the physician. Furthermore, in some embodiments, all display objects, or a subset thereof, can be displayed using a selective-transparency rendering.

Furthermore, as described herein, the selected surfaces can be rendered selectively transparent in a variety of ways. For example, the system can render portions of the selected surface of a display object that overlap with other display objects transparently or more transparently than non-overlapping portions of the display object, which can be rendered opaquely (for example, like the transducer 106 as illustrated in FIG. 3). In certain embodiments, the non-overlapping portions of the display object can be displayed at one or more different transparency levels similar to the overlapping portions of the selected surface. In some cases, if more than two display objects (or other image guidance data) are overlapping at the same location (for example, the same pixel on the display 170), then two or more of the overlapping display objects or portions thereof can be displayed using a selective-transparency rendering. For example, the closest display object or portion thereof (relative to the point-of-view location) can be displayed using a selective-transparency ending-surface rendering. In addition, the second closest display object or portion thereof (relative to the point-of-view location) can be displayed using a selective-transparency ending-surface rendering. In some cases, the selective-transparency of the using a selective-transparency ending-surface renderings of the first and second objects can be different. For example, the second object can use a different selective-transparency scheme, such as more transparent or a uniform transparency level. Rendering the multiple ending-surface renderings at different transparency levels can allow each overlapping portion to be visible to the physician, and can allow the physician to understand the spatial relationships between each display object, or other image guidance data.

Although only the edges of the ending-surface of the virtual ultrasound transducer 106 are clearly depicted in FIG. 5 (for example, for stylistic reasons due to the constraints of black/white illustration), it should be noted that other portions of the ending-surface may be displayed, such as the continuous portions between the edges. In some embodiments, the rendering of the transducer 106 can include shading and other visualization techniques to illustrate contours of the transducer 106. For example, in some cases, surface shading can be added to the ending-surface rendering of the virtual ultrasound transducer 106, which can make the virtual ultrasound transducer 106 more salient and easier to see, despite its transparency.

As described above, in some cases, rendering the selective-transparency ending-surface rendering of the transducer 106 can include omitting, ignoring, rendering transparently or otherwise not showing portions of the transducer 106 that are not portions of the ending-surface. For example, portions that are not part of the ending-surface can include the beginning-surfaces, the back-surface, the interior, one or more sides, or the like. As a non-limiting example, to render the selective-transparency ending-surface rendering of the transducer 106, the system can determine the ending-surface of the transducer and can determine the portions of the transducer that are not included in the ending-surface. In some cases, the system can display the selective-transparency ending-surface rendering of the transducer 106 can discard, omit, or display transparently the portions of the transducer that are not included in the ending-surface.

Beginning-Surface and Ending-Surface Rendering

Figure 6:
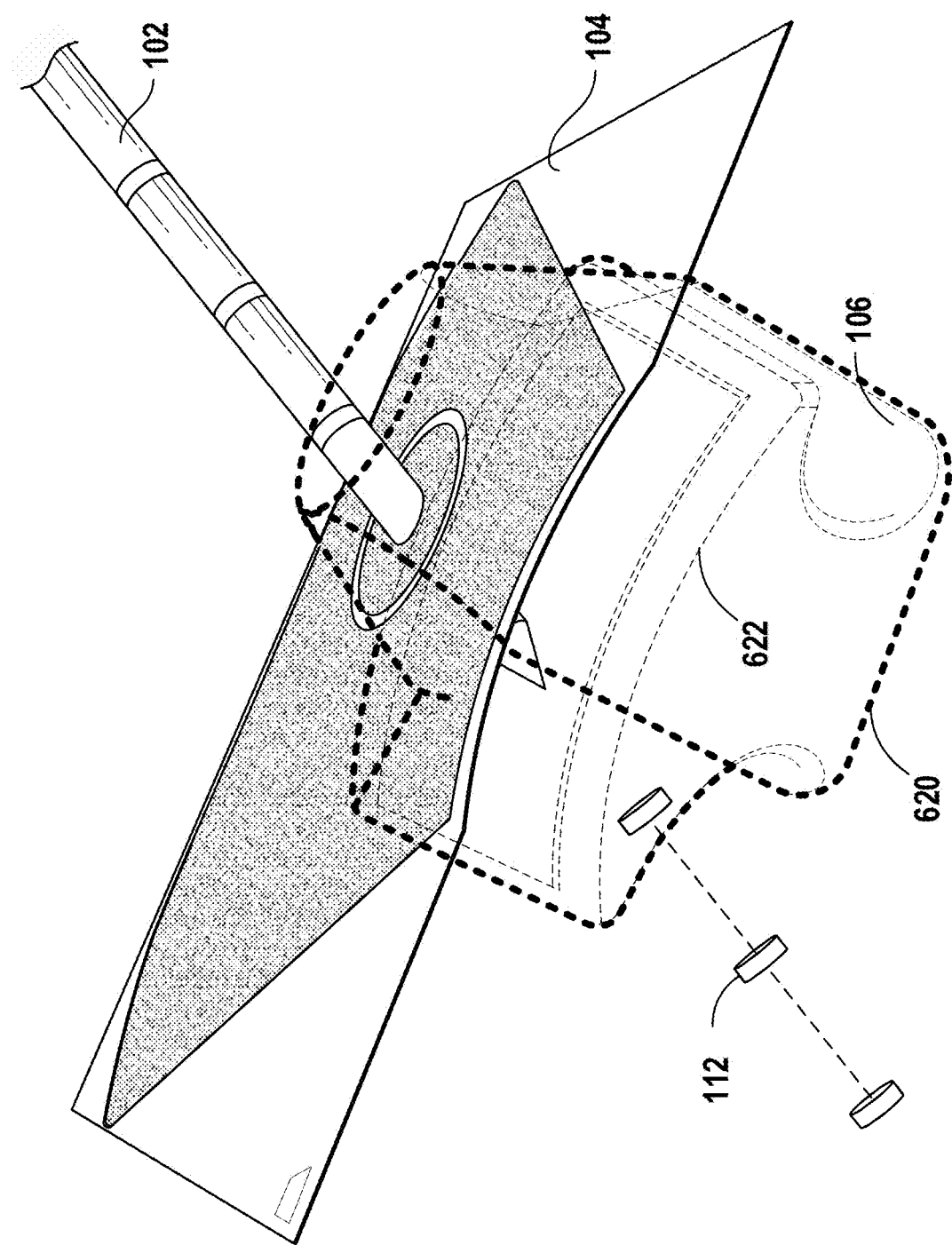
FIG. 6 is a diagram illustrating an embodiment of an example selective-transparency beginning-surface and ending-surface rendering of a virtual transducer.

FIG. 6 is a diagram illustrating an embodiment of a rendering of imaging guidance data. FIG. 6 illustrates the display objects 102, 104, 106 in the same or similar orientation as shown in FIGS. 3-5. In addition, the transducer 106 is illustrated with a selective-transparency surface rendering where the multiple surfaces are selected. In the illustrated example, the selected surfaces include a beginning-surface, such as described with respect to FIG. 4, and an ending-surface, such as described with respect to FIG. 5.

In the illustrated embodiment of FIG. 6, the selective-transparency beginning-surface and ending-surface rendering of the transducer 106 includes a display of the beginning- and ending-surfaces at varying transparency levels, with other portions of the transducer 106, such as the interior or side-surface being omitted, not shown, or completely transparent. Although in the illustrated embodiment of FIG. 6, only beginning- and ending-surfaces are used for the selective-transparency rendering, it will be understood that other surfaces can be used as part of a selective-transparency rendering. For example, a selective-transparency surface rendering can include a beginning-surface, ending-surface, front-surface, rear-facing surface, side-facing surface, interior, etc.

In the illustrated embodiment of FIG. 6, the selective-transparency rendering is implemented with the selective-transparency scheme of the rendered portion of the ending-surface being different than (for example, diminished as compared to) the selective-transparency scheme of the rendered portion of the beginning-surface, where the beginning-surface is represented by a thick, dashed line 620 and the ending-surface is represented by a thin, dashed line 622. By selecting various combinations of opacity, hue, saturation, and brightness for the beginning- and ending-surfaces of the transducer 106, the system can achieve improved perception of the transducer 106 as compared to the transducer rendering being implemented with a single transparency level. In the illustrated embodiment of FIG. 6, the medical image 104, the virtual needle 102, and the image guidance cues 112 are each visible through the transducer 106, and the spatial relationships between each of the transducer 106, needle 102, medical image 104, and image guidance cues 112 can be seen. Furthermore, the physician can understand the poses of the display objects, as well as the spatial relationships between each display object or other image guidance data.

It will be understood that the selective-transparency of the selected surfaces can be implemented in a variety of ways. For example, the selective-transparency can include displaying one or more of the selected surfaces at the same transparency level, displaying edges of a surface opaquely or as solid or dashed lines (non-limiting example: wire frame) and the rest of that selected surface transparently or vice versa, displaying portions of a surface that are in front of another display object transparently or more transparently than portions of that selected surface that are not in front of another display object, etc.

Moreover, when a selective-transparency rendering includes multiple surfaces, each surface can be rendered using the same selective-transparency or different selective transparencies. For example, an ending-surface can be rendered such that portions of the selected surfaces that are closer to an edge are rendered at a different opacity (for example, more opaquely) than portions that are farther away from an edge. As another example, a selected surface can be rendered such that the surfaces have a single level of transparency or alternatively can be rendered such that only edges of the selected surfaces are rendered opaquely or partially transparently, while other portions of the selected surfaces are render with a diminished opacity or are completely transparent.

In addition or alternatively to a selective-transparency rendering of the transducer, the system can render one or more selected surfaces of one or more other display objects. For example, it can be advantageous for the physician to see at least a beginning-surface and/or an ending-surface of every display object. Accordingly, in some cases, each display object (or portion of each display object) that is in front of another display object (with respect to the point-of-view location) can be rendered with a selective-transparency beginning-surface and/or ending-surface rendering. For instance, referring to the illustrated embodiment of FIG. 6, a portion of the virtual needle 102 overlaps with a portion of the medical image 104. In some cases, at least one of the beginning- and/or ending-surfaces of the virtual needle 102 or the medical image 104 can be displayed using a selective-transparency beginning-surface and/or ending-surface rendering such that each beginning-surface and/or ending-surface portion of every display object is visible to the physician. Furthermore, in some embodiments, all display objects, or a subset thereof, can be displayed using a selective-transparency rendering.

Furthermore, as described herein, the selected surfaces can be rendered selectively transparent in a variety of ways. For example, the system can render portions of the selected surface of a display object that overlap with other display objects transparently or more transparently than non-overlapping portions of the display object, which can be rendered opaquely (for example, like the transducer 106 as illustrated in FIG. 3). In certain embodiments, the non-overlapping portions of the display object can be displayed at one or more different transparency levels similar to the overlapping portions of the selected surface. In some cases, if more than two display objects (or other image guidance data) are overlapping at the same location (for example, the same pixel on the display 170), then two or more of the overlapping display objects or portions thereof can be displayed using a selective-transparency rendering. For example, the closest display object or portion thereof (relative to the point-of-view location) can be displayed using a selective-transparency beginning-surface and/or ending-surface rendering. In addition, the second closest display object or portion thereof (relative to the point-of-view location) can be displayed using a selective-transparency beginning-surface and/or ending-surface rendering. In some cases, the selective-transparency of the using a selective-transparency beginning-surface and/or ending-surface renderings of the first and second objects can be different. For example, the second object can use a different selective-transparency scheme, such as more transparent or a single transparency level. Rendering the multiple beginning-surface and/or ending-surface renderings at different transparency levels can allow each overlapping portion to be visible to the physician, and can allow the physician to understand the spatial relationships between each display object, or other image guidance data.

Although only the edges of the beginning- and ending-surfaces of the virtual ultrasound transducer 106 are clearly depicted in FIG. 6 (for example, for stylistic reasons due to the constraints of black/white illustration), it should be noted that other portions of the beginning- or ending-surface may be displayed, such as the continuous portions between the edges. In some embodiments, the rendering of the transducer 106 can include shading and other visualization techniques to illustrate contours of the transducer 106. For example, in some cases, surface shading can be added to the beginning-surface or ending-surface renderings of the virtual ultrasound transducer 106, which can make the virtual ultrasound transducer 106 more salient and easier to see, despite its transparency.

As described above, in some cases, rendering the selective-transparency ending-surface rendering of the transducer 106 can include omitting, ignoring, rendering transparently or otherwise not showing portions of the transducer 106 that are not portions of the beginning-surface or the ending-surface. For example, portions that are not part of the beginning-surface or the ending-surface can include the portions of a side-surface or interior of the transducer.

Exterior Surface

Figure 7:
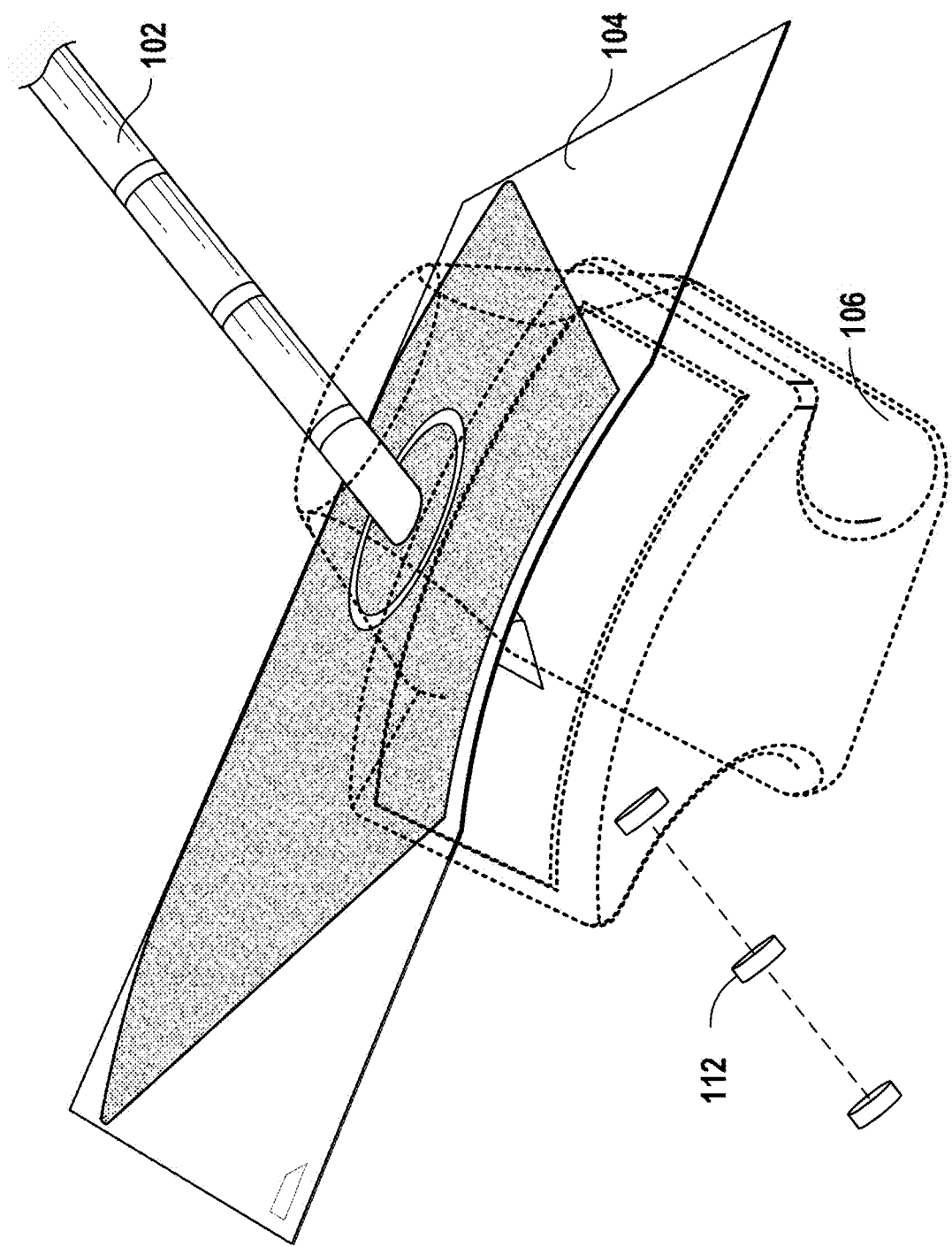
FIG. 7 is a diagram illustrating an embodiment of an example selective-transparency exterior surface rendering of a virtual transducer.

FIG. 7 is a diagram illustrating an embodiment of a rendering of imaging guidance data. FIG. 7 illustrates the display objects 102, 104, 106 in the same or similar orientation as shown in FIGS. 3-6. In addition, the transducer 106 is illustrated with a selective-transparency surface rendering where the multiple surfaces are selected. In the illustrated example, the selected surfaces include exterior surfaces of the transducer 106. In the illustrated embodiment, the exterior surfaces include each of the outer surfaces of the transducer 106. For example, the exterior surfaces can include a combination of surfaces, edges, or other portions of the beginning-surface, ending-surface, front-surface, back-surface, side-surface, or the like.

In the illustrated embodiment of FIG. 7, physical details of the virtual ultrasound transducer 106 that were occluded or located on the far side of the transducer of FIG. 3 are now visible, thereby rendering a more informative image. For example, the image includes extra details of the transducer, such as the transducer's contours. In some cases, these details can lead to the brain's misunderstanding of the transducer's 106 orientation. This phenomenon, known as multistable, ambiguous perception, can cause the user to perceive that the transducer is in an orientation that is different from the actual orientation of the transducer 106. For example, as illustrated in FIG. 7, the orientation of the transducer 106 can appear flipped as compared to the orientation of the transducer shown in FIG. 3. Nonetheless, in some cases, the selective-transparency exterior surface rendering of the transducer 106 can provide information regarding the transducer 106 that can aid a user in placing the needle 102.

In the illustrated embodiment of FIG. 7, the selective-transparency exterior surface rendering of the transducer 106 includes a display of each of the exterior surfaces at varying transparency levels, with other portions of the transducer 106, such as the interior, being omitted, not shown, or completely transparent. Although in the illustrated embodiment of FIG. 7, only exterior surfaces are used for the selective-transparency rendering, it will be understood that other surfaces can be used as part of a selective-transparency rendering. For example, a selective-transparency surface rendering can include an interior of the transducer. Furthermore, it will be understood that the selective-transparency rendering can include fewer surfaces than illustrated in FIG. 7. For example, one or more of the beginning-, ending-, front-, back-, or side-surface can be omitted, not shown, or can be retendered completely transparently.

In the illustrated embodiment of FIG. 7, the selective-transparency of the exterior surface is implemented with the exterior surface becoming less transparent as it gets closer to an edge. In this way, the medical image 104, the virtual needle 102, and the image guidance cues 112 are each visible through the transducer 106, and the spatial relationships between each of the transducer 106, needle 102, medical image 104, and image guidance cues 112 can be seen. In some embodiments, the selective-transparency exterior surface rendering of the transducer can reduce the number of displayed lines and improve a user's ability to properly understand the correct orientation of the transducer 106.

It will be understood that the selective-transparency of the selected surface can be implemented in a variety of ways. For example, the selective-transparency can include displaying the selected surface at the same transparency level, displaying edges of the surface opaquely or as solid or dashed lines (non-limiting example: wire frame) and the rest of the selected surface transparently or vice versa, displaying portions of the surface that are in front of another display object transparently or more transparently than portions of the selected surface that are not in front of another display object, etc.

Moreover, when a selective-transparency rendering includes multiple surfaces, each surface can be rendered using the same selective-transparency or different selective transparencies. For example, an exterior surface can be rendered such that portions of the exterior surface that are closer to an edge are rendered at a different opacity (for example, more opaquely) than portions that are farther away from an edge. As another example, an exterior surface can be rendered such that the entire surface has a single level of transparency or alternatively can be rendered such that only edges of the exterior surface are rendered opaquely, while other portions of the exterior surface are render with a diminished opacity or are completely transparent.

In addition or alternatively to a selective-transparency rendering of the transducer, the system can render one or more selected surfaces of one or more other display objects. For example, it can be advantageous for the physician to see at least the exterior surface of every display object. Accordingly, in some cases, each display object (or portion of each display object) that is in front of another display object (with respect to the point-of-view location) can be rendered with a selective-transparency exterior surface rendering. For instance, referring to the illustrated embodiment of FIG. 7, a portion of the virtual needle 102 overlaps with a portion of the medical image 104. In some cases, at least one of the exterior surfaces of the virtual needle 102 or the medical image 104 can be displayed using a selective-transparency exterior surface rendering such that each exterior surface portion of every display object is visible to the physician. Furthermore, in some embodiments, all display objects, or a subset thereof, can be displayed using a selective-transparency rendering.

Furthermore, as described herein, the selected surfaces can be rendered selectively transparent in a variety of ways. For example, the system can render portions of the selected surface of a display object that overlap with other display objects transparently or more transparently than non-overlapping portions of the display object, which can be rendered opaquely (for example, like the transducer 106 as illustrated in FIG. 3). In certain embodiments, the non-overlapping portions of the display object can be displayed at one or more different transparency levels similar to the overlapping portions of the selected surface. In some cases, if more than two display objects (or other image guidance data) are overlapping at the same location (for example, the same pixel on the display 170), then two or more of the overlapping display objects or portions thereof can be displayed using a selective-transparency rendering. For example, the closest display object or portion thereof (relative to the point-of-view location) can be displayed using a selective-transparency exterior surface rendering. In addition, the second closest display object or portion thereof (relative to the point-of-view location) can be displayed using selective-transparency exterior surface rendering. In some cases, the selective-transparency of the using a selective-transparency exterior surface renderings of the first and second objects can be different. For example, the second object can use a different selective-transparency scheme, such as more transparent or a uniform transparency level. Rendering the multiple exterior surface renderings at different transparency levels can allow each overlapping portion to be visible to the physician, and can allow the physician to understand the spatial relationships between each display object, or other image guidance data.

Although only the edges of the exterior surface of the virtual ultrasound transducer 106 are clearly depicted in FIG. 7 (for example, for stylistic reasons due to the constraints of black/white illustration), it should be noted that other portions of the exterior surface may be displayed, such as the continuous portions between the edges. In some embodiments, the rendering of the transducer 106 can include shading and other visualization techniques to illustrate contours of the transducer 106. For example, in some cases, surface shading can be added to the exterior surface rendering of the virtual ultrasound transducer 106, which can make the virtual ultrasound transducer 106 more salient and easier to see, despite its transparency.

As described above, in some cases, rendering the selective-transparency exterior surface rendering of the transducer 106 can include omitting, ignoring, rendering transparently or otherwise not showing portions of the transducer 106 that are not portions of the exterior surface. For example, portions that are not part of the exterior surface can include the interior of the transducer.

Example Front-, Back-, Ending-, and Beginning-Surfaces

FIGS. 8A-8F are diagrams useful for illustrating differences between determining front-, back-, ending-, and beginning-surfaces. For ease of reference, FIGS. 8A-8F illustrate an orthographic projection of a 3D scene for display on display 170. It will be understood that these diagrams are illustrative in nature, and should not be construed as limiting. Further, the associated description of FIGS. 8A-8F can be applicable to three-dimensional objects, as well as to the illustrated two-dimensional object.

Figure 8A:
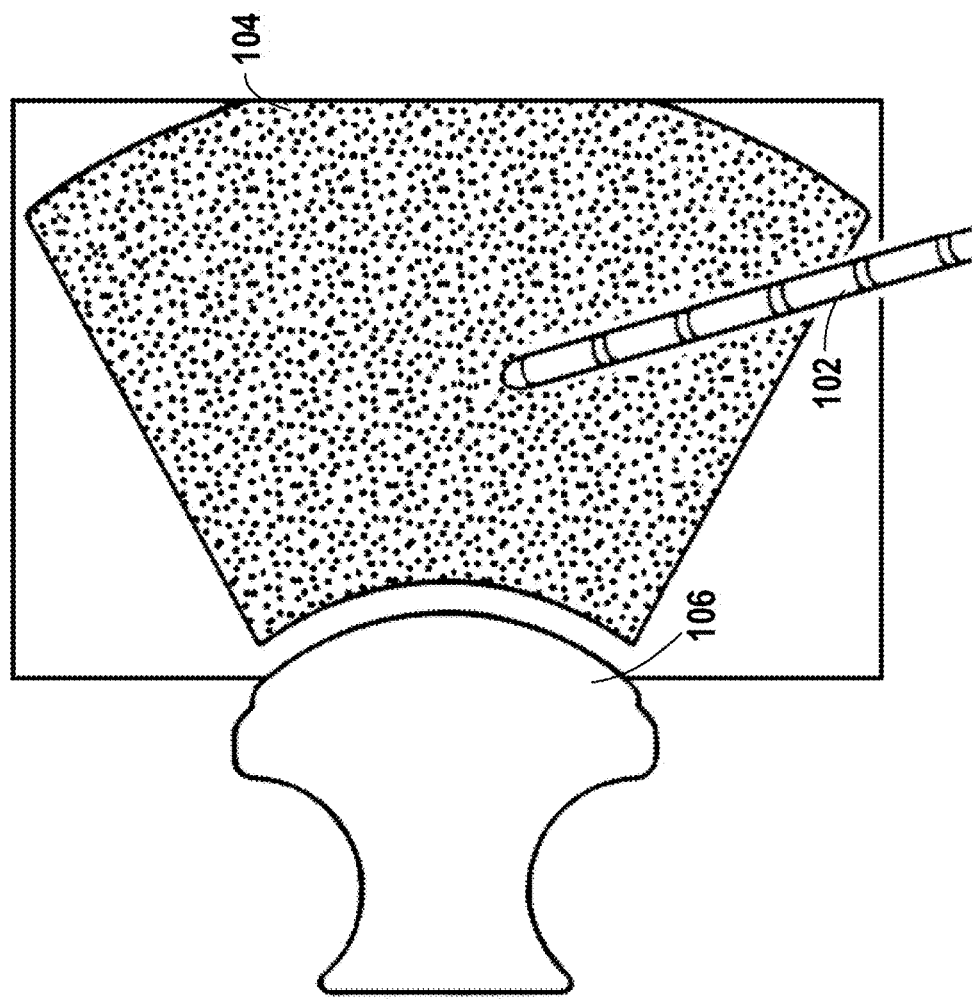
FIGS. 8A-8F are diagrams useful for illustrating differences between determining front-, back-, ending-, and beginning-surfaces.

FIG. 8A is a block diagram illustrating an embodiment of a virtual surgical environment, such as the 3D scene 110 described herein, on the right side of the figure. In addition, FIG. 8A illustrates a viewpoint or point-of-view location 802 (in this example, depicted as a user's eye) on the left side of the figure. As described herein, the point-of-view location 802 can refer to the location from which a virtual 3D space is viewed. Accordingly, in this example, a viewer of the display 170 would be viewing the scene from the perspective of the illustrated eye 802.

Figure 8B:
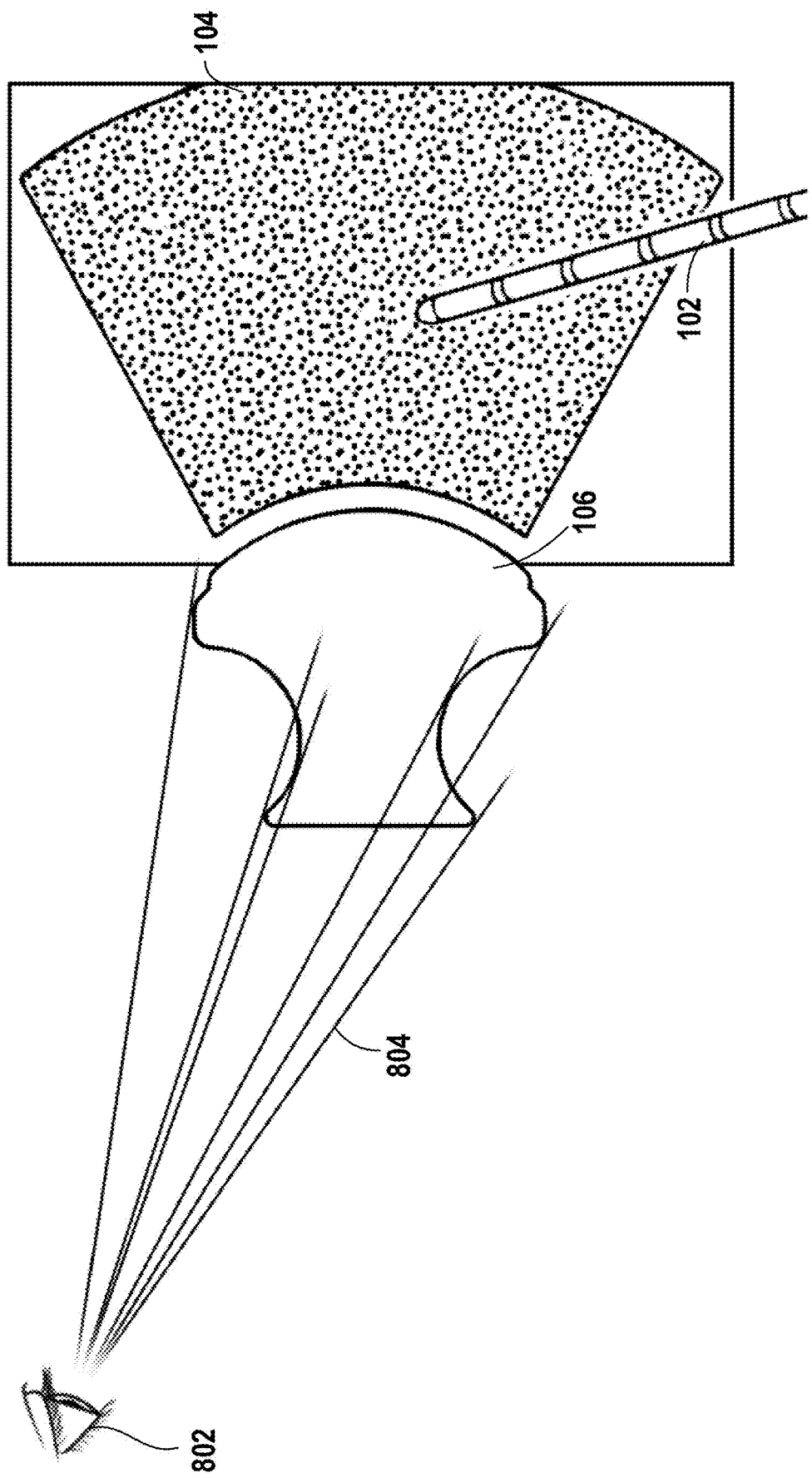

FIG. 8B is a block diagram illustrating an embodiment of a virtual surgical environment that includes a plurality of view-rays 804 extending from the point-of-view location 802 to the virtual transducer 106. The plurality of view-rays 804 can include an infinite number of view-rays, such that every portion or fragment of the virtual transducer 106 intersects with a view-ray. It will be understood that the view-rays 804 are for illustrative or calculation purposes and are not necessarily rendered by the system. Rather, as illustrated in FIGS. 8C-8F, these view-rays can be useful in distinguishing between a front-surface, back-surface, beginning-surface, and ending-surface.

Example Front-Surface

Figure 8C:
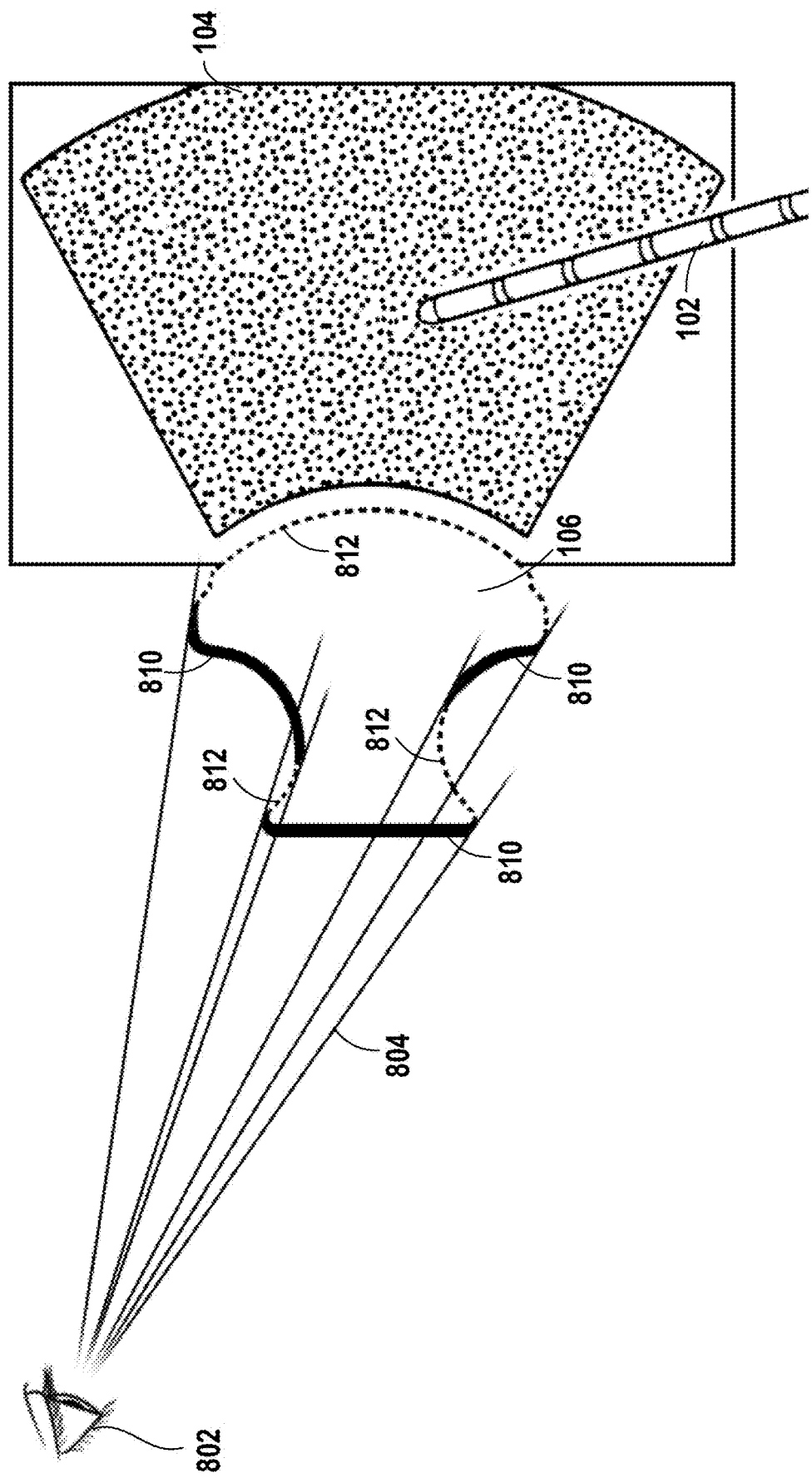

FIG. 8C is a block diagram illustrating an embodiment of a virtual surgical environment that includes a plurality of view-rays 804 extending from the point-of-view location 802 to the virtual transducer 106. As illustrated by the bolded lines 810 outlining portions of the transducer 106, the front-surface of an object can include the surfaces, edges, and/or other portions of the transducer 106 that face the point-of-view location 802. Further, in certain embodiments, as illustrated by the dashed lines 812 outlining other portions of the transducer 106, the front-surface can omit the surfaces, edges, or other portions of the transducer 106 that do not face the point-of-view location 802. Furthermore, in certain embodiments, the front-surface of the transducer 106 can omit the interior or inner portions of the transducer. Accordingly, in some embodiments, the front-surface may only include outer surfaces of the object.

Example Back-Surface

Figure 8D:
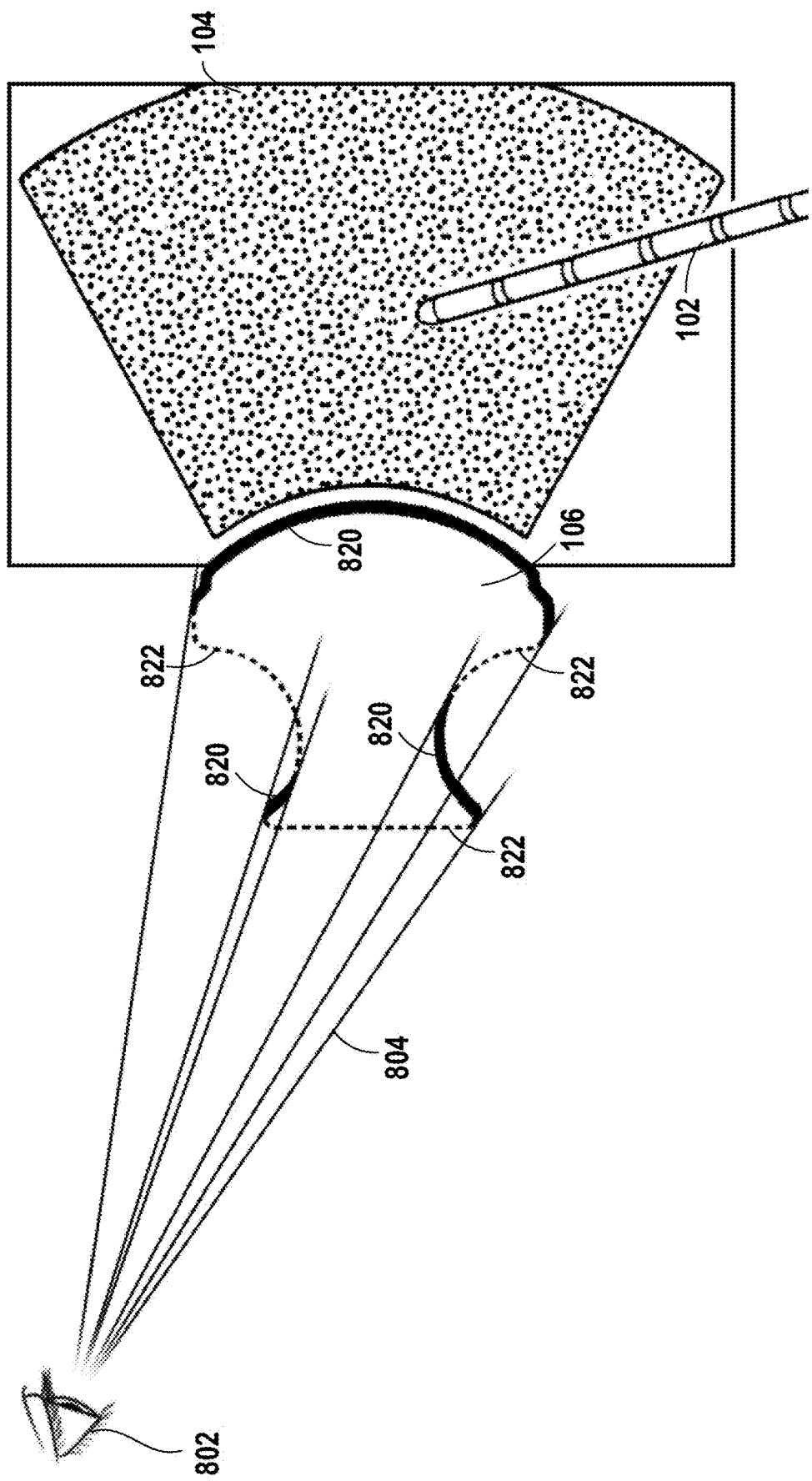

FIG. 8D is a block diagram illustrating an embodiment of a virtual surgical environment that includes a plurality of view-rays 804 extending from the point-of-view location 802 to the virtual transducer 106. As illustrated by the bolded lines 820 outlining portions of the transducer 106, the back-surface of an object can include the surfaces, edges, and/or other portions of the transducer 106 that do not face the point-of-view location 802. Further, in certain embodiments, as illustrated by the dashed lines 822 outlining other portions of the transducer 106, the back-surface can omit the surfaces, edges, or other portions of the transducer 106 that face the point-of-view location 802. Thus, as can be seen by a comparison of FIGS. 8C and 8D, in some embodiments, a back-surface can be described as the opposite of the front-surface. Furthermore, in certain embodiments, the back-surface of the transducer 106 can omit the interior or inner portions of the transducer. Accordingly, in some embodiments, the back-surface may only include outer surfaces of the object.

Example Ending-Surface

Figure 8E:
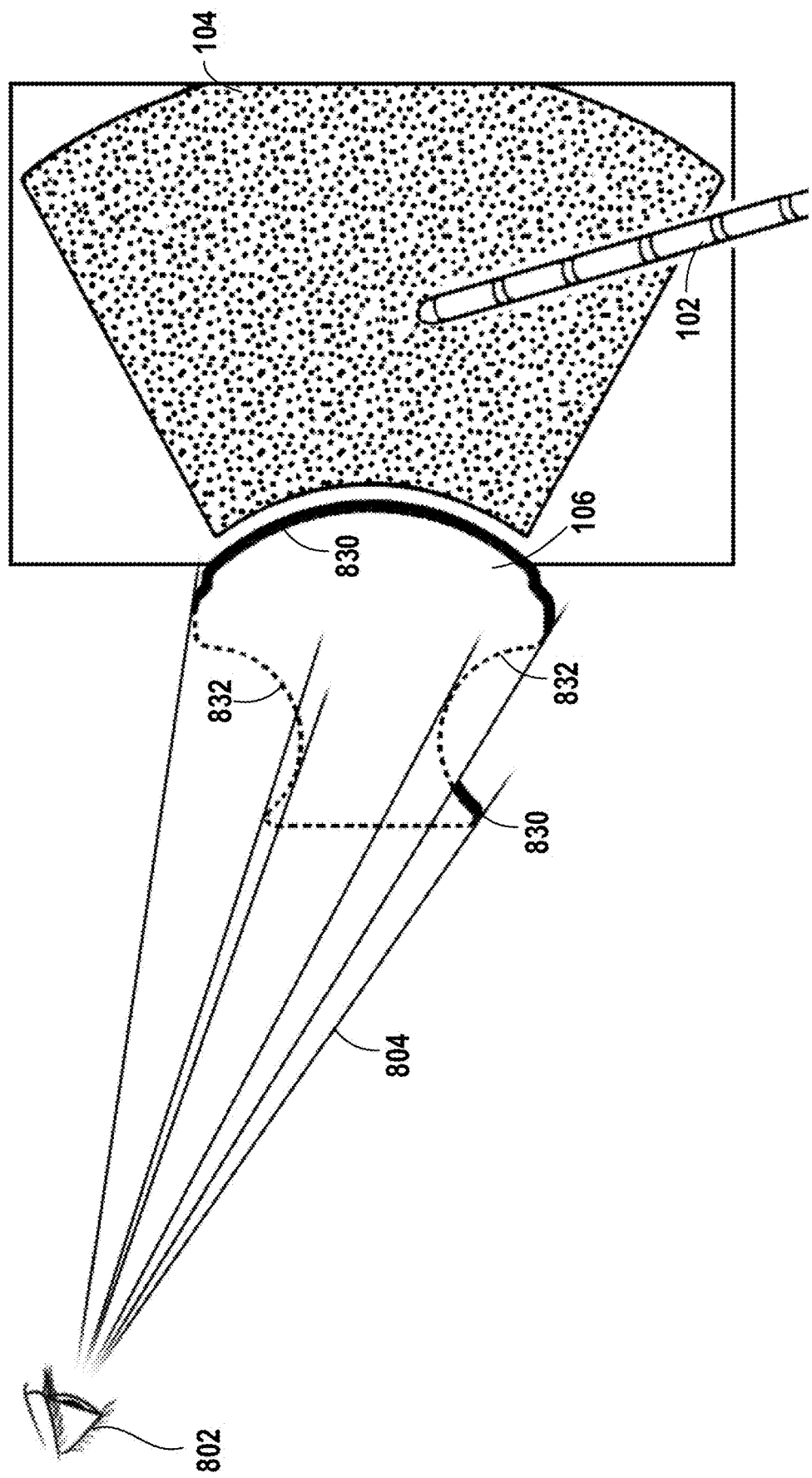

FIG. 8E is a block diagram illustrating an embodiment of a virtual surgical environment that includes a plurality of view-rays 804 extending from the point-of-view location 802 to the virtual transducer 106. In the illustrated embodiment, an example ending-surface is shown by the solid, bolded lines 830 outlining portions of the transducer 106, while the other outer surfaces of the transducer are shown by broken lines 832 outlining portions of the transducer 106.

In some embodiments, the ending-surface can be described with reference to the view-rays 804 extending from the point-of-view location 802. As illustrated, multiple view-rays intersect with the object 106. Although, in some cases, a particular view-ray may have multiple exit points (for example, depending on the shape of the object, a view-ray may enter the object, then exit the object, then re-enter the object, then re-exit the object and so on), a view-ray that intersects with the object 106 has one final exit point from the object. In some embodiments, the ending-surface can be determined as the aggregation of final exit points of multiple or all of the view-rays 804, as illustrated by the bolded lines 830 outlining portions of the transducer 106. For example, in certain cases, the ending-surface can be determined by aggregating the final exit points of the view-rays 804 that intersect with the object 106.

Although the view-rays 804 illustrated in FIG. 7 extend from a point-of-reference, in some cases, the view-rays 804 can extend from a plane of reference. For example, the view-rays can extend orthogonally or obliquely from a plane of reference and a subset of the view-rays can intersect with the object, as described above. In this example, the ending-surface could similarly include the aggregation of final exit points from multiple or all of the view-rays.

Example Beginning-Surface

Figure 8F:
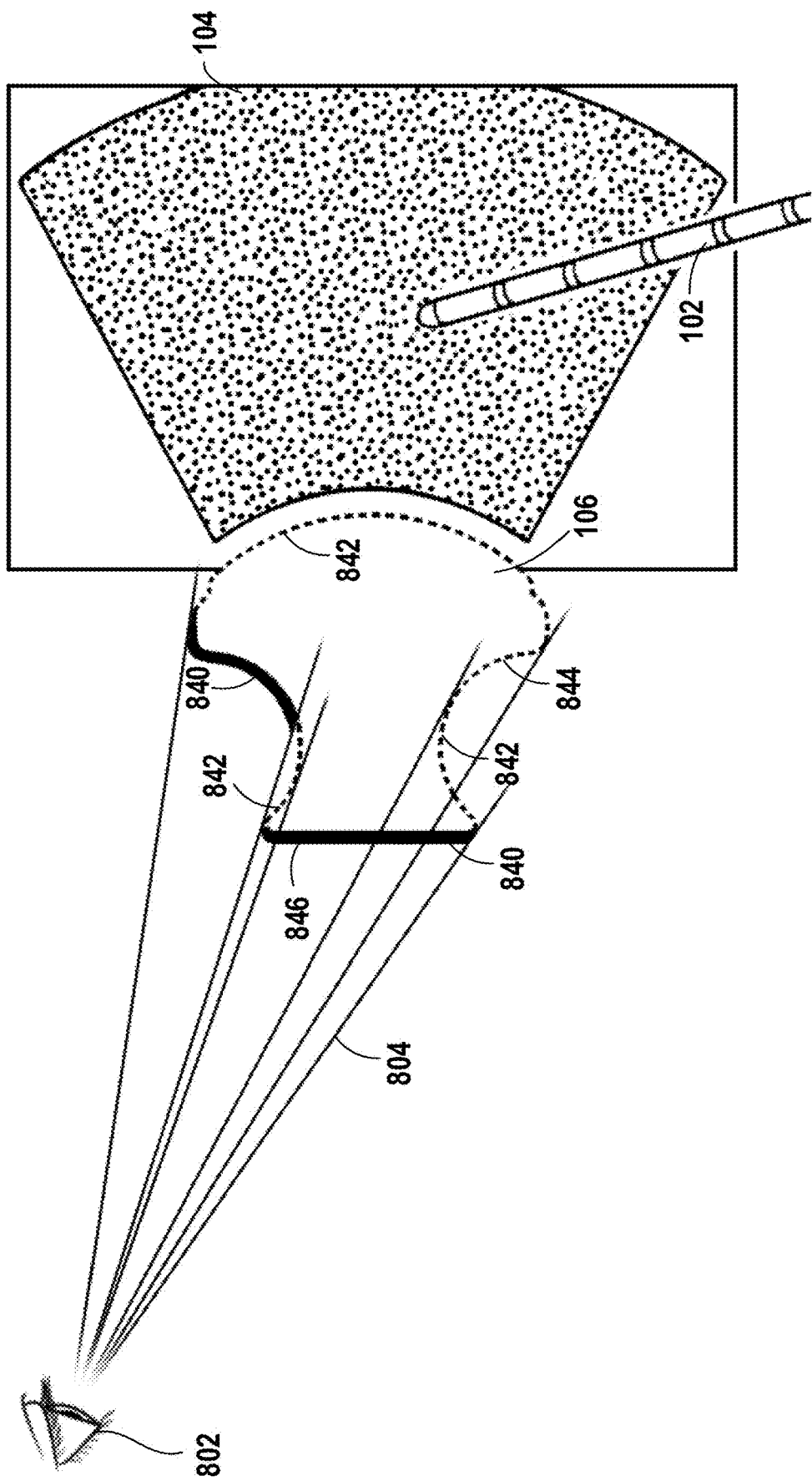

FIG. 8F is a block diagram illustrating an embodiment of a virtual surgical environment that includes a plurality of view-rays 804 extending from the point-of-view location 802 to the virtual transducer 106. In the illustrated embodiment, an example the beginning-surface is shown by the solid, bolded lines 840 outlining portions of the transducer 106, while the other outer surfaces of the transducer are shown by broken lines 842 outlining portions of the transducer 106.

As illustrated by the bolded lines 840 outlining portions of the transducer 106, in some embodiments, the beginning-surface can include those surfaces, edges, or other portions of the object 106 that are both facing the point-of-view location 802 and not occluded from view by the object's shape. Further, in certain embodiments, a beginning-surface may only include those surfaces, edges, or other portions of the object 106 that are both facing the point-of-view location 802 and not occluded from view by the object's shape. Accordingly, in contrast to the front-surface representation in FIG. 8C, in some cases, the beginning-surface may not include each of the surfaces of the object 106 that face the point-of-view location 802. An example of this is shown by the dashed surface 844, which faces the point-of-view location 802 but is occluded from view by the object's shape. For example, the dashed surface 844 is occluded from view at the point-of-view location 802 at least by surface 846.

In some embodiments, the beginning-surface of an object may also be explained or described with reference to the view-rays 804 which are illustrated as extending from the point-of-view location 802. As illustrated, multiple view-rays 804 intersect with a portion of the object 106. Although, in some cases, a particular view-ray may have multiple entry points (for example, depending on the shape of the object, a view-ray may initially enter the object, then exit the object, then re-enter the object and so on), a view-ray that intersects with the object 106 has one initial entry point into the object. Accordingly, in some embodiments, the beginning-surface can be determined using the aggregation of initial entry points of multiple or all of the view-rays 804. For example, in certain cases, the beginning-surface can be determined by aggregating the initial entry points of the view-rays 804 that intersect with the object 106.

Although the view-rays 804 illustrated in FIG. 8F extend from a point-of-reference, in some cases, the view-rays 804 can extend from a plane of reference. For example, the view-rays can extend orthogonally or obliquely from a plane of reference and a subset of the view-rays can intersect with the object, as described above. In this example, the beginning-surface could similarly include the aggregation of initial entry points from multiple or all of the view-rays.

It should be noted that, in certain embodiments, the beginning- and ending-surfaces do not necessarily complement each other to the complete object surface. In other words, the beginning- and ending-surfaces may not be mirror images of or opposite each other. For example, as illustrated in FIGS. 8E and 8F, at least some portions of an object may not be included in a beginning-surface or an ending-surface of the object. This can be the case for objects with concavities, for example.

Example Front-, Back-, Ending- and Beginning-Surfaces

FIGS. 9A-9D are diagrams useful for illustrating differences between determining front-, back-, ending-, and beginning-surfaces. Each of FIGS. 9A-9D illustrate a viewpoint or point-of-view location 902 (in this example, depicted as a user's eye) on the left side of the figure. As described herein, the point-of-view location 902 can refer to the location from which a virtual 3D space is viewed. Accordingly, in these examples, a viewer of the display 170 would be viewing the scene from the perspective of the illustrated eye 902. It will be understood that these diagrams are illustrative in nature, and should not be construed as limiting. Further, the associated description of FIGS. 9A-9D can be applicable to two-dimensional objects, as well as to other three-dimensional objects.

Example Front-Surface

Figure 9A:
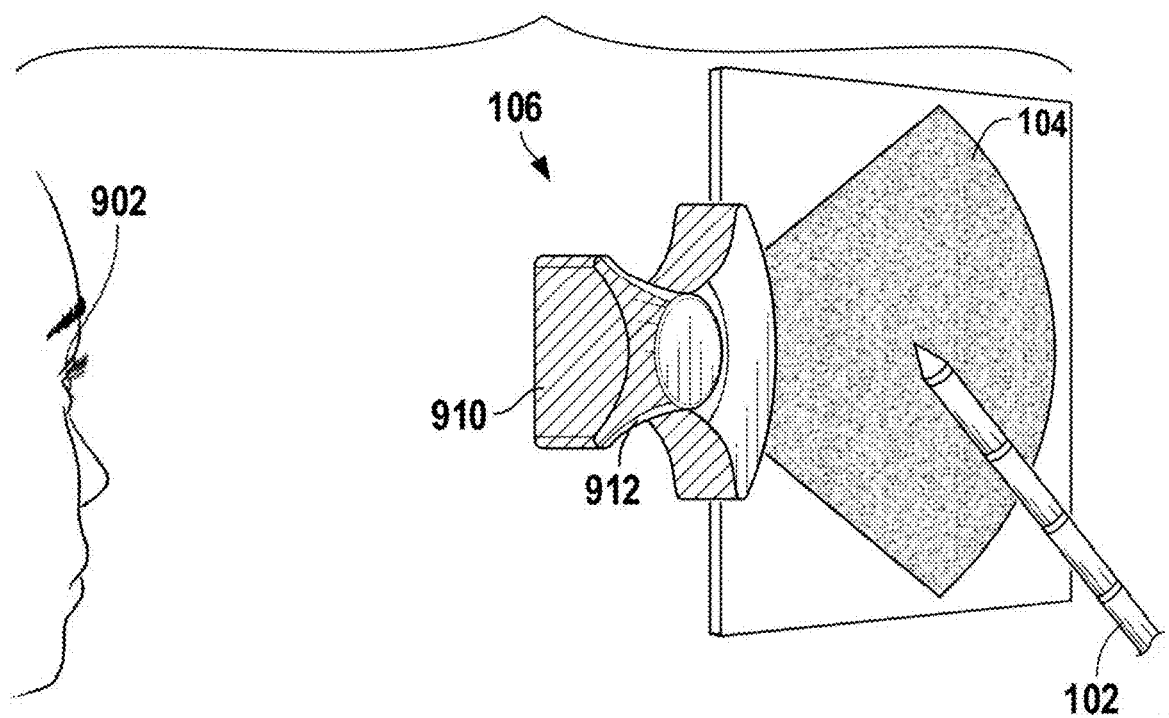
FIGS. 9A-9D are diagrams useful for illustrating differences between determining front-, back-, ending-, and beginning-surfaces.

FIG. 9A is a block diagram illustrating an embodiment of a virtual surgical environment. As illustrated by the shaded portions 910 of the transducer 106, the front-surface of an object can include the surfaces, edges, and/or other portions of the transducer 106 that face the point-of-view location 902. Further, in certain embodiments, the front-surface can omit, the surfaces, edges, or other portions of the transducer 106 that do not face the point-of-view location 902, such as those portions of the transducer that cannot be seen in FIG. 9A (for example, the back side of the transducer 106). Furthermore, the selective-transparency front-surface rendering of the transducer 106 can omit the interior or inner portions of the transducer. Accordingly, in some embodiments, the front-surface may only include outer surfaces of the object.

Example Back-Surface

Figure 9B:
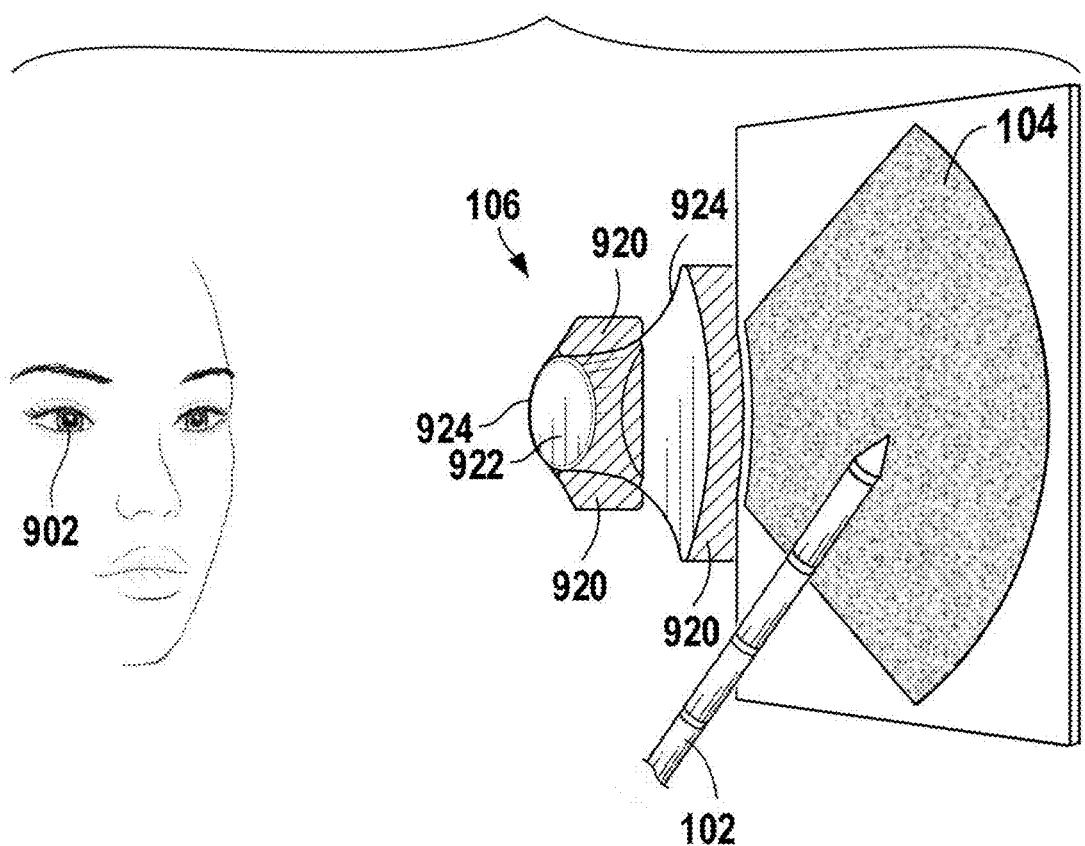

FIG. 9B is a block diagram illustrating an embodiment of a virtual surgical environment. As illustrated by the shaded portions 920 of the transducer 106, the back-surface of an object can include surfaces, edges, or other portions of the transducer 106 that do not face the point-of-view location 902. Further, in certain embodiments, the back-surface can omit, the surfaces, edges, or other portions of the transducer 106 that do not face the point-of-view location 902, such as those portions of the transducer that cannot be seen in FIG. 9B (for example, the front side of the transducer 106). Furthermore, the selective-transparency back-surface rendering of the transducer 106 can omit the interior or inner portions of the transducer. Accordingly, in some embodiments, the back-surface may only include outer surfaces of the object.

Example Ending-Surface

Figure 9C:
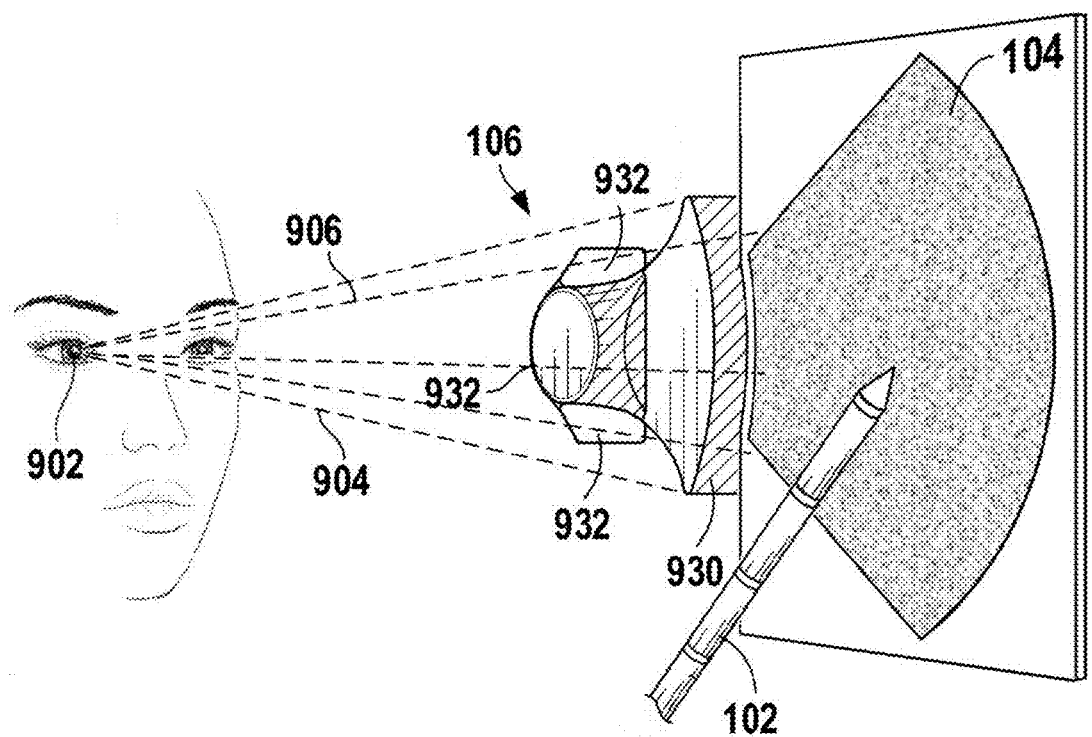

FIG. 9C is a block diagram illustrating an embodiment of a virtual surgical environment. In the illustrated embodiment, an example the ending-surface is shown by the shaded portions 930 of the transducer 106.

In some embodiments, the ending-surface can be described with reference to the view-rays 904 extending from the point-of-view location 902. As illustrated, multiple view-rays intersect with the object 106. Although, in some cases, a particular view-ray may have multiple exit points (for example, view-ray 906), a view-ray that intersects with the object 106 has one final exit point from the object. In some embodiments, the ending-surface can be determined as the aggregation of final exit points of multiple or all of the view-rays 804, as illustrated by the shaded portions 930 of the transducer 106.

In certain embodiments, the ending-surface can omit, the surfaces, edges, or other portions of the transducer 106 that are not included in the aggregation of final exit points of the view-rays 904, such as those portions of the transducer that cannot be seen in FIG. 9B, as well as the non-shaded sides of the transducer 106. Furthermore, the selective-transparency ending-surface rendering of the transducer 106 can omit the interior or inner portions of the transducer. Accordingly, in some embodiments, the ending-surface may only include outer surfaces of the object.

Example Beginning-Surface

Figure 9D:
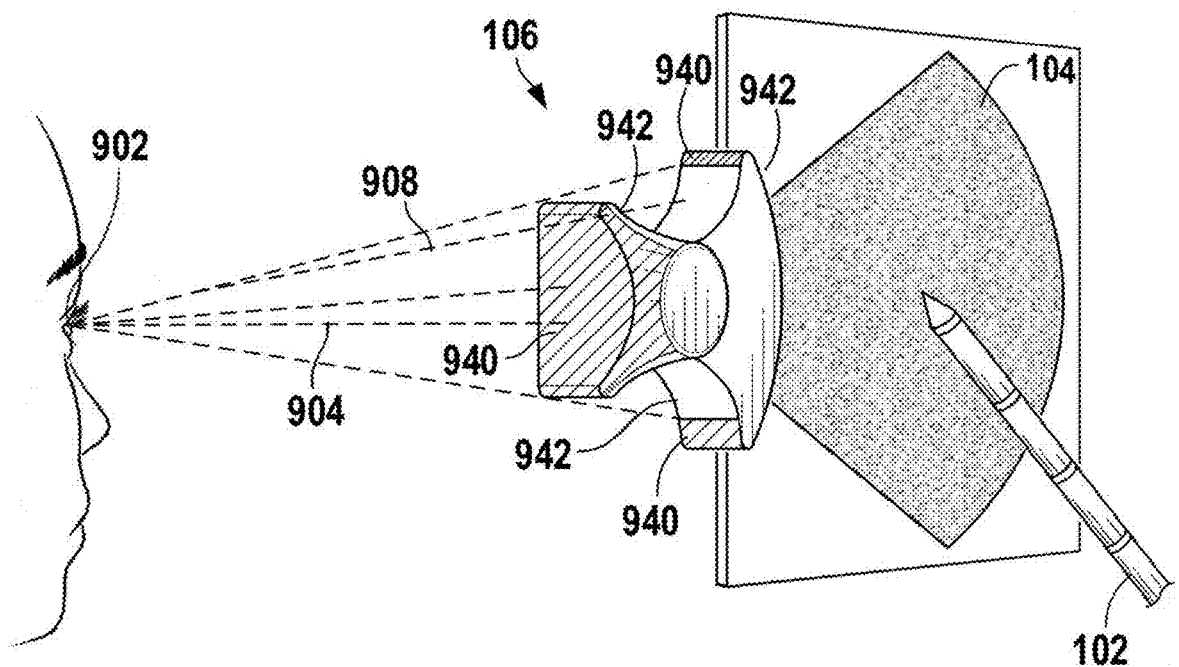

FIG. 9D is a block diagram illustrating an embodiment of a virtual surgical environment. In the illustrated embodiment, an example of a beginning-surface is shown by the shaded portions 940 of the transducer 106. As illustrated by the shaded portions 940, in some embodiments, the beginning-surface can include those surfaces, edges, or other portions of the object 106 that are both facing the point-of-view location 902 and not occluded from view by the object's shape.

In some embodiments, the beginning-surface of an object may also be explained or described with reference to the view-rays 904 which are illustrated as extending from the point-of-view location 902. As illustrated, multiple view-rays 904 intersect with a portion of the object 106. Although, in some cases, a particular view-ray may have multiple entry points (for example, depending on the shape of the object, a view-ray may initially enter the object, then exit the object, then re-enter the object and so on), a view-ray that intersects with the object 106 has one initial entry point into the object. Accordingly, in some embodiments, the beginning-surface can be determined as the aggregation of initial entry points from multiple or all of the view-rays.

In contrast to the front-surface rendering in FIG. 9A, in some cases, the beginning-surface may not include each of the surfaces of the object 106 that face the point-of-view location 902. An example of this is shown by view-ray 908, which intersects two surfaces that are facing the point-of-view location 802, where only the first intersected surface is included in the beginning-surface.

It should be noted that, in certain embodiments, the beginning- and ending-surfaces do not necessarily complement each other to the complete object surface. In other words, the beginning- and ending-surfaces are not necessarily mirror images of each other. For example, as illustrated in FIGS. 9C and 9D, at least some portions of an object may not be included in a beginning-surface or an ending-surface of the object. This can be the case for objects with concavities, for example.

Image Visualization

The system can utilize various methods to generate images 125. In some cases, the system can determine what is to be displayed at the different pixels of the display 170 by fragmenting the display objects or treating the display objects as a combination of fragments. For example, multiple fragments of different display objects can be mapped to the same pixel (non-limiting example: located at the same vertical and horizontal coordinate of the screen 170). When this occurs, the system can determine which fragment, or combination thereof, to display at the pixel. As such, a pixel can display a single fragment or a combination or blend of fragments. For example, if one or more of the portions of different display objects overlap (for example, one display object is in front of another display object), then the system can determine what is to be displayed on the pixels corresponding to the overlapping sections, or fragments, of the display objects. In some embodiments and with reference to the example of one display object being in front of the other, the system can cause the pixel to display a fragment from the front object, a fragment of the back object, or some blend of the fragments.

The system can use a variety of techniques to determine which fragment or combination of fragments are to be displayed at the pixel, such as, but not limited to, depth order, a fragment identifier, a priority identifier, and/or transparency level, etc.

In some cases, the selection can be based on depth order. For example, the closest fragment to the point-of-view location can be selected for each pixel, and the remaining fragments discarded.

As a non-limiting example, the system can start in depth order (for example, front-to-back) and can select the closest fragment (for example, relative to the point-of-view location) that has a fragment identifier corresponding to an ultrasound transducer. The system can discard, ignore, or otherwise not display all other fragments. For example, assuming that the ultrasound transducer is a volume, any particular pixel can have multiple ultrasound transducer fragments, corresponding to the depth of the transducer. In this example, by selecting only the closest fragments of the ultrasound transducer, the result of the rendering would be a beginning-surface rendering of the ultrasound transducer.

A similar technique can be used to render an ending-surface of the transducer. As a non-limiting example, the system can start in depth order and can select the furthest fragment (for example, relative to the point-of-view location) that has a fragment identifier corresponding to an ultrasound transducer. The system can discard, ignore, or otherwise not display all other fragments. For example, the system could proceed in a back-to-front depth order and, similar to the above example, the system can select the first fragment, for each pixel, that has a fragment identifier corresponding to an ultrasound transducer. Alternatively, the system could proceed in a front-to-back depth order and can select the last fragment, for each pixel, that has a fragment identifier corresponding to an ultrasound transducer. The result of these rendering can be an example ending-surface rendering of the ultrasound transducer. It will be understood that similar techniques could be utilized for image guidance data other than a transducer display object. Furthermore, it will be understood that these techniques can be utilized to identify portions of an object other than a beginning- or ending-surface. For example, these techniques can be utilized to render an exterior surface of a display object.

In certain embodiments, at least some of the fragments can include a fragment identifier that can identify, among other things, the object to which it belongs, its depth as compared to the point-of-view location, and/or its coordinates relative to a coordinate plane. In some embodiments, the system can use the identifier to determine which fragment to display at a pixel. For example, the system can determine that trajectory indicators are to always be displayed, regardless of depth position, etc.

Moreover, in certain embodiments, a fragment can be associated with or include a priority identifier that identifies the fragment's priority level relative to other fragments. Accordingly, in some cases, the system can select a fragment or fragments for a particular pixel based at least in part on the fragment identifier(s) of the pixel. In certain embodiments, the fragment can correspond to a pixel on a display that displays an image. In some embodiments, a fragment can refer to one or multiple pixels, such as an array of pixels. When two fragments are mapped to the same pixel, the system can display the fragment with the higher priority level and discard any other fragments.

In some cases, two or more fragments are considered mapped to the same pixel if the fragments satisfy a location threshold. To determine whether the fragments satisfy a location threshold, the system can compare the coordinates of a first fragment with the coordinates of a second fragment. Any coordinate system can be used to compare the coordinates of the fragments. For example, the coordinate system of the display and/or the coordinate system of a medical device can be used, as desired.

In some embodiments, the coordinate system of the display is used. The coordinate system of the display can be any pose as desired. In certain embodiments, the coordinates of the display are that the x-axis is the width of the display, the y-axis is the height of the display, and the z-axis is the depth (e.g., into and out of) the display. In such embodiments, the system 100 can determine that a first fragment satisfies a location threshold and/or is level with a second fragment based at least in part on the x and y coordinates of the fragments. For example, if the x and y coordinates of the first fragment and the x and y coordinates of the second fragment match (or satisfy a distance threshold), the system 100 can determine that the first fragment and the second fragment satisfy the location threshold.

The distance threshold can be a predefined distance, such as one or more bits, one or more pixels, etc. In some embodiments, the distance threshold can be based at least in part on whether the distance between the coordinates is perceptible to a user, which may be based at least in part on the size of the display, the size of the display relative to the image and/or imaged area, and/or the distance between the point-of-view location and the display, etc. For example, in some case the distance threshold can be smaller for larger displays (or larger display:image ratios) and larger for smaller displays (or smaller display:image ratios), or vice versa. In certain cases, the distance threshold can be larger for larger distances between the point-of-view location and the display and smaller for smaller distances between the point-of-view location and the display, or vice versa. In certain embodiments, the distance threshold can be different for each coordinate.

Although reference is made to the x and y coordinates, it will be understood that the coordinates used to determine whether the first fragment and the second fragment satisfy the location threshold can coordinate to any coordinates system. For example, in some embodiments, the coordinate system used can include the x-axis as the depth (e.g., forward/backward), the y-axis as lateral movement (e.g., side-to-side), and the z-axis as elevation (e.g., up/down). In such embodiments, the system 100 can determine that the first fragment satisfies the location threshold if the y and z coordinates of the first fragment match (or satisfy a distance threshold) the y and z coordinates of the second fragment.

In certain embodiments, the system 100 can determine that the first fragment satisfies the location threshold and/or is level with the second fragment if the first fragment and the second fragment are co-located when mapped to a 2D plane. In some embodiments, the 2D plane can be based at least in part on the point-of-view location. For example, the 2D plane can be orthogonal to the point-of-view location. In certain embodiments, the system 100 can determine that the first fragment satisfies the location threshold if the first fragment overlaps with the second fragment in a virtual image (e.g., one is directly in front of or behind the other in the virtual image). In certain embodiments, the system 100 can determine that the first fragment satisfies the location threshold if the first fragment and the second fragment map to the same location on a display, such as the same pixel or same array of pixels.

In some embodiments, the system can blend fragments with the same priority level or with a priority level that satisfies a threshold priority level and discard fragments with a lower priority level or with a priority level that does not satisfy that the threshold priority level. In certain embodiments, the system can blend fragments of different priority levels but display fragments with a higher priority level more opaquely than fragment levels with a lower priority level or give a fragment with a higher priority level a greater weighting when blending (non-limiting example: 70% of pixel is determined based on fragment with higher priority level and 30% is split between fragments with a lower priority level, etc.).

In some cases, the system can use a combination of identifiers to determine what is to be shown at a pixel. For example, the system can, for some pixels, select the closest fragment that has a fragment identifier corresponding to an ultrasound transducer for display, unless another fragment mapped to the same pixel has a higher priority identifier. For example, a fragment that is related to an image guidance cue, such as image guidance cue 112, can be given a higher priority identifier than the priority identifier of the ultrasound transducer. Thus, for pixels that include a transducer fragment, the system can select the closest fragment having a transducer fragment identifier for display. However, if a particular pixel has an image guidance cue fragment with a higher priority identifier, then the system can select the image guidance cue fragment for display instead of the closest transducer fragment, or blend the transducer fragment and the image guidance cue fragment. Such a scenario can result in a rendering that includes a beginning-surface of the transducer, and any image guidance cue that overlaps with the transducer.

In some cases, the system can use a combination of identifiers to determine whether portions of image guidance data intersect. For example, the system can determine, based on one or more identifiers, that an image guidance cue, such as image guidance cue 112, is within the interior of the ultrasound transducer. In other words, the system can determine if the image guidance cue is penetrating the ultrasound transducer. As described above, in some cases, the image guidance cue can be associated with a higher priority identifier than the ultrasound transducer, and thus the system can select the image guidance cue fragment for display instead of the transducer fragment, or blend the transducer fragment and the image guidance cue fragment. Furthermore, in some cases, to further illustrate that the image guidance cue fragment is within the interior of the ultrasound transducer, the system can alter surface attributes of the image guidance cue fragment. For example, the image guidance cue fragment can be emphasized, such as by changing its color, texture, size, or opacity. Alternatively, the image guidance cue fragment can be de-emphasized, such as by changing its color, texture, size, opacity, or by removing or discarding the fragment.

In some cases, the image guidance cue fragment can be removed, discarded, or otherwise not displayed if determined to be within the interior of the transducer. For example, in some cases, a fragment can be given a conditional priority identifier. As a non-limiting example, a fragment that is related to an image guidance cue, such as image guidance cue 112, can be given a higher priority identifier than the priority identifier of the ultrasound transducer, but only if that image guidance cue fragment is not within the interior of the ultrasound transducer (or another object). In other words, in this example, the image guidance cue fragment can have a higher priority identifier when the image guidance cue is in front of or behind, but not within, the ultrasound transducer. Such a scenario can result in a rendering that includes a selected surface of the transducer, and any image guidance cue that is in front of or behind the transducer. However, in this example, any image guidance cue or portion thereof that is within the interior of the transducer may not be shown.

In certain embodiments, a fragment's priority level relative to other fragments can be based on the depth of the object (relative to the point-of-view location) identified by those fragments. For example, an object that is closer to the point-of-view location can be associated with a higher priority identifier than an object that is further from the point-of-view location. As a non-limiting example, a scene can include an ultrasound transducer and a medical image. The ultrasound transducer can be closer to the point-of-view location than the medical image. Furthermore, at least a portion of the transducer intersects with at least a portion of the medical image. In this example, fragments corresponding to the interior of the transducer can have a higher priority level than fragments corresponding the medical image. Thus, for medical image fragments that fall within the interior of the transducer, the system can select a transducer fragment for display instead of the medical image fragment and/or discard the medical image fragments from the rendering. However, in some cases, to enable visibility of the medical image, fragments corresponding to the medical image can have a higher priority identifier if the medical image is behind, but not within, the ultrasound transducer. Thus, for medical image fragments that are behind the transducer (relative to the point-of-view location), the system can select a medical image fragment for display instead of the transducer fragment, or blend the transducer fragment and the medical image fragment. Such a scenario can result in a rendering that includes the selected surface of the transducer, and a portion of a medical image that is visible though the selected surface of the transducer, but that excludes a cutoff region corresponding to the region of the medical image that intersects with, or is within the interior of, the transducer. Examples of this scenario are illustrated in FIGS. 4-9D, where the medical image is illustrated with a curved cutout corresponding to the interior of the transducer. It should be noted that, in some cases, an object that is further from the point-of-view location can be associated with a higher priority identifier than an object that is closer to the point-of-view location. Continuing with the example above, such a scenario can result in a rendering that includes the medical image and a portion of a selected surface of the transducer that excludes a cutoff region corresponding to the region of the transducer that intersects with, or is within the interior of, the medical image.

As described herein, fragments can be blended for display at a pixel. In some cases, at least some of the fragments can be at least partially transparent. For example, the beginning- and/or ending-surface of an object may be selected to be rendered transparently. In examples such as these, the system can select the transparent transducer fragment, as well as a fragment of another object if one happens to overlap at that pixel. Each of the opaque and transparent surface fragments may be composited (for example, accumulated in terms of color and transparency) in depth order. Thus, the fragments can become blended such that both the transducer and the object would be visible at that pixel (for example, the object would be shown through the transducer). In some cases, depth order and compositing formulas may help create the appearance that beginning-surface is in front of (or closer to the point-of-view location than) the ending-surface, and/or that the ultrasound is in front of the other display object.

A number of rendering techniques can be used to generate this visualization including, but not limited to depth peeling (for example, an order independent transparency solution that involves rendering a scene multiple times and each time 'peeling away' layers of the image in depth order), fragment sorting to identify beginning- and ending-surfaces, rendering those objects intended to be transparent to off-screen buffers and transparently compositing those over the main view, ray-casting, or a Binary Space Partition (BSP) Tree algorithm.

Flow Diagrams

Figure 10:
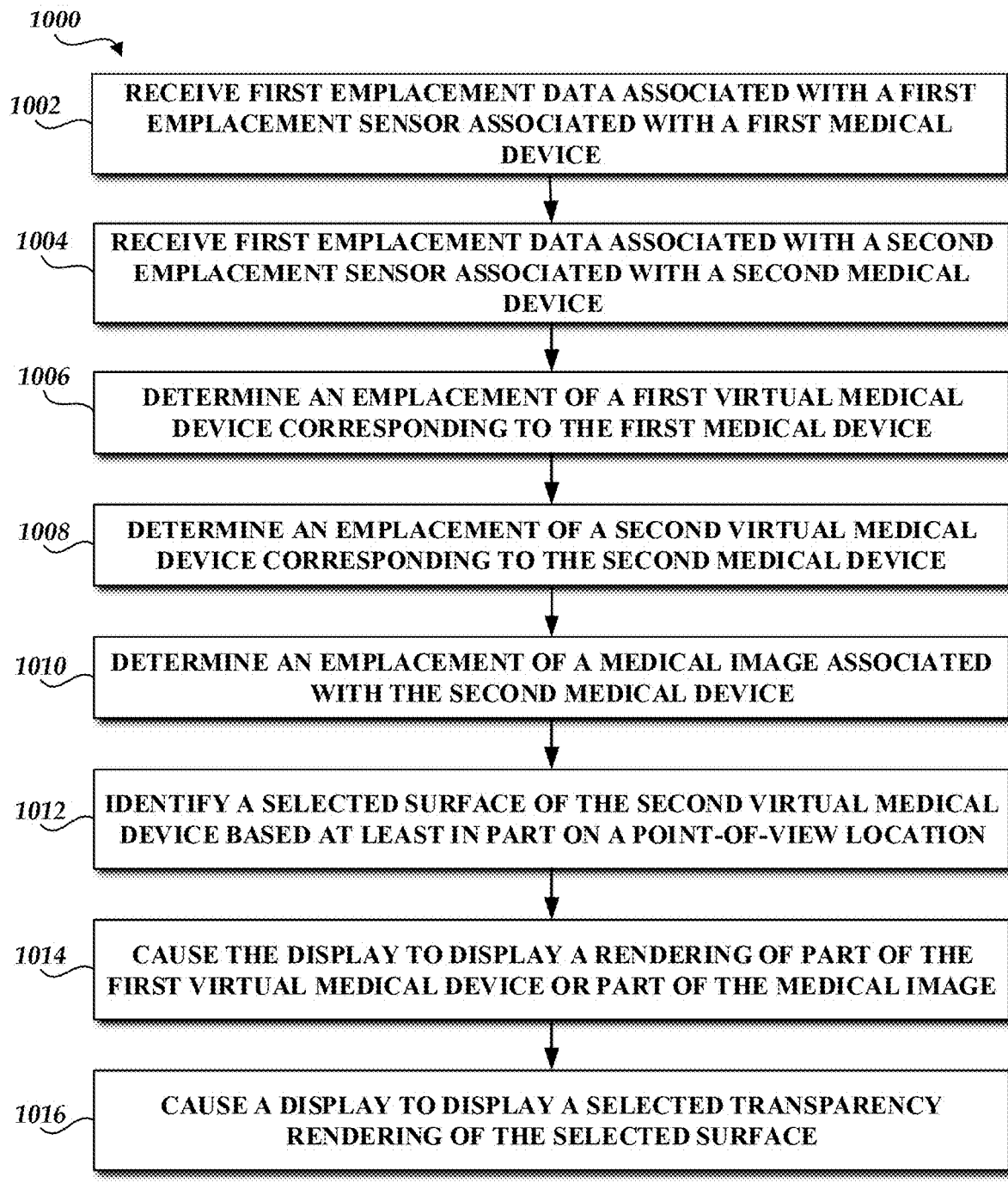
FIG. 10 is a flow diagram illustrative of an embodiment of a routine implemented by the system for providing improved perception of a virtual medical device in a virtual 3D scene for medical device navigation.

FIG. 10 is a flow diagram illustrative of an embodiment of a routine implemented by the system for providing improved perception of a display object in a virtual 3D scene for medical device navigation. One skilled in the relevant art will appreciate that the elements outlined for routine 1000 can be implemented by one or more computing devices/components that are associated with the system 100, such as the position sensing unit 130, the image guidance unit 150, surgical system 180, a head-mounted display, and/or the imaging unit 160. Accordingly, routine 1000 has been logically associated as being generally performed by the system 100. However, the following illustrative embodiment should not be construed as limiting. Furthermore, it will be understood that the various blocks described herein with reference to FIG. 10 can be implemented in a variety of orders. For example, the system 100 can implement some blocks concurrently or change the order as desired. Furthermore, it will be understood that fewer, more, or different blocks can be used as part of the routine 1000. For example, in some embodiments, one or more of blocks 1002, 1004, 1006, 1008, 1010, 1012, 1014, or 1016 are not implemented.

However, it will be understood that any of the blocks (and more or different blocks) can be implemented as part of routine 1000.

At block 1002, the system 100 receives first emplacement data associated with a first emplacement sensor and/or a first medical device. The first emplacement data can be generated by the first emplacement sensor and/or by the position sensing unit 130. In some embodiments, the first emplacement sensor can be associated with the first medical device. For example, the first emplacement sensor can be associated with and/or attached to a single-axis device, such as a medical needle (for example, an ablation needle), a scalpel, a catheter, a stent, or a laparoscopic camera, or a multi-axis device, such as a stapler, a grasper, a transecting device, a resecting device, or a vessel sealer. In some embodiments, the first emplacement sensor can be associated with and/or attached to an imaging device such as an ultrasound transducer.

At block 1004, the system 100 receives second emplacement data associated with a second emplacement sensor and/or a second medical device. The second emplacement data can be generated by the second emplacement sensor and/or by the position sensing unit 130. In some embodiments, the second emplacement sensor can be associated with the second medical device. For example, the second emplacement sensor can be associated with and/or attached to a single-axis device, such as a medical needle (for example, an ablation needle), a scalpel, a catheter, a stent, or a laparoscopic camera, or a multi-axis device, such as a stapler, a grasper, a transecting device, a resecting device, or a vessel sealer. In some embodiments, the second emplacement sensor can be associated with and/or attached to an imaging device such as an ultrasound transducer.

At block 1006, the system 100 can determine an emplacement of a first virtual medical device corresponding to the first medical device based at least in part on the received first emplacement data. As described above, the first virtual medical device can correspond to one or more of an ultrasound transducer, a medical needle, a grasper, a stapler, a vessel sealer, an electrocautery device, a resecting device, a transecting device, a scalpel, a catheter, a stent, or a laparoscopic camera.

In some embodiments, the system 100 can use the first emplacement data and one or more characteristics of the associated first medical device (or a corresponding virtual medical device) to determine the emplacement of at least a portion of the first medical device. For example, characteristics such as shape, size, model, or the like may aid in the determination of an emplacement of the virtual medical device.

In certain embodiments, the system 100 can determine the emplacement of the first medical device in one or more coordinate systems by mapping the first emplacement data, from one coordinate system to a second coordinate system. For example, the first emplacement data may be received with respect to a first coordinate system, such as a position sensing coordinate system, and then mapped to a second coordinate system, such as a 3D scene coordinate system and/or a screen coordinate system. The emplacement of the first medical device can be determined with respect to one or more of the coordinate systems. For example, the emplacement of the first medical device can be determined after the first emplacement data has been mapped to the second coordinate system, such as the 3D scene coordinate system and/or the screen coordinate system, or the emplacement of the first medical device can be determined for the first coordinate system, such as the position sensing coordinate system, and then mapped to the 3D scene coordinate system and/or the screen coordinate system.

In certain embodiments, the system 100 can utilize point-of-view location, as described herein, to determine the emplacement of the first medical device for viewing. For example, the point-of-view location can include one or more of an actual location of a user, an expected location of a user, a fixed location relative to one or more displays, or a dynamic location. For example, the system can track a user in real time and determine the point-of-view location based at least in part on the tracked location of the user.

In certain embodiments, the system 100 can use an offset to determine the emplacement of the first virtual medical device for viewing. For example, the system 100 can determine an initial emplacement of the first medical device in the 3D scene coordinate system and/or the screen coordinate system, and then apply an offset to the initial emplacement and/or the system 100 can determine an initial emplacement of the first medical device in the position sensing coordinate system and apply an offset to the initial emplacement prior to mapping the emplacement of the first medical device in the position sensing coordinate system to the 3D scene coordinate system and/or the screen coordinate system.

The offset can be made in one, or a combination of, coordinate systems, and/or with respect to one, or a combination of, axes. In certain embodiments, the offset can be made along a y-axis (up/down) of the position sensing coordinate system, the 3D scene coordinate system and/or the screen coordinate system. For example, the system 100 can adjust the y-coordinate (up/down coordinate) of the determined emplacement of the first medical device (or the first emplacement sensor(s)) in the position sensing coordinate system by the offset amount. When mapped to the 3D scene coordinate system and/or the screen coordinate system, the system 100 can use the adjusted emplacement. As yet another example, the system 100 can adjust the y-coordinate (up/down coordinate) of the determined emplacement of the first medical device (or the first emplacement sensor(s)) in the 3D scene coordinate system and/or the screen coordinate system by the offset amount. Any combination of the above-referenced examples can be used as desired. Furthermore, it will be understood that the offset can be made in any one or any combinations of the coordinate systems and with reference to any one or any combination of the axes. For example, the adjustment can be made along any one or any combination of the x-axis, y-axis, or z-axis.

Furthermore, the offset can be a predetermined offset and/or a dynamic offset. In some embodiments, a predetermined offset can be used. For example, the system 100 can use a static offset based on an average height of males and/or females or average distance between elbows and hands, the height of the user, a distance between the user's elbow and eyes, expected location of a user with respect to the imaged volume, etc. In certain embodiments, the system 100 can use a dynamic offset, such as a determined emplacement of a head-mounted display (HMD) relative to one or more emplacement sensors, position sensing region, and/or position sensing unit coordinate system. For example, the system 100 can determine the emplacement of an HMD relative to a medical device or imaged area and adjust the offset such that the medical image is always in view on the displays of an HMD. With continued reference to the example, if the wearer crouches down or turns to the side, the system 100 can determine the change in relative emplacement between the HMD and the medical device or imaged area and adjust the offset such that the medical image remains in view in substantially the same emplacement.

In addition, it will be understood that the offset described herein with reference to the first medical device can be applied to any one or any combination of the objects to be displayed and/or to all contents of the virtual 3D scene. In some embodiments, the offset can be applied to some objects to be displayed but not to others.

At block 1008, as described above with respect to block 1006, the system 100 can determine an emplacement of a second virtual medical device corresponding to the second medical device based at least in part on the received second emplacement data. As described above, the second virtual medical device can correspond to an imaging device, such as an ultrasound transducer.

At block 1010, the system 100 can determine an emplacement of a medical image associated with the second medical device based at least in part on received second emplacement data. The medical image can be an intra-operative and/or real-time medical image, such as a live ultrasound or intra-operative CT scan, or can be a pre-operative image, such as a pre-operative CT or MRI scan image. A real-time medical image (or real-time medical imaging stream) can refer to a medical image (or real-time medical imaging stream) received in real-time. The medical image received in real-time can correspond to a live image, such as a live medical image generated by an ultrasound or other image, such as a pre-operative or intra-operative CT image or MRI image that is communicated in real-time.

In some embodiments, the system 100 can use the second emplacement data and one or more characteristics of the second emplacement sensor or associated second medical device (or a corresponding second virtual medical device) to determine the emplacement of the medical image. For example, the characteristics may indicate an emplacement of the medical image relative to the second emplacement sensor or associated second medical device (or second virtual medical imaging device).

The system 100 can determine the emplacement of the medical image relative to the second emplacement sensor and/or associated second medical device (or second virtual medical imaging device). For example, the system 100 can use a known relationship between the second emplacement data and the emplacement of the medical image (non-limiting example: the medical image begins 2 cm. away from the of the second emplacement data location in a particular direction and ends 5 cm. away) and/or use a known relationship between the emplacement of the second emplacement sensor and/or associated second medical device (or second virtual medical imaging device) and the emplacement of the medical image (non-limiting examples: the medical image begins 4 cm. from the tip of the second medical device (or second virtual medical imaging device) and ends at the tip of the second medical device (or second virtual medical imaging device), or the medical image extends 2 cm. in either direction from the ends of the second emplacement sensor).

In certain embodiments, the system 100 can determine the emplacement of the medical image in one or more coordinate systems by mapping the first emplacement data, from one coordinate system to a second coordinate system. For example, the second emplacement data may be received with respect to a first coordinate system, such as a position sensing coordinate system, and then mapped to a second coordinate system, such as a 3D scene coordinate system and/or a screen coordinate system. The emplacement of the medical image can be determined with respect to one or more of the coordinate systems. For example, the emplacement of the medical image can be determined after the second emplacement data has been mapped to the second coordinate system, such as the 3D scene coordinate system and/or the screen coordinate system, or the emplacement of the medical image can be determined for the first coordinate system, such as the position sensing coordinate system, and then mapped to the 3D scene coordinate system and/or the screen coordinate system. In certain embodiments, the system 100 can also use point-of-view location to determine the emplacement of the medical image.

As described above with respect to block 1006, in certain embodiments, the system 100 can also use an offset to determine the emplacement of the medical image for viewing. For example, the system 100 can determine an initial emplacement of the medical image in the 3D scene coordinate system and/or the screen coordinate system, and then apply an offset to the initial emplacement and/or the system 100 can determine an initial emplacement of the medical image in the position sensing coordinate system and apply an offset to the initial emplacement prior to mapping the emplacement of the medical image in the position sensing coordinate system to the 3D scene coordinate system and/or the screen coordinate system.

The offset can be made in one, or a combination of, coordinate systems, and/or with respect to one, or a combination of, axes. In certain embodiments, the offset can be made along a y-axis (up/down) of the position sensing coordinate system, the 3D scene coordinate system and/or the screen coordinate system. For example, the system 100 can adjust the y-coordinate (up/down coordinate) of the determined emplacement of the medical image (or the first emplacement sensor) in the position sensing coordinate system by the offset amount. When mapped to the 3D scene coordinate system and/or the screen coordinate system, the system 100 can use the adjusted emplacement. As yet another example, the system 100 can adjust the y-coordinate (up/down coordinate) of the determined emplacement of the medical image (or the first emplacement sensor) in the 3D scene coordinate system and/or the screen coordinate system by the offset amount. Any combination of the above-referenced examples can be used as desired. Furthermore, it will be understood that the offset can be made in any one or any combinations of the coordinate systems and with reference to any one or any combination of the axes. For example, the adjustment can be made along any one or any combination of the x-axis, y-axis, or z-axis.

Furthermore, the offset can be a predetermined offset and/or a dynamic offset. In some embodiments, a predetermined offset can be used. For example, the system 100 can use a static offset based on an average height of males and/or females or average distance between elbows and hands, the height of the user, a distance between the user's elbow and eyes, expected location of a user with respect to the imaged volume, etc. In certain embodiments, the system 100 can use a dynamic offset, such as a determined emplacement of an HMD relative to one or more emplacement sensors, position sensing region, and/or position sensing unit coordinate system. For example, the system 100 can determine the emplacement of an HMD relative to a medical device or imaged area and adjust the offset such that the medical image is always in view on the displays of an HMD. With continued reference to the example, if the wearer crouches down or turns to the side, the system 100 can determine the change in relative emplacement between the HMD and the medical device or imaged area and adjust the offset such that the medical image remains in view in substantially the same emplacement.

In addition, it will be understood that the offset described herein with reference to the medical image can be applied to any one or any combination of the objects to be displayed and/or to all contents of the virtual 3D scene. In some embodiments, the offset can be applied to some objects to be displayed but not others.

At block 1012, the system 100 can identify a selected surface of the second virtual medical device based at least in part on a point-of-view location. As described herein, the selected surface can include the beginning-surface, the ending-surface, the front-surface, the back-surface, the exterior surface, a side-surface, or other surfaces, or one or more portions thereof.

In some cases, the one or more surfaces can be identified using one or more view-rays, as described herein. For example, imagine a plurality of view-rays extending from the point-of-view location to the second virtual medical device. As described herein, in some cases, the beginning-surface of second virtual medical device can be identified by determining, for multiple or all view-rays, the view-ray's first entry point or first intersection with the second virtual medical device. To determine the beginning-surface, the system can aggregate a first entry point or first intersection from multiple view rays. In addition or alternatively, as described herein, in some cases, the ending-surface of second virtual medical device can be identified by determining, for multiple view-rays, the final exit point or last intersection with the second virtual medical device. To determine the ending-surface, the system can aggregate the final exit point from multiple view-rays. In some cases, the view-rays can extend from a plane of reference, rather than a point-of-reference. For example, the view-rays can extend orthogonally or obliquely from a plane of reference and a subset of the view-rays can intersect with the second virtual medical device, as described above. In this implementation, the beginning-surface can be identified by aggregating the initial entry points from multiple or all of the view-rays, and/or the ending-surface can be identified by aggregating the final exit points from multiple or all of the view-rays.

In some cases, the one or more surfaces can be identified based at least in part on the orientation of the second virtual medical device relative to the point-of-view location. For example, in some cases, a front-surface of the second virtual medical device can be identified by selecting or identifying surfaces, edges, or other portions of the second virtual medical device that are facing the point-of-view location. Similarly, in some cases, a back-surface of the second virtual medical device can be identified by selecting or identifying surfaces, edges, or other portions of the second virtual medical device that are not facing the point-of-view location.

Furthermore, in some cases, a beginning-surface of the second virtual medical device can be identified by selecting or identifying surfaces, edges, or other portions of the second virtual medical device that are facing the point-of-view location and that are not occluded from view by the second virtual medical device's shape. For example, to identify the beginning-surface, the system can determine portions of the second virtual medical device that face, or are oriented towards, the point-of-view location. In other words, the system can determine a front-surface of the second virtual medical device. From those portions that face the point-of-view location (or from the front-surface), the system can select, identify, or determine surfaces, edges, or other portions of the second virtual medical device that are not obstructed from view when viewed from the point-of-view location.

In some cases, the one or more surfaces can be identified based at least in part on the point-of-view location. For example, the beginning-surface of the second virtual medical device can be identified by selecting or identifying surfaces, edges, or other portions of the second virtual medical device that are visible from a point-of-view location.

At block 1014, the system 100 can cause a display to display a view of a virtual 3D scene including a rendering of at least a portion of the first virtual medical device based at least in part on the determined emplacement of the first virtual medical device. In some embodiments, the display of the first virtual medical device can be based at least in part on dimensions of a corresponding real medical device (non-limiting examples: size, shape, or other appearance). As a non-limiting example, the first virtual medical device can include a medical needle. Thus, in some embodiments, the rendering of at least a portion of the first virtual medical device includes at least a portion of a medical needle. However, it will be understood that the rendering of at least a portion of the first virtual medical device can include any portions of the first virtual device.

In addition or alternatively, at block 1014, the system 100 can cause a display to display a view of a virtual 3D scene including a rendering of at least a portion of the medical image based at least in part on the determined emplacement of the second virtual medical device. In some cases, the rendering can include perspective rendering, an orthographic projection, or any other camera projection or viewpoint.

As described above, the view or rendering of the medical image or first virtual medical device can be determined and displayed based at least in part on a point-of-view location. The point-of-view location can be a fixed point-of-view location or a dynamic point-of-view location. For example, the point-of-view location can be set with respect to a specific location in front of the display and/or can be based on a tracked location of the display, the HMD, or the user. In some embodiments, the point-of-view location is determined based at least in part on the relative emplacement of an HMD or user with respect to the position sensing region or imaged volume, or the emplacement of an HMD within a position sensing coordinate system. In embodiments, in which the point-of-view location is based on a tracked location, the system 100 can enable the user to view different views of the virtual 3D scene based on the changing emplacement of the tracked object (HMD, user) relative to the medical devices 140, 145 or the position sensing region.

In certain embodiments, the system 100 can determine multiple emplacements for the first virtual medical device or medical image. For example, the system 100 can determine the emplacement for the medical image for a right-eye view and a left-eye view of a stereoscopic display, such as a HMD. In this way, each display for the HMD can display the medical image from a slightly different perspective corresponding to a right-eye view and a left-eye view, etc.

At block 1016, the system 100 can cause the display to display a selective-transparency rendering of at least a portion of the selected surface(s) of the second virtual medical device. This rendering can be based at least in part on the determined emplacement of the second virtual medical device. Furthermore, the rendering can be based at least in part on the identification of the selected surface(s) at block 1012.

As described herein, the selective-transparency rendering of the selected surface(s) of the second virtual medical device can include a display of the selected surface at varying transparency levels, with other portions of the second virtual medical device, such as the non-selected surfaces being omitted, not shown, or completely transparent. It will be understood that multiple surfaces can be used as part of a selective-transparency rendering. For example, a selective-transparency surface rendering can include a beginning-surface, ending-surface, front-surface, rear-facing surface, side-facing surface, etc.

The selective-transparency rendering of the selected surface can be implemented with the selected surface becoming less transparent as it gets closer to an edge. In this way, image guidance data, such as the first virtual medical device, the medical image, or image guidance cues can be visible through the second virtual medical device, and the spatial relationships between each of the first virtual medical device, second virtual medical device, medical image, and image guidance cues can be accurately identified. In some embodiments, the selective-transparency rendering of the selected surface of the second virtual medical device can reduce the number of displayed lines and improve a user's ability to properly understand the correct orientation of the second virtual medical device.

It will be understood that the selective-transparency of the selected surface can be implemented in a variety of ways. For example, the selective-transparency can include displaying the selected surface at the same transparency level, displaying edges of the surface opaquely or as solid or dashed lines (non-limiting example: wire frame) and the rest of the selected surface transparently or vice versa, displaying portions of the surface that are in front of another display object transparently or more transparently than portions of the selected surface that are not in front of another display object, etc.

Moreover, when a selective-transparency rendering includes multiple surfaces, each surface can be rendered using the same selective-transparency or different selective transparencies. For example, a beginning-surface can be rendered such that portions of the beginning-surface that are closer to an edge are rendered at a different opacity (for example, more opaquely) than portions that are farther away from an edge. As another example, an ending-surface can be rendered such that the entire surface has a single level of transparency or alternatively can be rendered such that only edges of the ending-surface are rendered opaquely, while other portions of the ending-surface are render with a diminished opacity or are completely transparent.

Furthermore, as described herein, the selected surfaces can be rendered selectively transparent in a variety of ways. For example, the system can render portions of the selected surface of the second virtual medical device that overlap with other display objects (for example, the first virtual medical device or the medical image) transparently or more transparently than non-overlapping portions of the second virtual medical device, which can be rendered opaquely (for example, like the transducer 106 as illustrated in FIG. 3). In certain embodiments, the non-overlapping portions of the second virtual medical device can be displayed at one or more different transparency levels similar to the overlapping portions of the selected surface.

In some embodiments, the rendering of the second virtual medical device can include shading and other visualization techniques to illustrate contours of the second medical device. For example, in some cases, surface shading can be added to the selected surface rendering of the second virtual medical device, which can make the second virtual medical device more salient and easier to see, despite its transparency.

As described herein, in some cases, rendering the selective-transparency rendering of the selected surface of the second virtual medical device can include omitting, ignoring, rendering transparently or otherwise not showing portions of the second virtual medical device that are not portions of the selected surface(s). For example, portions that are not part of the selected surface can include the beginning-surface, ending-surface, back-surface, front-surface, interior, one or more sides, or the like.

It will be understood that the various blocks described herein can be implemented in a variety of orders, and that the system 100 can implement one or more of the blocks concurrently and/or change the order, as desired. For example, the system 100 can concurrently receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1000. For example, the routine 1000 can include blocks for receiving emplacement data associated with additional emplacement sensors or medical devices, determining emplacements of one or more medical devices, corresponding virtual medical devices, other display objects, displays, and/or users. In some embodiments, the routine 1000 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, intersection indicators, or medical devices in different states or configurations.

Furthermore, similar to the identification of the selected surface of the second virtual medical device, the system can identify a selected surface of other image guidance data, such as the first second virtual medical device or the medical image based at least in part on the point-of-view location, the system can render those one or more selected surfaces. For example, it can be advantageous for the physician to see at least the selected surface of every display object. Accordingly, in some cases, each display object (or portion of each display object) that is not blocked by another display object (with respect to the point-of-view location) can be rendered with a selective-transparency rendering of the selected surface. For instance, referring to the illustrated embodiment of FIG. 4, a portion of the virtual needle 102 overlaps with a portion of the medical image 104. In some cases, at least one of the selected surfaces of the virtual needle 102 or the medical image 104 can be displayed using a selective-transparency rendering such that each selected surface portion of every portion of image guidance data is visible to the physician. Furthermore, in some embodiments, all of the image guidance data, or a subset thereof, can be displayed using a selective-transparency rendering.

Furthermore, in some cases, as described herein, the system can identify and/or selectively display one or more fragments corresponding to the display objects. For example, the system can determine what is to be displayed at the different pixels of the display 170 by fragmenting the display objects or treating a display object as a combination of fragments. For example, multiple fragments of the same display object or different display objects can be mapped to the same pixel (non-limiting example: located at the same vertical and horizontal coordinate of the screen 170). When this occurs, the system can determine which fragment, or combination thereof, to display at the pixel.

As described herein, the system can use a variety of techniques to determine which fragment or combination of fragments are to be displayed at the pixel, such as, but not limited to, depth order, a fragment identifier, a priority identifier, and/or transparency level, etc. For example, in some cases, the system can display use the fragment(s) corresponding to the display object that is closest to the point-of-view location to determine what is to be displayed at the pixel, and discard fragments from other display objects. In certain cases, the system can use the fragment with the highest priority identifier or level to determine what is to be displayed at the pixel. For example, if fragments for an image guidance cue (having the highest priority identifier), medical image (having the lowest priority identifier), and transducer are mapped to the same pixel, the system can use the image guidance cue fragment to determine what to display at the pixel and discard the transducer and medical image fragments. In another instance and with reference to the same example, the system can use a combination of the image guidance cue and transducer to determine what to display at the pixel, etc. In some embodiments, the system can use a combination of features to determine what is to be displayed at the pixel. For example, the system can use depth order and a priority identifier to determine which fragments to use for a pixel.

In addition, in some cases, the routine 1000 can omit certain blocks, such as, but not limited to, blocks 1002, 1004, 1006, 1010, and/or 1014. For example, in some embodiments, the system may not determine emplacement of and/or may not display a portion of the first virtual medical device or a portion of the medical image.

Figure 11:
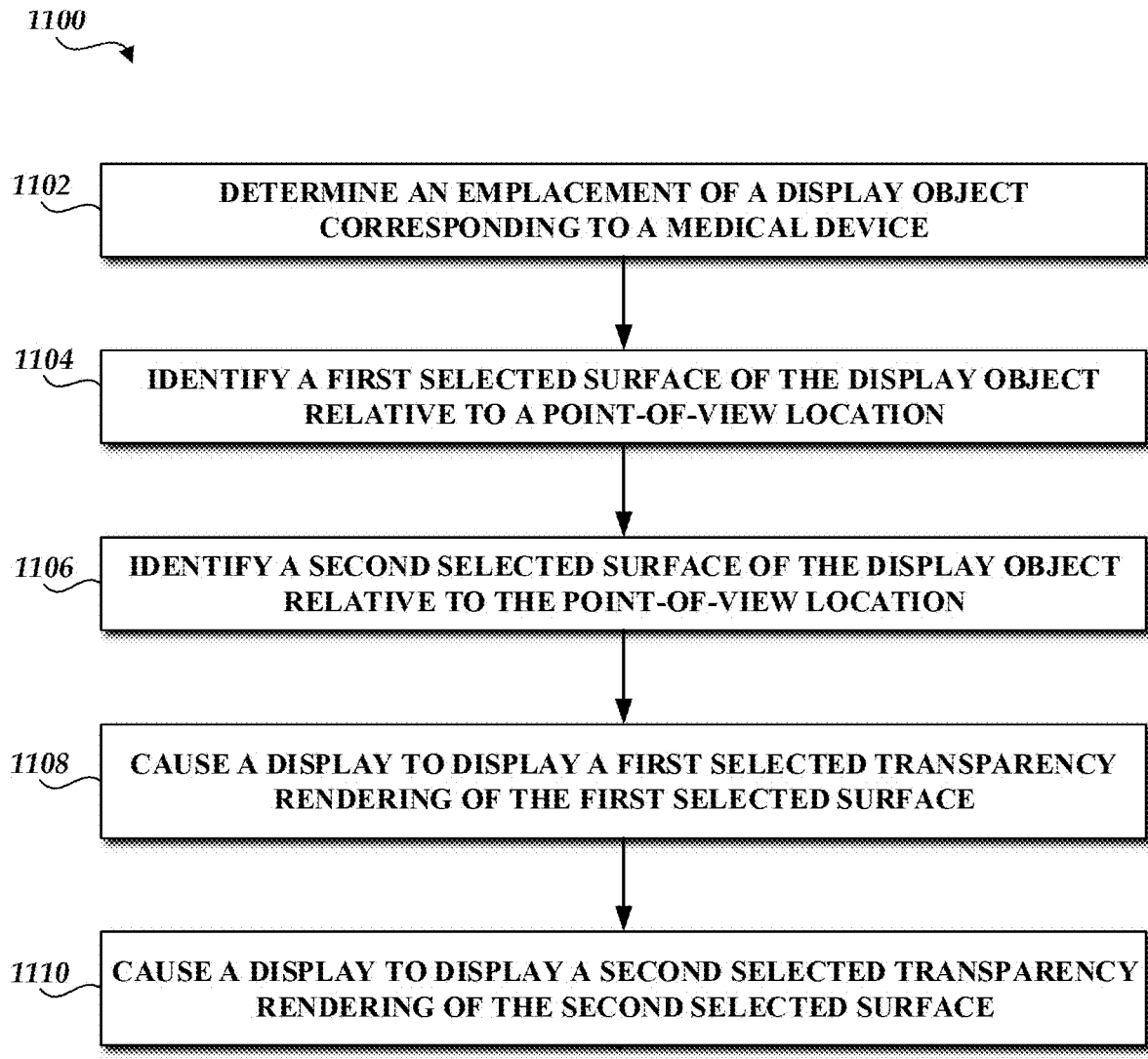
FIG. 11 is a flow diagram illustrative of an embodiment of a routine implemented by the system for providing improved perception of a display object in a virtual 3D scene for medical device navigation.

FIG. 11 is a flow diagram illustrative of an embodiment of a routine implemented by the system for improved perception of a display object in a virtual 3D scene for medical device navigation. One skilled in the relevant art will appreciate that the elements outlined for routine 1100 can be implemented by one or more computing devices/components that are associated with the system 100, such as the position sensing unit 130, the image guidance unit 150, surgical system 180, an HMD, and/or the imaging unit 160. Accordingly, routine 1100 has been logically associated as being generally performed by the system 100. However, the following illustrative embodiment should not be construed as limiting. Furthermore, it will be understood that the various blocks described herein with reference to FIG. 11 can be implemented in a variety of orders. For example, the system 100 can implement some blocks concurrently or change the order as desired. Furthermore, it will be understood that fewer, more, or different blocks can be used as part of the routine 1100. However, it will be understood that any of the blocks (and more or different blocks) can be implemented as part of routine 1100.

At block 1102, as described similarly above with reference to block 1008 of FIG. 10, the system 100 can determine an emplacement of a first display object. This determination can be based at least in part on received emplacement data. As described herein, display objects can include virtual medical device, medical images, or the like. In some cases, this routine can be implemented for image guidance data other than display objects, such as image guidance cues like trajectory indicators, affected region indicators, or intersection indicators.

At block 1104, as described similarly above with reference to block 1012 of FIG. 10, the system 100 can identify a first selected surface of the display object relative to a point-of-view location. As described herein, the first selected surface can include the beginning-surface, the ending-surface, the front-surface, the back-surface, the exterior surface, a side-surface, or other surfaces, or one or more portions thereof.

At block 1104, the system 100 can identify a second selected surface of the display object that is different from the first selected surface. In some embodiments, the second selected surface can be identified in a manner similar to the first selected surface. As described herein, the second selected surface can include the beginning-surface, the ending-surface, the front-surface, the back-surface, the exterior surface, a side-surface, or other surfaces, or one or more portions thereof, and can be different from the first selected surface.

At block 1108, as similarly described above with respect to block 1016 of FIG. 10, the system 100 can display a selective-transparency surface rendering of the first selected surface of the display object.

As a non-limiting example, the first selected surface can include the beginning-surface of the display object. As described herein, the selective-transparency beginning-surface rendering of the display object can include a display of the beginning-surface at varying transparency levels, with other portions of the display object, such as the back-, ending-, interior, or sides being omitted, shown differently, not shown, or shown completely transparently. In some cases, the selective-transparency beginning-surface rendering can be implemented with the beginning-surface becoming less transparent as it gets closer to an edge. In this way, image guidance data, such as another display object or image guidance cues can be visible through the display object, and the spatial relationships between each of the display object and other image guidance data can be accurately identified. In some embodiments, the selective-transparency beginning-surface rendering of the display object can reduce the number of displayed lines and improve a user's ability to properly understand the correct orientation of the display object.

It will be understood that the selective-transparency beginning-surface rendering can be implemented in a variety of ways. For example, the selective-transparency can include displaying the beginning-surface at a single transparency level, displaying edges of the surface opaquely or as solid or dashed lines (non-limiting example: wire frame) and the rest of the beginning-surface transparently or vice versa, displaying portions of the beginning-surface that are in front of another display object transparently or more transparently than portions of the beginning-surface that are not in front of another display object, etc.

Furthermore, as described herein, the beginning-surface can be rendered selectively transparent in a variety of ways. For example, the system can render portions of the beginning-surface of the display object that overlap with other display objects (for example, another display object or image guidance cues) transparently or more transparently than non-overlapping portions of the display object, which can be rendered opaquely (for example, like the transducer 106 as illustrated in FIG. 3). In certain embodiments, the non-overlapping portions of the display object can be displayed at one or more different transparency levels similar to the overlapping portions of the beginning-surface.

In some embodiments, the rendering of the beginning-surface can include shading and other visualization techniques to illustrate contours of the second medical device. For example, in some cases, surface shading can be added to the beginning-surface rendering of the second virtual medical device, which can make the second virtual medical device more salient and easier to see, despite its transparency.

As described herein, in some cases, the selective-transparency beginning-surface rendering can include omitting, ignoring, rendering transparently or otherwise not showing portions of the display object that are not portions of the beginning-surface. For example, portions that are not part of the beginning-surface can include the ending-surface, back-surface, interior, one or more sides, or the like.

At block 1110, as similarly described above with respect to blocks 1108, the system 100 can cause the display to display a selective surface rendering of at least a portion of the second selected surface of the display object.

As a non-limiting example, the second selected surface can include the ending-surface of the display object. When a selective-transparency surface rendering includes multiple surfaces, such as a first and second surface or a beginning- and ending-surface, each surface can be rendered using the same selective-transparency or different selective transparencies. For example, a beginning-surface can be rendered such that portions of the beginning-surface that are closer to an edge are rendered at a different opacity (for example, more opaquely) than portions that are farther away from an edge. As another example, an ending-surface can be rendered such that the entire surface has a single level of transparency or alternatively can be rendered such that only edges of the ending-surface are rendered opaquely, while other portions of the ending-surface are render with a diminished opacity or are completely transparent.

It will be understood that the various blocks described herein can be implemented in a variety of orders, and that the system 100 can implement one or more of the blocks concurrently and/or change the order, as desired. For example, the system 100 can concurrently receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1100. For example, the routine 1100 can include blocks for receiving emplacement data associated with additional emplacement sensors or medical devices, determining emplacements of one or more medical devices, corresponding virtual medical devices, other display objects, displays, and/or users. In some embodiments, the routine 1100 can include receiving emplacement data or determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, as described above. In addition, in some cases, the routine 1100 can omit certain blocks, such as, but not limited to, blocks 1104 and 1108, or 1106 and 1110. For example, in some embodiments, the system may not identify or display a beginning-surface of the display object. Similarly, in some embodiments, the system may not identify or display an ending-surface of the display object.

In some cases, multiple display objects can be displayed using the same or different selective-transparency renderings. For example, if two or more objects overlap, the closest display object or portion thereof (relative to the point-of-view location) can be displayed using a first selective-transparency rendering, and the second closest display object or portion thereof (relative to the point-of-view location) can be displayed using a second selective-transparency rendering. In some cases, the first and second selective-transparency renderings of the first and second display objects can be different. For example, the second display object can use a different selective-transparency scheme, such as more transparent or a single transparency level. In some cases, using different selective-transparency rendering schemes to display different display object can allow overlapping portions of different display objects to be visible to the user, and can enable the user to understand the spatial relationships between each display object, or other image guidance data.

Furthermore, in some cases, as described herein, the system can identify and/or selectively display one or more fragments corresponding to the display objects. For example, the system can determine what is to be displayed at the different pixels of the display 170 by fragmenting the display objects or treating a display object as a combination of fragments. For example, multiple fragments of the same display object or different display objects can be mapped to the same pixel (non-limiting example: located at the same vertical and horizontal coordinate of the screen 170). When this occurs, the system can determine which fragment, or combination thereof, to display at the pixel.

As described herein, the system can use a variety of techniques to determine which fragment or combination of fragments are to be displayed at the pixel, such as, but not limited to, depth order, a fragment identifier, a priority identifier, and/or transparency level, etc. For example, in some cases, the system can display use the fragment(s) corresponding to the display object that is closest to the point-of-view location to determine what is to be displayed at the pixel, and discard fragments from other display objects. In certain cases, the system can use the fragment with the highest priority identifier or level to determine what is to be displayed at the pixel. For example, if fragments for an image guidance cue (having the highest priority identifier), medical image (having the lowest priority identifier), and transducer are mapped to the same pixel, the system can use the image guidance cue fragment to determine what to display at the pixel and discard the transducer and medical image fragments. In another instance and with reference to the same example, the system can use a combination of the image guidance cue and transducer to determine what to display at the pixel, etc. In some embodiments, the system can use a combination of features to determine what is to be displayed at the pixel. For example, the system can use depth order and a priority identifier to determine which fragments to use for a pixel.

In addition, it will be understood that the various blocks described herein with reference to FIG. 11 can be implemented in routine 1100, in a variety of orders. For example, the system 100 can implement some or all of various blocks of FIG. 11 in routine 1100 concurrently or change the order as desired. In addition or alternatively, it will be understood that any of the various blocks described herein with reference to FIG. 10 can be implemented in routine 1100, in a variety of orders. For example, the system 100 can implement some or all of various blocks of FIG. 10 in routine 1100 concurrently or change the order as desired.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (non-limiting example: not all are necessary for the practice of the algorithms). Moreover, in certain embodiments, operations, acts, functions, or events can be performed concurrently, non-limiting examples: through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system 100. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, non-limiting examples: a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices.

Virtualization technologies allow a single physical computing device to host one or more instances of a virtual machine, which virtual machine instance appears to a user as an independent computing device. With virtualization, the host computing device can create, maintain, delete, or otherwise manage virtual machines instances in a dynamic manner. In turn, users can request computing resources, including single computing devices or a configuration of networked computing devices, and be provided with virtual machine instances that provide the requested computing resources.

An instance of a virtual machine may be configured to provide specific functionality. For example, a virtual machine instance may be associated with different combinations of software applications and operating systems or operating system configurations to enable a virtual machine to provide different desired functionalities, or to provide similar functionalities more efficiently.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. For example, while only one aspect of the invention may be recited as a means-plus-function claim under 35 U.S.C sec. 108(f) (AIA), other aspects may likewise be embodied as a means-plus-function claim, or in other forms, such as being embodied in a computer-readable medium. Any claims intended to be treated under 35 U.S.C. § 108(f) will begin with the words "means for", but use of the term "for" in any other context is not intended to invoke treatment under 35 U.S.C. § 108(f). Accordingly, the applicant reserves the right to pursue additional claims after filing this application, in either this application or in a continuing application.

Disjunctive language such as the phrase "at least one of X, Y, or Z," unless specifically stated otherwise, is otherwise understood with the context as used in general to present that an item, term, etc., may be either X, Y, or Z, or any combination thereof (non-limiting examples: X, Y, and/or Z). Thus, such disjunctive language is not generally intended to, and should not, imply that certain embodiments require at least one of X, at least one of Y, or at least one of Z to each be present.

Unless otherwise explicitly stated, articles such an "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

The previous description of the disclosed implementations is provided to enable a person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments described herein can be applied to other systems in which non-medical objects are tracked and non-medical image streams are received, and virtual representations are displayed on a display and/or systems in which multiple objects are displayed on a display within a virtual space, such as within a virtual 3D space. Thus, the present invention is not intended to be limited to the implementations shown herein but is to be accorded the widest scope consistent with the principles and novel features disclosed herein.

We claim:

1. A method for providing image guidance, the method comprising:
   receiving emplacement information associated with a medical imaging device;
   determining an emplacement of a virtual medical imaging device associated with the medical imaging device based at least in part on the emplacement information;
   identifying a first surface of the virtual medical imaging device based at least in part on a point-of-view location, wherein the first surface corresponds to a plurality of view-rays extending from the point-of-view location to the virtual medical imaging device, wherein said identifying the first surface comprises:
      determining, for a first set of view-rays of the plurality of view-rays, a first entry point into the virtual medical imaging device, and
      aggregating the first entry points of the first set of view-rays;
   identifying a second surface of the virtual medical imaging device based at least in part on the point-of-view location, wherein said identifying the second surface comprises:
      determining, for a second set of view-rays of the plurality of view-rays, a final exit point out of the virtual medical imaging device, and
      aggregating the final exit points of the second set of view-rays; and
   causing a display to display:
      the first surface of the virtual medical imaging device at a first transparency level; and
      the second surface of the virtual medical imaging device at a second transparency level that is different from the first transparency level.

2. The method of claim 1, wherein the first surface comprises a beginning-surface of the virtual medical imaging device, wherein the second surface comprises an ending-surface of the virtual medical imaging device.

3. The method of claim 1, wherein the first surface comprises a first set of edges of the virtual medical imaging device, wherein the second surface comprises a second set of edges of the virtual medical imaging device.

4. The method of claim 1, further comprising causing the display to display portions of the first surface that are closer to an edge of the virtual medical imaging device at a different opacity than portions of the first surface that are farther away from an edge of the virtual medical imaging device.

5. The method of claim 1, wherein the medical imaging device comprises at least one of an ultrasound transducer.

6. The method of claim 1, further comprising causing the display to display portions of the second surface that are closer to an edge of the virtual medical imaging device at a different opacity than portions of the second surface that are farther away from an edge of the virtual medical imaging device.

7. The method of claim 4, further comprising causing the display to display portions of the second surface that are closer to an edge of the virtual medical imaging device at a different opacity than portions of the second surface that are farther away from an edge of the virtual medical imaging device.

8. The method of claim 4, wherein the emplacement information is real time emplacement information and wherein the emplacement information changes based on a change in at least one of a position or orientation of the medical imaging device.

9. The method of claim 4, further comprising:
determining an emplacement of a medical image associated with the medical imaging device; and
causing the display to display at least a portion of the medical image.

10. A system, comprising:
a display; and
one or more processors in communication with the display and configured to:
receive emplacement information from a tracking device associated with a medical device;
determine an emplacement of a display object associated with the medical device relative to a point-of-view location;
determine, for a first set of view-rays of a plurality of view-rays extending from a point-of-view location to the display object, a first entry point into the display object,
identify a first surface of the display object based at least in part on an aggregation of the first entry points of the first set of view-rays;
determine, for a second set of view-rays of the plurality of view-rays, a final exit point out of the display object,
identify a second surface of the display object based at least in part on an aggregation of the final exit points of the second set of view-rays; and
cause the display to display a rendering of the first surface of the display object and a rendering of the second surface of the display object, wherein the rendering of the first surface of the display object is displayed differently from the rendering of the second surface of the display object.

11. The system of claim 10, wherein the display object is a virtual medical device corresponding to the medical device.

12. The system of claim 10, wherein the first surface comprises a beginning-surface of the display object, wherein the second surface comprises an ending-surface of the display object.

13. The system of claim 10, wherein the rendering of the first surface comprises only edges of the display object.

14. The system of claim 10, wherein the rendering of the first surface comprises a display of portions of the first surface that are closer to an edge of the display object at a different opacity than portions of the first surface that are farther away from an edge of the display object.

15. The system of claim 10, wherein the medical device comprises at least one of an ultrasound transducer, a medical needle, a grasper, a stapler, a vessel sealer, an electrocautery device, a resecting device, a transecting device, a scalpel, a catheter, a stent, or a laparoscopic camera.

16. The system of claim 10, wherein to identify a first surface of the display object, the one or more processors are configured to identify regions of the display object that are visible from the point-of-view location.

17. The system of claim 10, wherein to identify the first surface of the display object, the one or more processors are configured to:
determine surfaces of the display object that face the point-of-view location; and
identify, from the surfaces that face the point-of-view location, portions of the display object that are not obstructed from view when viewed from the point-of-view location.

18. The system of claim 10, wherein to identify the first surface of the display object, the one or more processors are configured to discard portions of the display object that are not visible from the point-of-view location.

* * * * *